(12) United States Patent
Franciskovich et al.

(10) Patent No.: US 7,511,066 B2
(45) Date of Patent: Mar. 31, 2009

(54) ANTITHROMBOTIC AROMATIC ETHERS

(75) Inventors: Jeffry Bernard Franciskovich, Zionsville, IN (US); Theodore Goodson, Jr., Indianapolis, IN (US); David Kent Herron, Indianapolis, IN (US); Angela Lynn Marquart, Greenwood, IN (US); John Joseph Masters, Fishers, IN (US); David Mendel, Indianapolis, IN (US); Leander Merritt, Indianapolis, IN (US); Andrew Michael Ratz, Zionsville, IN (US); Gerald Floyd Smith, Greenwood, IN (US); Michael Robert Wiley, Zionsville, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 396 days.

(21) Appl. No.: 10/571,373

(22) PCT Filed: Sep. 24, 2004

(86) PCT No.: PCT/US2004/028809

§ 371 (c)(1),
(2), (4) Date: Mar. 10, 2006

(87) PCT Pub. No.: WO2005/049604

PCT Pub. Date: Jun. 2, 2005

(65) Prior Publication Data

US 2007/0027185 A1 Feb. 1, 2007

Related U.S. Application Data

(60) Provisional application No. 60/507,439, filed on Sep. 30, 2003.

(51) Int. Cl.
*A61K 31/4427* (2006.01)
*C07D 417/12* (2006.01)
(52) U.S. Cl. .................................. 514/352; 546/270.7
(58) Field of Classification Search ................. 514/352; 546/270.7
See application file for complete search history.

(56) References Cited

U.S. PATENT DOCUMENTS

| 3,518,297 | A  | 6/1970  | Busacca et al. |
|-----------|----|---------|----------------|
| 3,949,084 | A  | 4/1976  | Pfister et al. |
| 4,159,330 | A  | 6/1979  | Doria et al.   |
| 6,140,351 | A  | 10/2000 | Arnaiz et al.  |
| 6,313,122 | B1 | 11/2001 | Beight et al.  |
| 6,313,151 | B1 | 11/2001 | Beight et al.  |
| 6,372,759 | B1 | 4/2002  | Beight et al.  |
| 6,376,515 | B2 | 4/2002  | Zhu et al.     |
| 6,417,200 | B1 | 7/2002  | Beight et al.  |
| 6,610,704 | B1 | 8/2003  | Beight et al.  |
| 6,635,657 | B1 | 10/2003 | Beight et al.  |
| 6,689,780 | B1 | 2/2004  | Beight et al.  |
| 6,844,367 | B1 | 1/2005  | Zhu et al.     |
| 2004/0058959 | A1 | 3/2004 | Herron et al. |
| 2004/0097491 | A1 | 5/2004 | Herron et al. |
| 2004/0242581 | A1 | 12/2004 | Herron et al. |

FOREIGN PATENT DOCUMENTS

| AU | 2001-29827     | 10/2001 |
|----|----------------|---------|
| EP | 1 273 575      | 1/2003  |
| GB | 1153994        | 6/1969  |
| GB | 1276359        | 6/1972  |
| JP | 2000-302765    | 10/2000 |
| WO | WO 94/26260    | 11/1994 |
| WO | WO 99/00121    | 1/1999  |
| WO | WO 99/00128    | 1/1999  |
| WO | WO 02/10154    | 2/2002  |
| WO | WO 02/064567   | 8/2002  |
| WO | WO 2004/108677 | 12/2004 |

OTHER PUBLICATIONS

Zhu, et al.: "Factor Xa Inhibitors: Recent Advances in Anticoagulant Agents" Annual Reports in Medicinal Chemistry, (2000), 35, 83-102.

*Primary Examiner*—Taofiq A Solola
(74) *Attorney, Agent, or Firm*—Thomas E. Jackson

(57) ABSTRACT

This application relates to a compound of formula I (or a prodrug thereof or a pharmaceutically acceptable salt of the compound or prodrug thereof) as defined herein, pharmaceutical compositions thereof, and its use as an inhibitor of factor Xa and/or thrombin, as well as a process for its preparation and intermediates therefor.

16 Claims, No Drawings

ANTITHROMBOTIC AROMATIC ETHERS

This application claims the benefit of U.S. Provisional Application No. 60/507,439, filed Sep. 30, 2003, which is incorporated by reference herein in its entirety.

This invention relates to antithrombotic aromatic ethers which demonstrate activity as inhibitors of thrombin and/or factor Xa and, accordingly, which are useful antithrombotics in mammals. In particular it relates to antithrombotic aromatic ethers having high anticoagulant activity, good oral exposure and antithrombotic activity. Thus, this invention relates to new antithrombotic aromatic ethers which are inhibitors of thrombin and/or factor Xa, pharmaceutical compositions containing the antithrombotic aromatic ethers as active ingredients, and the use of the antithrombotic aromatic ethers as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic aromatic ethers are useful as anticoagulants in in vitro applications.

The process of blood coagulation, thrombosis, is triggered by a complex proteolytic cascade leading to the formation of thrombin. Thrombin proteolytically removes activation peptides from the Aa-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6-24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, for example, B. Y. Zhu and R. M. Scarborough, *Annual Reports in Medicinal Chemistry*, (2000), 35, 83-102, Factor Xa Inhibitors: Recent Advances in Anticoagulant Agents.

Although the heparins and coumarins are effective anticoagulants, there still exists a need for anticoagulants which act selectively on factor Xa and/or thrombin, and which, independent of antithrombin III, exert inhibitory action shortly after administration, preferably by an oral route, and do not interfere with lysis of blood clots, as required to maintain hemostasis.

The present invention is directed to the discovery that the antithrombotic aromatic ethers of the present invention, as defined below, are potent inhibitors of thrombin and/or factor Xa which may have high bioavailability following oral administration.

According to the invention there is provided a compound of formula I

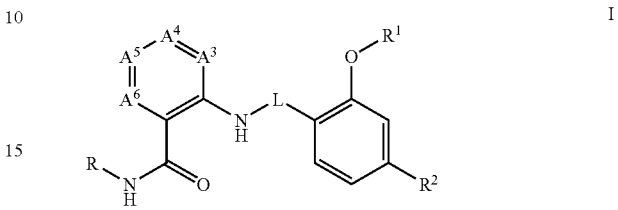

or a pharmaceutically acceptable salt thereof, wherein:

$A^3$, $A^4$, $A^5$ and $A^6$, together with the two carbons to which they are attached, complete a substituted heteroaromatic ring in which one of $A^3$, $A^4$, $A^5$ and $A^6$ is N, and each of the others is $CR^3$, $CR^4$, $CR^5$ or $CR^6$, respectively; wherein each of $R^3$, $R^4$, $R^5$ and $R^6$ is hydrogen; or one or more of $R^3$, $R^4$, $R^5$ and $R^6$ is methyl each of the others is hydrogen; or one of $R^3$, $R^4$, $R^5$ and $R^6$ attached to a carbon which is not bonded to an N-atom is chloro and each of the others are hydrogen; or two adjacent residues of $A^3$, $A^4$, $A^5$ and $A^6$ together form S, and each of the others is CH;

L is carbonyl or methylene;

R is 2-pyridinyl (which may bear a methyl, cyano, carbamoyl, hydroxymethyl, formyl, vinyl, amino, hydroxy, methoxy, difluoromethoxy, methylthio, fluoro or chloro substituent at the 5-position), or R is 3-pyridinyl (which may bear a methyl, fluoro or chloro substituent at the 6-position), or R is 2-thiazolyl (which may bear a methyl substituent at the 4-position or a bromo substituent at the 5-position), or R is phenyl (which may bear one, two or three substituents at the 3-, 4- or 5-position(s) independently selected from fluoro, chloro, bromo, cyano, carbamoyl, methyl, methoxy, difluoromethoxy, hydroxymethyl, formyl, vinyl, amino, hydroxy and 3,4-methylenedioxy; and in addition the phenyl may bear a 2-chloro or 2-fluoro substituent), or R is 6-indolyl (which may bear a chloro or methyl substituent at the 3-position);

$R^1$ is —$(CH_2)_i$-Q-$(CH_2)_j$—$NR^aR^b$ in which a) Q is a single bond; the sum of i and j is 2 or 3; and each of $R^a$ and $R^b$ is hydrogen, or each of $R^a$ and $R^b$ is independently (1-3C) normal alkyl, or $R^a$ is hydrogen and $R^b$ is (1-3C)alkyl or formyl, or $NR^aR^b$ is 1-pyrrolidinyl or 4-morpholinyl;

b) Q is —CH($CH_3$)—, —C($CH_3$)$_2$— or —CH(OH)—; each of i and j is 1; and each of $R^a$ and $R^b$ is hydrogen, or each of $R^a$ and $R^b$ is independently (1-3C) normal alkyl, or $R^a$ is hydrogen and $R^b$ is (1-3C)alkyl or formyl, or —$NR^aR^b$ is 1-pyrrolidinyl or 4-morpholinyl;

c) Q is cyclohexane-1,4-diyl; each of i and j is 0; $R^a$ is hydrogen; and $R^b$ is hydrogen or methyl;

d) Q is —$CHR^c$—; i is 0; j is 1; $R^a$ is hydrogen or methyl; and $R^b$ and $R^c$ together are —$(CH_2)_k$— wherein k is 2 or 3;

e) Q is —$CHR^c$—; i is 1; j is 1; $R^a$ is hydrogen or methyl; and $R^b$ and $R^c$ together are —$(CH_2)_k$— wherein k is 1, 2 or 3; or f) Q is —$CHR^c$—; i is 0 or 1; j is 2; $R^a$ is hydrogen or methyl; and $R^b$ and $R^c$ together are —$(CH_2)_k$— wherein k is 2; and $R^2$ is fluoro, chloro, (1-4C)alkyl, —$NR^dR^e$, —$OR^f$, acetyl, —$CONR^gR^h$ or $NHCOR^i$ in which each of $R^d$ and $R^e$ is independently hydrogen or (1-3C)alkyl; or —$NR^dR^e$ is 1-pyrrolidinyl, 1-piperidinyl, 1-piperazinyl, hexahydro-1,4-diazepin-1-yl or 4-morpholinyl (in which the 1-piperazinyl or hexahydro-1,4-diazepin-1-yl may bear a 4-methyl substituent and the 1-piperidinyl may bear one or two 4-methyl substituents); $R^f$ is (1-3C)alkyl, 2-fluoroethyl, 2,2,2-trifluoroethyl or 2-methoxyethyl; each of $R^g$ and $R^h$ is hydrogen, or $R^g$ is hydrogen and $R^h$ is (1-6C)alkyl or (3-6C)cycloalkyl, or each of $R^g$ and $R^h$ is independently (1-3C)alkyl, or —$NR^gR^h$ is 1-pyrrolidinyl, 1-piperidinyl, 1-piperazinyl or 4-morpholinyl (in which the 1-piperazinyl may bear a 4-methyl substituent and the 1-piperidinyl may bear one or two 4-methyl substituents); and $R^i$ is hydrogen, (1-6C)alkyl or (3-6C)cycloalkyl.

As used herein, the expression a compound of formula I or the expression a compound of the invention includes the compound and any conventional prodrug thereof, as well as a pharmaceutically acceptable salt of said compound or prodrug.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

Particular values for the groups and ranges defined herein include the following: (1-3C) normal alkyl is methyl, ethyl or propyl; (1-3C)alkyl is methyl, ethyl, propyl, or isopropyl; (1-4C)alkyl is methyl, ethyl, propyl, isopropyl, butyl, isobutyl, sec-butyl or tert-butyl; (1-6C)alkyl is methyl, ethyl, propyl, isopropyl, butyl, isobutyl, sec-butyl tert-butyl; pentyl, 3-methylbutyl, 1-ethylpropyl, hexyl, 4-methylpentyl or 2-ethylbutyl; and (3-6C)cycloalkyl is cyclohexyl, cyclobutyl, cyclopentyl or cyclohexyl.

It will be appreciated that certain compounds of formula I (or salts or prodrugs, etc.) may, exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin and/or factor Xa, it being well known in the art how to prepare or isolate particular forms and how to determine inhibitory properties against thrombin and/or factor xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

A prodrug of a compound of formula I may be one formed in a conventional manner with a functional group of the compound, such as with an amino, hydroxy or carboxy group.

One particular compound of formula I is one wherein

R is 2-pyridinyl, which bears a methyl, fluoro or chloro substituent at the 5-position; or R is 2-thiazolyl, which may bear a methyl substituent at the 4-position or a bromo substituent at the 5-position, or R is phenyl, which may bear a fluoro, chloro or methoxy substituent at the 4-position; or R is 6-indolyl;

$R^1$ is 2-aminoethyl, 2-(dimethylamino)ethyl, 2-(formylamino) ethyl, 3-aminopropyl, 3-(formylamino)propyl, 3-(1-pyrrolidinyl)propyl, 3-(4-morpholinyl)propyl, 3-amino-2-methylpropyl, 3-amino-2,2-dimethylpropyl, 3-amino-2-hydroxypropyl, cis-4-aminocyclohexyl, cis-4-(methylamino)-cyclohexyl, 3-pyrrolidinyl, 3-piperidinyl, 3-azetidinyl-methyl, 3-pyrrolidinylmethyl, 3-piperidinylmethyl, 4-piperidinyl, 4-piperidinylmethyl or 1-methyl-piperidin-4-yl; and $R^2$ is fluoro, isopropyl, tert-butyl, dimethylamino, 1-pyrrolidinyl, 1-piperidinyl, 1-piperazinyl, hexahydro-1,4-diazepin-1-yl, 4-morpholinyl, methoxy, ethoxy, 2-fluoroethoxy, 2,2,2-trifluoroethoxy, 2-methoxyethoxy or acetyl.

A more particular compound, or salt thereof, as described above is one wherein

R is 5-chloropyridin-2-yl, 2-thiazolyl, 4-methylthiazol-2-yl, 5-bromothiazol-2-yl or 4-chlorophenyl;

$R^1$ is 2-aminoethyl, 2-(formylamino)ethyl, 3-amino-propyl, 3-(formylamino)propyl, 3-amino-2,2-dimethylpropyl, cis-4-aminocyclohexyl, 3-piperidinylmethyl or 4-piperidinyl; and $R^2$ is fluoro, isopropyl, tert-butyl, dimethylamino, 1-pyrrolidinyl, 4-morpholinyl, 2-fluoroethoxy, 2,2,2-trifluoroethoxy, 2-methoxyethoxy or acetyl.

A preferred compound, or salt thereof, as described above is one wherein for R, $R^1$ and $R^2$:

R is 5-chloropyridin-2-yl;

$R^1$ is 3-amino-2,2-dimethylpropyl, cis-4-amino-cyclohexyl, or 4-piperidinyl; and $R^2$ is 1-pyrrolidinyl, 4-morpholinyl, 2-fluoroethoxy or 2-methoxyethoxy.

One compound according to the above definitions is a pyridine in wherein one of $A^3$, $A^4$, $A^5$ and $A^6$ is N, and each of the others is $CR^3$, $CR^4$, $CR^5$ or $CR^6$, respectively; in which each of $R^3$, $R^4$ and $R^6$ is hydrogen and $R^5$ is hydrogen or methyl, and, more particularly, wherein each of $R^3$, $R^4$, $R^5$ and $R^6$ is hydrogen.

One pyridine according to the above definitions is one wherein $A^3$ is N.

Another pyridine according to the above definitions is one wherein $A^4$ is N.

A further pyridine according to the above definitions is one wherein $A^5$ is N.

Another pyridine according to the above definitions is one wherein $A^6$ is N.

Another particular compound or salt according to the above definitions is one wherein $A^3$, $A^4$, $A^5$ and $A^6$, together with the two carbons to which they are attached, complete a substituted thiophene ring in which (a) $A^3$ and $A^6$ are each CH; or (b) $A^3$ and $A^4$ are each CH.

A particular compound or salt according to the above definitions is one wherein L is carbonyl.

Another particular compound or salt according to the above definitions is one wherein L is methylene.

A specific compound, or pharmaceutically acceptable salt thereof, is any one of those provided in the Examples, particularly the compound provided in one of Examples 12, 25 and 29, or a pharmaceutically acceptable salt thereof.

A pharmaceutically acceptable salt of a compound of the instant invention is an acid-addition salt made from a basic compound of formula I and an acid which provides a pharmaceutically acceptable anion.

As an additional aspect of the invention there is provided a pharmaceutical composition comprising in association with a pharmaceutically acceptable carrier, diluent or excipient, a compound of formula I, or a pharmaceutically acceptable salt thereof, as provided in any of the descriptions herein.

Further, there is provided a pharmaceutical composition for treating a thromboembolic disorder containing as an active ingredient a compound of formula I, or a pharmaceutically acceptable salt thereof, as provided in any of the descriptions herein.

In addition, there is provided the use of a compound of formula I, or a pharmaceutically acceptable salt thereof, as described herein as an active ingredient in the manufacture of a medicament for use in producing an anticoagulant or antithrombotic effect.

The present invention also provides a method of inhibiting coagulation in a mammal, particularly a human, comprising administering to a mammal in need of treatment, a coagulation inhibiting dose of a compound of formula I, or a pharmaceutically acceptable salt thereof, having any of the definitions herein.

The present invention further provides a method of inhibiting thrombin and/or factor Xa comprising administering to a mammal, particularly a human, in need of treatment, a thrombin and/or factor Xa inhibiting dose of compound of formula I having any of the definitions herein.

Further, the present invention provides a method of treating a thromboembolic disorder comprising administering to a mammal, particularly a human, in need of treatment, an effective dose of a compound of formula I, or a pharmaceutically acceptable salt thereof, having any of the definitions herein.

Also, there is provided a compound of formula I, or a pharmaceutically acceptable salt thereof, having any of the definitions herein for use as an antithrombotic agent.

In addition, there is provided the use of a compound of formula I, or a pharmaceutically acceptable salt thereof, having any of the definitions herein for the manufacture of a medicament for treatment of a thromboembolic disorder.

A compound of formula I may be prepared by processes which include processes known in the chemical art for the production of structurally analogous compounds or by a novel process described herein. A novel process described herein provides another aspect of the invention. A process for the preparation of a compound of formula I (or a pharmaceutically acceptable salt thereof) and novel intermediates for the manufacture of a compound of formula I provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a compound of formula I, or a pharmaceutically acceptable salt thereof, as provided in any of the above descriptions, comprising the step selected from (A) for a compound in which L is carbonyl, acylating an amine of formula II,

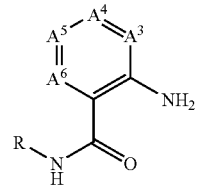

II using an acid of formula III (in which $R^a$ as hydrogen may be replaced by a nitrogen protecting group $R^p$),

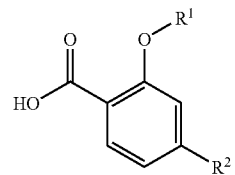

III or an activated derivative thereof;

(B) acylating an amine of formula R—NH$_2$ using an acid of formula IV (in which $R^a$ as hydrogen may be replaced by a nitrogen protecting group $R^p$),

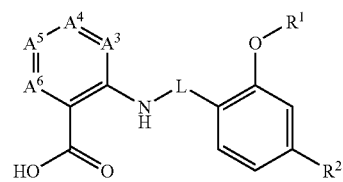

IV or an activated derivative thereof;

(C) for a compound of formula I in which L is methylene, substituting the group $Y^a$ of a compound of formula VI

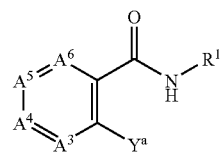

VI in which $Y^a$ is a leaving group for nucleophilic aromatic substitution with an amine of formula VII

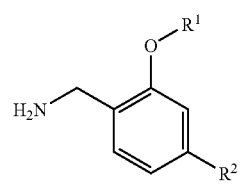

VII (in which R$^a$ as hydrogen may be replaced by a nitrogen protecting group R$^p$); or alkylating an amine of formula II directly, using a compound of formula VIII,

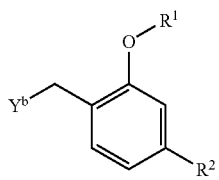

VIII (in which R$^a$ as hydrogen may be replaced by a nitrogen protecting group R$^p$) in which Y$^b$ is a leaving group for nucleophilic substitution, or indirectly, by reductive alkylation using an aldehyde of formula IX;

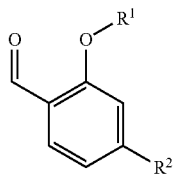

IX (in which R$^a$ as hydrogen may be replaced by a nitrogen protecting group R$^p$);

(D) for a compound of formula I in which each of R$^a$ and R$^b$ is (1-3C) normal alkyl, or R$^a$ is hydrogen and R$^b$ is methyl or (1-3C)alkyl, or NR$^a$R$^b$ is 1-pyrrolidinyl or 4-morpholinyl, alkylating a corresponding compound of formula I in which each of R$^a$ and R$^b$ is hydrogen;

(E) for a compound of formula I in which R$^a$ is methyl or (1-3C) normal alkyl, alkylating a corresponding compound of formula I in which R$^a$ is hydrogen;

(F) for a compound of formula I in which R$^b$ is formyl, formylating a corresponding compound of formula I in which R$^b$ is hydrogen;

(G) alkylating the phenolic oxygen of a compound of formula X,

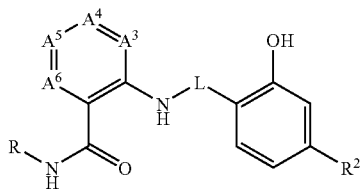

X using a corresponding compound of formula XI (in which R$^a$ as hydrogen may be replaced by a nitrogen protecting group R$^p$),

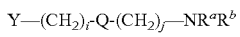

XI

Y—(CH$_2$)$_i$-Q-(CH$_2$)$_j$—NR$^a$R$^b$ wherein Y is a conventional leaving group for nucleophilic substitution and wherein, for a compound of formula I in which i is 0, the stereochemistry of the carbon to which Y is attached is inverted from that of the product;

(H) for a compound of formula I in which L is carbonyl and R$^2$ is —NR$^d$R$^e$ or —OR$^f$ and L is carbonyl, substitution of the group Y$^c$ of a compound of formula XII

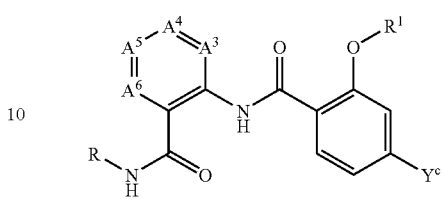

XII (in which R$^a$ as hydrogen may be replaced by a nitrogen protecting group R$^p$), wherein Y$^c$ is a leaving group for nucleophilic aromatic substitution, using H—NR$^d$R$^e$ or H—OR$^f$ or the deprotonated form thereof; and (I) for a compound of formula I in which R$^2$ is —OR$^f$, alkylating the phenolic oxygen of a compound of formula XIII (in which R$^a$ as hydrogen may be replaced by a nitrogen protecting group R$^p$),

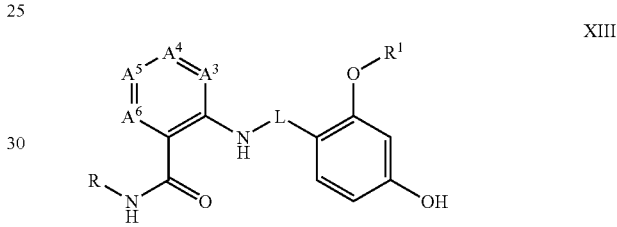

XIII using a corresponding compound of formula Y—R$^f$ in which Y is a conventional leaving group for nucleophilic substitution;

whereafter, for any of the above procedures, when a functional group is protected using a protecting group, removing the protecting group;

whereafter, for any of the above procedures, when a pharmaceutically acceptable salt of a compound of formula I is required, it is obtained by reacting the basic form of a basic compound of formula I with an acid affording a physiologically acceptable counterion or by any other conventional procedure;

and wherein, unless otherwise specified above in this claim, A$^3$-A$^6$, L, R, R$^1$, R$^2$, Q, R$^a$-R$^i$, i, j and k have any of the values defined hereinabove.

For a carboxylic acid herein, a typical activated derivative includes an ester (particularly a lower alkyl ester such as the methyl or ethyl ester), an acid halide (particularly the acid chloride), and an activated ester or anhydride (including the 4-nitrophenyl ester and an activated ester or anhydride derived from a coupling reagent).

As used herein, a leaving group "Y$^a$" or "Y$^c$" is a moiety which is displaced in an aromatic (or heteroaromatic) nucleophilic substitution reaction, for example a halo group (such as fluoro or chloro), an alkoxy group (such as methoxy), or a sulfonate ester group (such as methylsulfonyloxy, p-toluylsulfonyloxy or trifluoromethylsulfonyloxy). The substitution may be carried out by heating a mixture of the reagents, for example as described at Example 1-G or Example 3-A, optionally in a polar solvent, and optionally in the presence of a base, such as triethylamine, for example in ethanol in a sealed tube as described at Example 22-E.

As used herein, a leaving group "$Y^b$" is a moiety which is displaced in a nucleophilic substitution reaction, for example a halo group (such as chloro, bromo or iodo), a sulfonate ester group (such as methylsulfonyloxy, p-toluyl-sulfonyloxy or trifluoromethylsulfonyloxy), or the reactive species derived from treating an alcohol with triphenyl-phospine, diethyl azodicarboxylate and triethyl amine (in a Mitsunobu reaction).

A preferred method of formylating the nitrogen of a compound in which $R^b$ is hydrogen is the use of a formylating reagent such as formic acetic anhydride.

As used herein, a leaving group "Y" is a moiety which is displaced in a nucleophilic substitution reaction, for example a halo group (such as bromo or iodo), a sulfonate ester group (such as methylsulfonyloxy, p-toluylsulfonyloxy or trifluoromethylsulfonyloxy), or the reactive species derived from treating an alcohol with triphenylphospine, diethyl azodicarboxylate and triethyl amine (in a Mitsunobu reaction). In addition, for the preparation of a compound in which Q is —CH(OH)—, the group Y—$CH_2$-Q- may represent an epoxy group. The substitution may be carried out, for example as described at Example 1-F, Example 5-A, Example 6-D, Example 23-F or Example 26-B, as well as at Example 26-A, Example 31-A and Example 32-A.

If not commercially available, a necessary starting material for the preparation of a compound of formula I may be prepared by a novel process described herein or one analogous thereto or by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. A novel intermediate or starting material compound provides a further aspect of the invention.

Selective methods of substitution, protection and deprotection are well known in the art for preparation of a compound such as one of formulae II-XIII.

Thus, one particular intermediate is an acid of formula III, or a salt thereof, or an activated derivative thereof, (in which $R^a$ as hydrogen may be replaced by a nitrogen protecting group $R^p$),

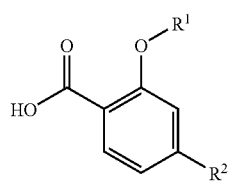

III wherein $R^1$ and $R^2$ have any of the values defined herein above. Conveniently, the salt of a carboxylic acid herein may be the sodium or potassium salt.

Another aspect is an acid of formula IV (in which $R^a$ as hydrogen may be replaced by a nitrogen protecting group $R^p$),

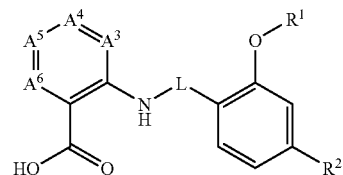

IV or an activated derivative thereof, wherein $A^3$-$A^6$, L, $R^1$ and $R^2$ have any of the values defined herein. In addition, for an acid of formula IV, in which L is carbonyl, a particular activated derivative is a compound of formula V,

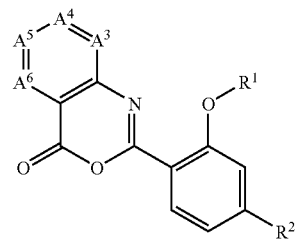

V or a salt of the active derivative, in which $A^3$-$A^6$, $R^1$ and $R^2$ have any of the values defined herein, or a derivative thereof in which a functional group other than the activated derivative of the carboxy group is protected using a protecting group. Further, for an acid of formula IV, in which L is methylene, a particular activated derivative is a compound of formula Va,

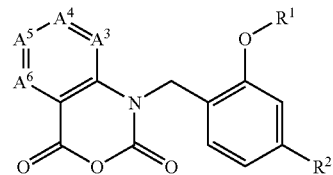

Va or a salt of the active derivative, in which $A^3$-$A^6$, $R^1$ and $R^2$ have any of the values defined herein, or a derivative thereof in which a functional group other than the activated derivative of the carboxy group is protected using a protecting group.

An additional intermediate, beyond a compound of formula I in which $R^2$ is chloro or fluoro, is a compound of formula XII

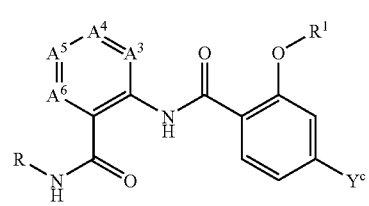

XII (in which $R^a$ as hydrogen may be replaced by a nitrogen protecting group $R^p$), wherein $Y^c$ is a leaving group for nucleophilic aromatic substitution other than fluoro or chloro and $A^3$-$A^6$, R and $R^1$ have any of the values defined hereinabove.

A further intermediate is a compound of formula XIII

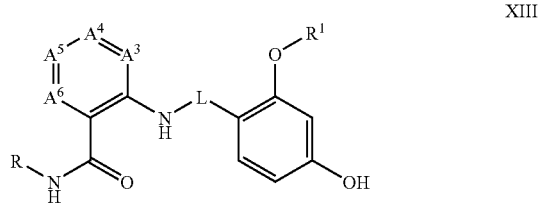

XIII (in which $R^a$ as hydrogen may be replaced by a nitrogen protecting group $R^p$), wherein $A^3$-$A^6$, L, R and $R^1$ have any of the values defined hereinabove.

As an another aspect of the invention there is provided compound of formula I as disclosed herein but in which $R^a$ as hydrogen is replaced by a nitrogen protecting group $R^p$, and wherein $A^3$-$A^6$, L, R, $R^1$ and $R^2$, otherwise, have any of the values defined herein.

As a further aspect of the invention, there is provided the use of a compound (or activated and/or protected derivative thereof or salt of the compound or derivative) of formula III or VI as a starting material in the preparation of an inhibitor of thrombin and/or factor Xa.

As mentioned above, the invention includes a pharmaceutically acceptable salt of the thrombin and/or factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt.

Generally, a basic compound of the invention is isolated best in the form of an acid addition salt. A salt of a compound of formula I formed with an acid such as mentioned above is useful as a pharmaceutically acceptable salt for administration of the antithrombotic agent and for preparation of a pharmaceutical composition of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors.

The compounds of the invention are believed to selectively inhibit thrombin and/or factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin and/or factor Xa in a mammal comprising administering to a mammal in need of treatment an effective (thrombin and/or factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The thrombin and/or factor Xa inhibition, coagulation inhibition and thromboembolic disorder treatment contemplated by the present method includes both medical therapeutic and/or prophylactic treatment as appropriate.

In a further embodiment, the invention relates to treatment, in a human or animal, of a condition where inhibition of thrombin and/or factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs, including joint replacement, and cardiac valves. Further, the compounds have expected utility in anticoagulant treatment in hemodialysis and disseminated intravascular coagulation. Further, the compounds may be useful in reducing the increased thrombin generation which occurs in the airways of patients with asthma; see, E. C. Gabazza, et al., Lung, (1999), 177(4), 253-262. A further expected utility is in rinsing or coating of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises a compound of formula I, or a pharmaceutically acceptable salt thereof, in association with a pharmaceutically acceptable carrier, diluent or excipient.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art.

The ability of a compound of the present invention to be an effective and orally active thrombin and/or factor Xa inhibitor may be evaluated in one or more of the following assays or in other standard assays known to those in the art.

The inhibition by a compound of the invention of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265-300. The inhibitor binding affinity is measured as apparent association constant Kass which is the hypothetical equilibrium constant for the reaction between enzyme and the test inhibitor compound (I).

$$K_{ass} = \frac{[Enzyme\text{-}I]}{([Enzyme] \times [I])}$$

Conveniently, enzyme inhibition kinetics are performed in a high-volume protocol using automated dilutions of inhibitors (n=3 for each of four to eight inhibitor concentrations) into 96-well polystyrene plates and reaction rates are determined from the rate of hydrolysis of appropriate p-nitroanilide substrates at 405 nm using a Thermomax plate reader from Molecular Devices (San Francisco, Calif.). The same general protocol is followed for all enzymes studied: In each well is placed 50 μL buffer (0.06 M Tris, 0.3 M NaCl, pH 7.4), followed by 25 μL of inhibitor solution (in 100% methanol) and 25 μL enzyme solution (e.g., human factor Xa, 32 nM in 0.03 M Tris, 0.15 M NaCl, 1 mg/mL HAS); finally, within two minutes, 150 μL aqueous solution of chromogenic substrate (e.g., 0.3 mM BzIle-Glu-Gly-Arg-pNA) is added to start the enzymatic reaction. Final factor Xa concentration is 3.2 nM. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, human factor Xa is used to hydrolyze BzIle-Glu-Gly-Arg-pNA; 5.9 nM human thrombin is used to hydrolyze 0.2 mM BzPhe-Val-Arg-pNA; 3.4 nM human plasmin is used with 0.5 mM HD-Val-Leu-Lys-pNA; 1.2 nM human nt-PA is used with 0.8 mM HD-Ile-Pro-Arg-pNA; and 0.4 nM urokinase is used with 0.4 mM pyro-Glu-Gly-Arg-pNA.

Kass is calculated for a range of concentrations of test compounds which produce hydrolysis inhibition of between 20% and 80% of control and the mean value reported in units of liter per mole. In general, a compound of formula I of the instant invention, as exemplified hereinbelow in the working examples, exhibits a Kass for factor Xa of $0.1\text{-}1{,}000 \times 10^6$ L/mole or greater. Most of the examples also exhibit a Kass for thrombin (factor IIa) of $0.3\text{-}100 \times 10^6$ L/mole or greater. Examples in which L is carbonyl and R, $R^1$ and $R^2$ are the preferred values described above exhibit a Kass for factor Xa of $40 \times 10^6$ L/mole or greater and a Kass for thrombin (factor IIa) of $4 \times 10^6$ L/mole or greater.

The thrombin and/or factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.*, 185, 1-11 (1980; and Smith, et al., *Biochemistry*, 11, 2958-2967, (1972). Human fibrinogen (98 percent pure/plasmin free) is from American Diagnostica, Greenwich, Conn.

Radiolabeling of fibrinogen 1-2 preparations is performed as previously reported. Smith, et al., *Biochemistry,* 11, 2958-2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction 1-2 according to previous procedures and specifications. Smith, *Biochem. J.,* 185, 1-11 (1980); and Smith, et al., *Biochemistry,* 11, 2958-2967 (1972). Human fibrinogen is also purchased as 98 percent pure/plasmin free from American Diagnostica, Greenwich, Connecticut. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research,* 50, 163-174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. Thus, the plasma concentrations are three times the assay concentrations. The compounds of formula I are added to human or animal plasma over a wide range of concentrations to determine prolongation effects on the APTT, PT, and TT assays. Linear extrapolations are performed to estimate the concentrations required to double the clotting time for each assay. Compounds of the instant invention potently extended the prolongation times in the APTT and PT assays, for example in some cases, with assay concentrations necessary to double the APPT or PT of less than 1 μM.

Animals

Male Sprague Dawley rats (350-425 gm, Harlan Sprague Dawley Inc., Indianapolis, Ind.) are anesthetized with xylazine (20 mg/kg, s.c.) and ketamine (120 mg/kg, s.c.) or preferably are anesthetized using isoflurane anesthesia (2-3%, conveniently 2.5%, for surgery; 1.5-2.5%, conveniently 2.5%, for maintenance; flow rate kept at 0.5% throughout) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol,* 77:29, 1982).

$FeCl_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 μL is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.,* 60:269, 1990).

Ex Vivo Coagulation Parameters

Ex vivo plasma thrombin time (TT), prothrombin time (PT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with isotonic saline (0.1 mL) and bovine thrombin (0.1 mL, 30 U/mL in TRIS buffer; Parke Davis) at 37° C. For PT, to plasma (0.1 mL) mixed with isotonic saline (0.1 mL) is added PT reagent (0.1 mL, Dade, Thromboplastin-C); and the fibrometer started immediately after the addition of the final reagent. For APTT, plasma (0.1 mL) and APTT solution (0.1 mL, Organon Teknika) are incubated for 5 minutes (37° C.); and $CaCl_2$ (0.1 mL, 0.025 M) is added to start coagulation. Assays are done in duplicate and averaged.

Index of Bioavailability

Bioavailability studies may be conducted as follows. Compounds are administered as aqueous solutions, or as solutions in 5% PEG 200, to male Fisher rats, intravenously (iv) at 5 mg/kg via tail vein injection and orally (po) as aqueous solutions, or as a suspension in 5% acacia, to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varian) cartridges for sample preparation and a methanol/30 nM ammonium acetate buffer (pH 4) gradient optimized for each compound. % Oral bioavailability is calculated by the following equation:

$$\% \text{ Oral bioavailability} = \frac{AUC\ po}{AUC\ iv} \times \frac{\text{Dose } iv}{\text{Dose } po} \times 100$$

where AUC is area under the curve calculated from the plasma level of compound over the time course of the experiment following oral (AUC po) and intravenous (AUC iv) dosing.

Compounds

For oral determinations, the compound may be administered orally, by gavage, as a suspension in 5% acaia to conscious fasted rats. The pretreatment time before flow is established through the shunt is selected based upon the peak apparent plasma concentration recorded in preliminary time course experiments that track apparent drug concentration in plasma following oral administration to conscious fasted rats, and typically varies between 1 to 5 hours. Animals used in antithrombotic efficacy experiments are anesthetized as described 15 minutes before the predetermined pretreatment time to allow for surgical preparation of the animals. Compound solutions are prepared fresh daily in normal saline or in 5% PEG200 in water for iv determinations and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Typically, bolus injection volume is 1 mL/kg for iv, and 5 mL/kg for po, and infusion volume is 3 mL/h. For a similar procedure run in the anesthesized rabbit, for example an infusion rate of 6.8 mL/h was used for one compound infused in 5% PEG200 in water.

Statistics

Results are expressed as means +/−SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months-2 years; 12-13 kg, Marshall Farms, North Rose, New York 14516) are fasted overnight and fed Purina certified Prescription Diet (Purina Mills, St. Louis, Mo.) 240 minutes after dosing. Water is available ad libitum. The room temperature is maintained between 66-74° F.; 45-50 percent relative humidity; and lighted from 0600-1800 hours.

Pharmacokinetic Model.

Test compound is formulated immediately prior to dosing by making a suspension in a "wet granulaion" (povidone, 0.85 mg/mL; lactose, 15.0 mg/mL; and polysorbate 80, 65 µL in 250 mL water). Dogs are given a single 20 mg/kg (in 25 mL of wet granulation) dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Male dogs (Beagles, as described above) are fasted overnight and dosed with test compound that is fomulated immediately prior to'dosing by making a suspension in a "wet granulation" as described above. Dogs are given a single dose of 5, 10 or 20 mg/kg (in 25 mL of wet granulation) of test compound by oral gavage. Based on the pharmacokinetics of the test compound, dogs are dosed either 1 or 2 hours prior to anesthesia. Dogs are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3-4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40-50 percent inhibition of the hyperemic blood flow response observed after 10-s mechanical occlusion of the LCX. All hemodynamic and ECG measurements are recorded and analyzed with a data acquisition system (Notochord HEM data analysis system, Croissy, France).

Thrombus Formation and Compound Administration Regimens

Electrolytic injury of the intima of the LCX is produced by applying 100-µA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment for a minimum of 30 minutes). The preparation is followed for 4 hours at which time the animal is euthanized and the thrombus is dissected from the LCX and weighed.

Hematology, Coagulation and Template Bleeding Time Determinations

Citrated blood (3 mL, 1 part 3.8% citrate: 9 parts blood) is drawn before drug administration, at 60 min after administration, at 60 min after initiation of vessel injury and just prior to the end of the experiment. Whole blood cell counts, hemoglobin, and hematocrit values are determined on a 40-µL sample of the citrated whole blood with a hematology analyzer (Cell-Dyn 900, Sequoia-Turner, Mount View, Calif., U.S.A.). The remaining blood was cetrifuged at 3,000 g for 5 min to prepare cell-free plasma. Plasma clotting times, prothrombin time (PT) and activated partial thromboplastin times (APTT) were performed using standard Dade reagents and the Coa-Screener coagulation device (American Labor, Largo, Fla.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Dunnet's post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, (1993), 21, 587-599.

Compounds of the instant invention are potent anticoagulant and antithrombotic agents which exhibit particularly good plasma exposure following oral administration, as well as desirable volume of distribution and tissue selectivity properties, as evidenced by standard pharmacokinetic/pharmcodynamic and brain flux assays.

The following Examples are provided to further describe the invention and are not to be construed as limitations thereof.

The abbreviations, symbols and terms used in the examples and preparations have the following meanings.

Ac=acetyl
Analysis=elemental analysis
aq=aqueous
Boc=t-butyloxycarbonyl
t-Bu=tert-butyl
Calcd=calculated
conc=concentrated
DMF=dimethylformamide
DMSO=dimethylsulfoxide
EtOAc=ethyl acetate
HOAc=acetic acid
EtOH=ethanol
MeOH=methanol
TFA=trifluoroacetic acid
THF=tetrahydrofuran
HPLC=High Performance Liquid Chromatography
IR=Infrared Spectrum
$^1$NMR=(proton) nuclear magnetic resonance spectrum
ES-MS=electron spray mass spectrum
IS-MS=ion spray mass spectrum
FD-MS=field desorption mass spectrum When indicated without data, $^1$NMR, IR or MS means a satisfactory spectrum was obtained.

EXAMPLE 1

Preparation of N-(4-Chlorophenyl)-3-[2-(piperidin-4-yloxy)-4-(pyrrolidin-1-yl)benzoylamino]pyridine-4-carboxamide

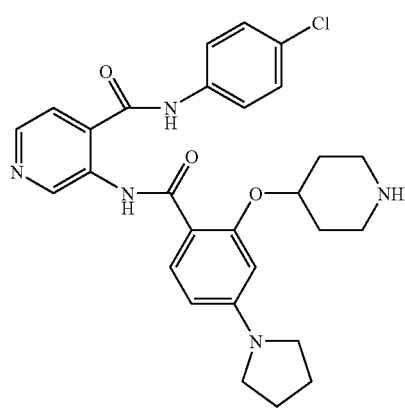

A. 3-tert-Butoxycarbonylaminopyridine

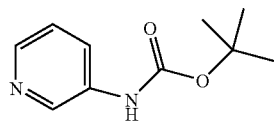

3-Aminopyridine (4.29 g, 45.6 mmol) was dissolved in THF (100 mL). A 1 M THF solution of sodium hexamethyldisilazide (NaHMDS, 100 mL, 100 mmol) was added dropwise via an addition funnel. After 15 min, a solution of di-t-butyl dicarbonate [(Boc)$_2$O] (11.92 g, 54.6 mmol) in THF (100 mL) was added dropwise. After 15 min, the reaction was quenched with water (100 mL) and extracted with EtOAc (500 mL). The organic layer was washed with water (2×100 mL). The aqueous layers were combined and extracted with EtOAc (200 mL). The organic layers were combined, dried over sodium sulfate, filtered, and concentrated. The crude material was purified by flash column chromatography (30% EtOAc/CH$_2$Cl$_2$) to give the desired product (5.195 g, 30.5 mmol, 67%) as an orange solid.

$^1$NMR (400 MHz, DMSO-d$_6$): δ 9.53(s, 1H); 8.57(s, 1H); 8.14(d, J=4.4 Hz, 1H); 7.84(d, J=8.0 Hz, 1H); 7.25(m, 1H); 1.44(s, 9H).

IS-MS, m/e 195.3 (m+1).

Analysis for C$_{10}$H$_{14}$N$_2$O$_2$:

Calcd: C, 61.84; H, 7.27; N, 14.42;

Found: C, 61.94; H, 7.18; N, 14.38.

B. 3-(N-tert-Butoxycarbonylamino)-N-(4-chlorophenyl)-pyridine-4-carboxamide

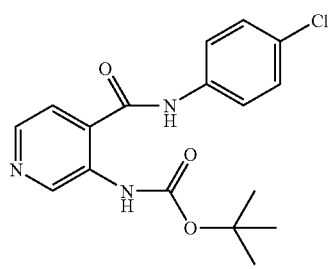

The 3-tert-butoxycarbonylaminopyridine (2.0035 g, 10.32 mmol) was dissolved in THF (100 mL). The solution was cooled to −30° C. in a dry ice/acetonitrile bath, then t-BuLi (13 mL, 22.1 mmol) was added dropwise. After 1 h, 4-chlorophenyl isocyanate (1.911 g, 12.44 mmol) was added. The reaction mixture was warmed to 0° C. After 1.5 h, the reaction was warmed to room temperature. After 3 h at room temperature, the reaction was quenched with water (100 mL) and extracted with EtOAc (800 mL). The organic layer was washed with water (2×50 mL), dried over sodium sulfate, filtered, and concentrated. The crude material was purified by flash column chromatography (350 g silica, 30% EtOAc/-CH$_2$Cl$_2$) to give the amide (1.284 g, 3.69 mmol, 36%) as a pale yellow solid.

¹NMR (400 MHz, DMSO-d₆): δ 10.61(s, 1H); 9.48(s, 1H); 8.93(s, 1H); 8.39(d, J=5.2 Hz, 1H); 7.71(d, J=8.8 Hz, 1H); 7.59(d, J=5.2 Hz, 1H); 7.39(d, J=9.2 Hz, 2H); 1.37(s, 9H).

IS-MS, m/e 348.2 (m+1).

C. 3-Amino-N-(4-chlorophenyl)pyridine-4-carboxamide

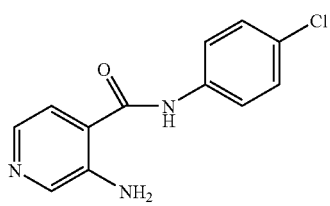

To 3-(N-tert-butoxycarbonylamino)-N-(4-chlorophenyl)-pyridine-4-carboxamide (552 mg, 1.59 mmol) was added trifluoroacetic acid (3 mL, 38.95 mmol). After stirring for 10 min, the reaction mixture was concentrated, diluted with CH₂Cl₂, washed with satd Na₂CO₃, dried (Na₂SO₄) and concentrated to give the title compound (367 mg, 93%) as a pale yellow solid.

¹NMR (300 MHz, DMSO-d₆): δ 10.31(s, 1H); 8.14(s, 1H); 7.78(d, J=6.8 Hz, 1H); 7.71(d, J=12.0 Hz, 2H); 7.46(d, J=6.8 Hz, 1H); 7.37(d, J=12.0 Hz, 2H); 6.34(s, 2H).

IS-MS, m/e 248.3 (m+1).

Analysis for $C_{12}H_{10}ClN_3O$:

Calc: C, 58.19; H, 4.07; N, 16.97;

Found: C, 58.30; H, 4.30; N, 16.80.

D. 1-Boc-4-hydroxypiperidine

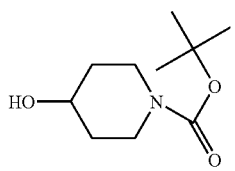

To a mixture of 4-hydroxypiperidine (60.69 g, 0.6 mol), 4-(dimethylamino)pyridine (74 mg, 0.6 mmol), CH₂Cl₂ (150 mL), and THF (150 mL) was added di-t-butyl dicarbonate [(Boc)₂O] (130.95 g, 0.6 mol). After stirring for 6 h, the reaction mixture was heated to 35° C. for 16 h. More (Boc)₂O (13.09 g, 0.06 mol) in THP (20 mL) was added, and the mixture was heated for 10 h. After cooling, water and ether (1 L) were added and the mixture was stirred for 2 h. The organic layer was partitioned, dried (MgSO₄), and concentrated in vacuo. The residue was crystallized from ether to give the product as a white solid (105 g, 87%).

¹NMR (300 MHz, DMSO-d₆): δ 3.85 (m, 3H), 3.04 (m, 2H), 1.88 (m, 2H), 1.56 (m, 2H), 1.25 (s, 9H).

IS-MS, m/e: 202.0 (m+1).

E. Methyl 4-Fluoro-2-hydroxybenzoate

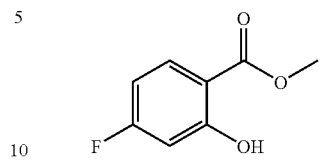

i. 4-Fluoro-2-hydroxybenzoic Acid

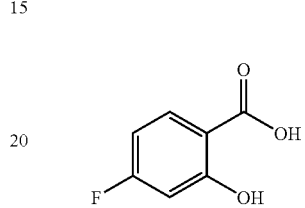

Potassium carbonate (51.6 g, 373 mmol) was dried by heating at 200° C. for 12 h. This was treated with 3-fluorophenol (16.5 g, 147 mmol) in a sealed container which was then pressurized with carbon monoxide to 61.2 bar (900 psig). The reaction mixture was heated to 175° C. for 5 h. Subsequently, the reaction mixture was dissolved in water, acidified with concentrated hydrochloric acid, and filtered. The solid was washed with water, then hexanes. The solid was then dissolved in EtOAc, dried over magnesium sulfate, and concentrated to give 12 g of solid. This crude solid was purified by flash chromatography using, CHCl₃/MeOH/HOAc (98/1/1) to give 11 g of a white solid which was recrystallized from toluene to give the title compound (9.5 g, 41%) as needle solids.

¹NMR

FD-MS, m/e 155 (m−1)

Analysis for $C_7H_5OF_3.0.1\ C_7H_8.0.3\ H_2O$:

Calcd: C, 54.17; H, 3.78;

Found: C, 54.12; H, 3.39.

ii. Methyl 4-Fluoro-2-hydroxybenzoate

A solution of 4-fluoro-2-hydroxybenzoic acid (9.8 g, 62.3 mmol) in benzene (100 mL) and MeOH (20 mL) was cooled in an ice bath and a 2 M hexane solution of (trimethyl-silyl) diazomethane (50 mL) was added dropwise. The reaction was stirred overnight at ambient temperature, diluted with benzene (348 mL) and MeOH (39 mL), and treated with more of the (trimethylsilyl)diazomethane solution (15 mL). The mixture was concentrated in vacuo to dryness to give the title compound (10.4 g, 98%) as a solid.

¹NMR

FD-MS, m/e 170 (m+)

Analysis for $C_8H_7OF_3$:

Calcd: C, 56.48; H, 4.15;

Found: C, 56.17; H, 4.28.

F. Methyl 2-(1-tert-Butoxycarbonylpiperidin-4-yloxy)-4-fluorobenzoate

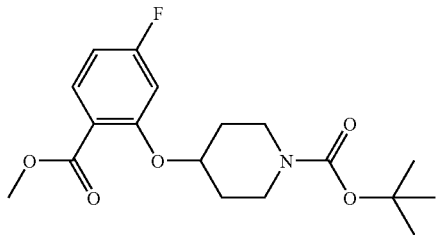

A mixture of methyl 4-fluoro-2-hydroxybenzoate (5.1 g, 30 mmol), triphenylphosphine (9.5 g, 36 mmol), 1-tert-butoxycarbonyl-4-hydroxypiperidine (6 g, 30 mmol), and benzene (10 mL) was heated until all solids dissolved. The solution was cooled to 0° C., then sonicated while adding diethyl azodicarboxylate (6.3 g, 36 mmol) dropwise. After the addition was complete, the reaction mixture was sonicated for an additional 60 min, diluted with CH$_2$Cl$_2$ (25 mL), and purified by flash chromatography, eluting with 10% EtOAc in hexanes to yield the title compound (6.45 g, 61%) as a white solid.
$^1$NMR
IS-MS, m/e 354 (m+1)
Analysis for C$_{18}$H$_{24}$FNO$_5$:
Calcd: C; 61.18; H, 6.85; N, 3.98;
Found: C, 60.98; H, 6.86; N, 4.04.

G. Methyl 2-(1-tert-Butoxycarbonylpiperidin-4-yloxy)-4-(pyrrolidin-1-yl)benzoate

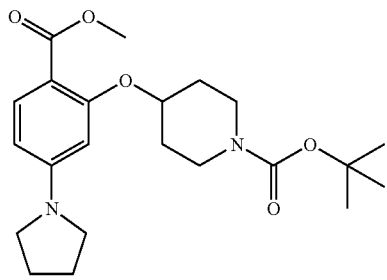

The methyl 2-(1-tert-butoxycarbonylpiperidin-4-yloxy)-4-fluorobenzoate (7.99 mmol, 22.6 mmol) was diluted with pyrrolidine (18 mL, 215.6 mmol). The resulting mixture was heated to 80° C. After 3 h, the reaction mixture was cooled to room temperature and quenched with water (50 mL). The mixture was extracted with dichloromethane (200 mL). The organic layer was washed with saturated aqueous citric acid (3×50 mL), dried over sodium sulfate, filtered, and concentrated to give the title compound (9.14 g, 100%) as a colorless oil.
$^1$NMR (400 MHz, DMSO-d$_6$): δ 7.59(d, J=9.2 Hz, 1H); 6.14(dd, J=2.2, 8.6 Hz, 1H); 6.09(s, 1H); 4.67(m, 1H); 3.65(s, 3H); 3.44-3.23(m, 8H); 1.91(s, 4H); 1.74(m, 2H); 1.64(m, 2H); 1.37 (s, 9H).
IS-MS, m/e 405.5 (m+1).
Analysis for C$_{22}$H$_{32}$N$_2$O$_5$:
Calcd: C, 65.32; H, 7.97; N, 6.93;
Found: C, 65.62; H, 8.00; N, 7.14.

H. 2-(1-tert-Butoxycarbonylpiperidin-4-yloxy)-4-(pyrrolidin-1-yl)benzoic Acid

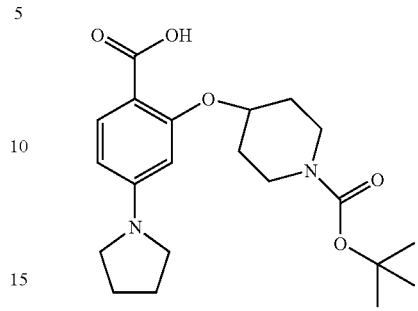

A mixture of methyl 2-(1-tert-butoxycarbonylpiperidin-4-yloxy)-4-(pyrrolidin-1-yl)benzoate (9.133 g, 22.6 mmol), 1 M LiOH (40 mL, 40 mmol), MeOH (30 mL) and THF (90 mL) was heated at 60° C. for 14 h. The reaction mixture was concentrated to one-third of its initial volume, diluted with EtOAc (700 mL), and washed with satd citric acid (3×50 mL), and water (3×50 mL) before it was dried (Na$_2$SO$_4$), filtered, and concentrated to give the title compound (6.90 g, 78%) as a white solid.
$^1$NMR (400 MHz, DMSO-d$_6$): δ 11.47(brs, 1H); 7.56(d, J=8.8 Hz, 1H); 6.11(d, J=8.4 Hz, 1H); 6.05(s, 1H); 4.64(m, 1H); 3.44-3.11(m, 8H); 1.88(m, 4H); 1.72(m, 2H); 1.60(m, 2H); 1.33(s, 9H).
IS-MS, m/e 391.3 (m+1).
Analysis for C$_{21}$H$_{30}$N$_2$O$_5$:
Calc: C, 64.60; H, 7.74; N, 7.17;
Found: C, 67.23; H, 8.13; N, 7.65.

I. 3-[2-(1-tert-Butoxycarbonylpiperidin-4-yloxy)-4-(pyrrolidin-1-yl)benzoylamino]-N-(4-chlorophenyl)pyridine-4-carboxamide

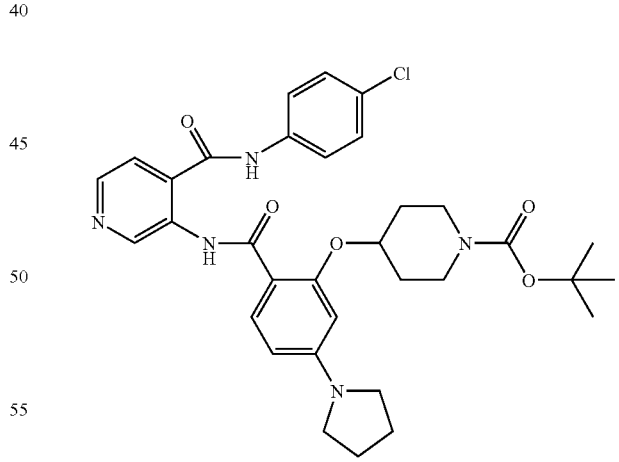

To a mixture of 2-(1-tert-butoxycarbonylpiperidin-4-yloxy)-4-(pyrrolidin-1-yl)benzoic (566 mg, 1.45 mmol), pyridine (0.15 mL, 1.85 mmol), DMF (3 drops), and CH$_2$Cl$_2$ (15 mL) was added oxalyl chloride (0.15 mL, 1.72 mmol) and the mixture was stirred for 1.5 h. The resulting 2-(1-tert-butoxycarbonylpiperidin-4-yloxy)-4-(pyrrolidin-1-yl)benzoyl chloride was concentrated and was diluted with CH$_2$Cl$_2$ (20 mL). To this mixture was added pyridine (0.15 mL, 1.85 mmol), followed by solid 3-amino-N-(4-chlorophenyl)pyridine-4-carboxamide (326 mg, 1.32 mmol). The reaction mixture was stirred for 16 h, diluted with $CH_2Cl_2$ (100 mL), washed with satd $NaHCO_3$ (2×10 mL), dried ($Na_2SO_4$), and concentrated. The resulting residue was chromatographed over silica gel (80 g; $CH_2Cl_2$ to 3% $MeOH/CH_2Cl_2$) to give the title compound (406 mg, 50%) as an off-white solid.

$^1$NMR (300 MHz, DMSO-$d_6$): δ 10.81(s, 1H); 10.63 (s, 1H); 9.47(s, 1H); 8.42(d, J=5.1 Hz, 1H); 7.76(m, 3H); 7.65(d, J=4.8 Hz, 1H); 7.39(d, J=8.7 Hz, 2H); 6.22(d, J=9.0 Hz, 1H); 6.15(s, 1H); 4.79(m, 1H); 3.74(d, J=13.2 HZ, 2H); 3.29(m, 4H); 2.98(m, 2H); 1.92(m, 8H); 1.34(s, 9H).

FD-MS, m/e 619 (m).

Analysis for $C_{33}H_{38}ClN_5O_5$:

Calc: C, 63.91; H, 6.18; N, 11.29;

Found: C, 64.12; H, 6.25; N, 11.13.

J. N-(4-Chlorophenyl)-3-[2-(piperidin-4-yloxy)-4-(pyrrolidin-1-yl)benzoylamino]pyridine-4-carboxamide Using a procedure equivalent to Example 1-C, 3-[2-(1-tert-butoxycarbonylpiperidin-4-yloxy)-4-(pyrrolidin-1-yl)benzoylamino]-N-(4-chlorophenyl)pyridine-4-carboxamide gave the title compound (132 mg, 85%) as a yellow solid.

$^1$NMR (400 MHz, DMSO-$d_6$): δ 9.52(s, 1H); 8.42(d, J=5.2 Hz, 1H); 7.76(m, 3H); 7.64(d, J=4.8 Hz, 1H); 7.40(d, J=9.2 Hz, 2H); 6.23(d, J=6.4 Hz, 1H); 6.13(s, 1H); 4.63(m, 1H); 3.28(m, 4H); 2.79(m, 2H); 2.49(m, 2H); 1.88(m, 6H); 1.65 (m, 2H).

IS-MS, m/e 520.3 (m+1).

Analysis for $C_{28}H_{30}ClN_5O_3$:

Calc: C, 64.57; H, 5.81; N, 13.47;

Found: C, 64.56; H, 5.79; N, 13.34.

EXAMPLE 2

Preparation of N-(5-Chloropyridin-2-yl)-3-[4-fluoro-2-(piperidin-4-yloxy)benzoylamino)]pyridine-2-carboxamide Trifluoroacetate

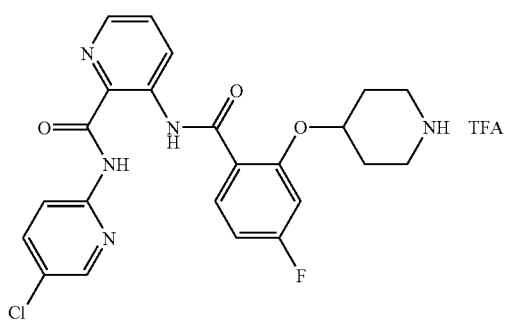

A. N-(5-Chloropyridin-2-yl)-3-aminopyridine-2-carboxamide

A medium pressure reaction apparatus was charged with 3-amino-2-chloropyridine (500 mg, 3.89 mmol), 2-amino-5-chloropyridine (1.00 g, 7.78 mmol), palladium acetate (88 mg, 0.39 mmol), 1,3-bis(diphenylphosphino)propane (483 mg, 1.17 mmol) and triethylamine (590 mg, 5.84 mmol). The mixture was placed under a carbon monoxide atmosphere at 4.1 bar (60 psig) and heated at 100° C. After 72 h, the mixture was filtered, concentrated and the residue purified by column chromatography ($SiO_2$: 0 to 5% EtOAc in methylene chloride) affording 550 mg (57%) of the title compound.

$^1$NMR, IR

IS-MS, m/e 249 (m+1)

Analysis for $C_{11}H_9ClN_4O$:

Calcd: C, 53.13; H, 3.65; N, 22.53;

Found: C, 53.40; H, 3.66; N, 22.45.

B. 2-(1-tert-Butoxycarbonylpiperidin-4-yloxy)-4-fluoro-benzoic Acid

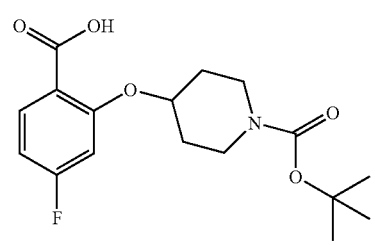

A mixture of methyl 2-(1-tert-butoxycarbonylpiperidin-4-yloxy)-4-fluorobenzoate (3.05 g, 8.64 mmol), 1 M aq LiOH (15 mL, 15 mmol), MeOH (15 mL), and THF (45 mL) was stirred overnight. The reaction mixture was diluted with EtOAc, washed with satd citric acid, dried over $MgSO_4$, concentrated, and triturated with ether to give the acid as a white solid (2.23 g, 76%).

$^1$NMR (300 MHz, $CDCl_3$): δ 7.68 (m, 1H), 7.10 (d, J=8.7 Hz, 1H), 6.79 (m, 1H), 4.72 (m, 1H), 3.48 (m, 4H), 1.65 (m, 2H), 1.60 (m, 2H), 1.37 (s, 9H).

IS-MS, m/e: 340(m+1).

C. N-(5-Chloropyridin-2-yl)-3-[4-fluoro-2-(piperidin-4-yloxy)benzoylamino]pyridine-2-carboxamide Trifluoroacetate Using methods substantially equivalent to those described in Example 1-I, 3-amino-N-(5-chloropyridin-2-yl)-pyridine-2-carboxamide (347 mg, 1.40 mmol) and 2-(1-tert-butoxycarbonylpiperidin-4-yloxy)-4-fluorobenzoic acid (500 mg, 1.47 mmol) yielded, after deprotection of the coupled product using methods substantially equivalent to those described in Example 1-J, 250 mg (38%) of the title compound.

$^1$NMR, IR

IS-MS, m/e=470 (m+1)

Analysis for $C_{28}H_{29}ClFN_5O_5 \cdot H_2O \cdot 6\ CF_3CO_2H$:

Calcd: C, 35.86; H, 2.49; N, 5.97;

Found: C, 35.67; H, 2.65; N, 6.57.

EXAMPLE 3

Preparation of N-(5-Chloropyridin-2-yl)-3-[2-(piperidin-4-yloxy)-4-(pyrrolidin-1-yl)benzoylamino]pyridine-2-carboxamide Trifluoroacetate

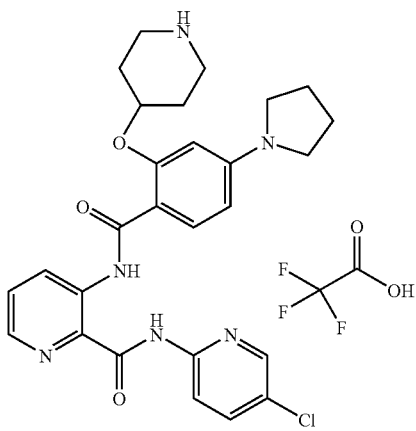

A. 3-[2-(1-tert-Butoxycarbonylpiperidin-4-yloxy)-4-(pyrrolidin-1-yl)benzoylamino]-N-(5-chloropyridin-2-yl)-pyridine-2-carboxamide

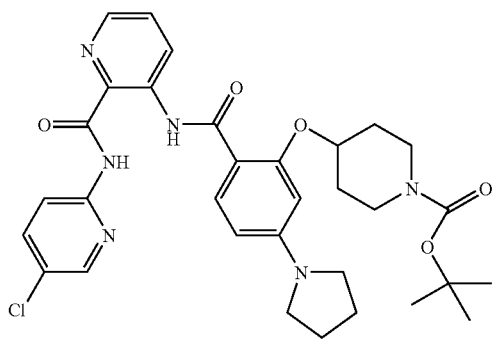

Using methods substantially equivalent to those described in Example 1-G, 3-[4-fluoro-2-(1-tert-butoxy-carbonylpiperidin-4-yloxy)benzoylamino]-N-(5-chloropyridin-2-yl)pyridine-2-carboxamide (100 mg, 0.18 mmol) and pyrrolidine (5.0 mL) yielded, after purification by flash chromatography (SiO$_2$: methylene chloride), 112 mg (99%) of the title compound.

$^1$NMR, IR
IS-MS, m/e=621.5 (m+1)

B. N-(5-Chloropyridin-2-yl)-3-[2-(piperidin-4-yloxy)-4-(pyrrolidin-1-yl)benzoylamino]pyridine-2-carboxamide Trifluoroacetate Using methods substantially equivalent to those described in Example 1-C, 3-[2-(1-tert-butoxycarbonyl-piperidin-4-yloxy)-4-(pyrrolidin-1-yl) benzoylamino]-N-(5-chloropyridin-2-yl)pyridine-2-carboxamide (100 mg, 0.16 mmol) yielded, after purification by flash chromatography (SiO$_2$: 5% to 20% methanol in methylene chloride), 25 mg (30%) of the title compound.

$^1$NMR, IR
IS-MS, m/e=521.32 (m+1)

EXAMPLE 4

Preparation of N-(5-Chloropyridin-2-yl)-3-[4-(morpholin-4-yl)-2-(piperidin-4-yloxy)benzoylamino]pyridine-2-carboxamide Trifluoroacetate

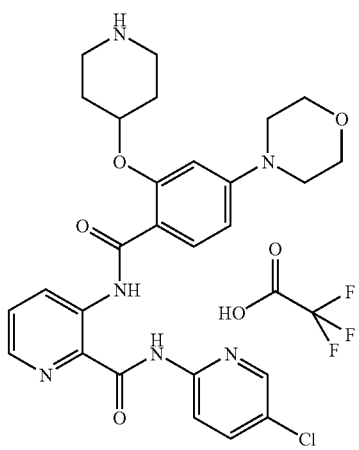

A. 3-[2-(1-tert-Butoxycarbonylpiperidin-4-yloxy)-4-(morpholin-4-yl)benzoylamino]-N-(5-chloropyridin-2-yl)-pyridine-2-carboxamide

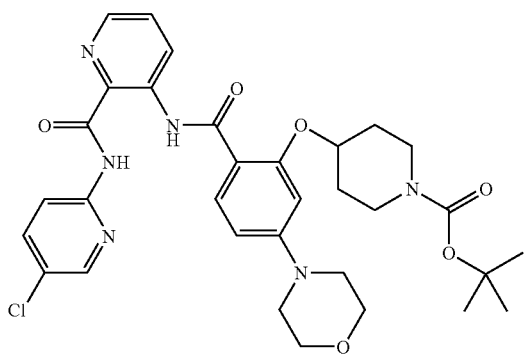

Using methods substantially equivalent to those described in Example 1-G, 3-[4-fluoro-2-(1-tert-butoxy-carbonylpiperidin-4-yloxy)benzoylamino]-N-(5-chloropyridin-2-yl)pyridine-2-carboxamide (100 mg, 0.18 mmol) and morpholine (5.0 mL) yielded, after purification by flash chromatography (SiO$_2$: 5 to 20% methanol:methylene chloride), 55 mg (48%) of the title compound.

$^1$NMR, IR
IS-MS, m/e=637 (m+1)
Analysis for C$_{32}$H$_{37}$ClN$_6$O$_6$:
Calcd: C, 60.33; H, 5.85; N, 13.19;
Found: C, 60.44; H, 6.11; N, 12.96.

B. N-(5-Chloropyridin-2-yl)-3-[4-(morpholin-4-yl)-2-(piperidin-4-yloxy)benzoylamino]pyridine-2-carboxamide Trifluoroacetate Using methods substantially equivalent to those described in Example 1-C, 3-[2-(1-tert-butoxycarbonyl-piperidin-4-yloxy)-4-(morpholin-4-yl)benzoylamino]-N-(5-chloropyridin-2-yl)pyridine-2-carboxamide (300 mg, 0.53 mmol) yielded, after purification by flash chromatography (SiO$_2$: 5% to 10% methanol in methylene chloride), 320 mg (96%) of the title compound.
$^1$NMR
IS-MS, m/e=537.35 (m+1)

EXAMPLE 5

Preparation of 3-[4-(tert-Butyl)-2-(piperidin-4-yloxy)-benzoylamino]-N-(5-chloropyridin-2-yl)pyridine-2-carboxamide Trifluoroacetate

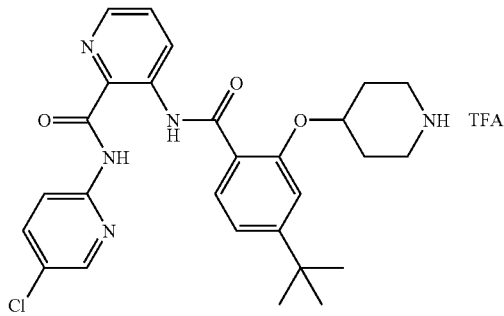

A. Methyl 4-(tert-Butyl)-2-(1-Boc-piperidin-4-yloxy)-benzoate

To a stirring solution of methyl 4-tert-butyl-2-hydroxybenzoate (9.45 g, 45.4 mmol), 1-Boc-piperidin-4-ol (9.6 g, 47.7 mmol) and triphenylphosphine (12.5 g, 47.7 mmol) in THF (125 mL) was added, dropwise via an addition funnel, a solution of diisopropyl azodicarboxylate (9.4 mL, 47.7 mmol) in THF (25 mL). After 72 h, the solvent was removed in vacuo and the residue was dissolved in a minimal amount of chloroform and vacuum filtered through a pad of silica gel, eluting with a solution of 20% ethyl acetate in hexanes. The filtrate was then concentrated in vacuo and the residue was chromatographed over silica gel, eluting with a gradient of 5% ethyl acetate in hexanes through 20% ethyl acetate in hexanes. The product containing fractions were combined and concentrated in vacuo to give the ether (12.9 g, 73%) as a thick colorless oil.
$^1$NMR
ES-MS, m/e 392.3 (m+1)

B. 4-(tert-Butyl)-2-(1-Boc-piperidin-4-yloxy)benzoic acid

To a stirring solution of methyl 4-(tert-butyl)-2-(1-Boc-piperidin-4-yloxy)benzoate (12.9 g, 33 mmol) in p-dioxane (150 mL) was added a solution of LiOH hydrate (2.8 g, 66 mmol) in water (75 mL). The next morning, the solvent was removed in vacuo, and the residue was diluted with water (200 mL) and washed with diethyl ether. The aqueous phase was then adjusted to pH 3 with citric acid and extracted twice with diethyl ether. The combined ether extracts were then washed twice with brine, dried with MgSO$_4$, filtered and concentrated in vacuo to give 11.3 g (91%) of a white foam.
$^1$NMR
IS-MS, m/e 378.5 (m+1)
Analysis for C$_{21}$H$_{31}$NO$_5$:
Calcd: C, 66.82; H, 8.28; N, 3.71;
Found: C, 67.06; H, 8.39; N, 3.71.

C. 3-[4-(tert-Butyl)-2-(piperidin-4-yloxy)benzoylamino)]-N-(5-chloropyridin-2-yl)pyridine-2-carboxamide Trifluoroacetate Using methods substantially equivalent to those described in Example 1-I, 3-amino-N-(5-chloropyridin-2-yl)-pyridine-2-carboxamide (626 mg, 2.52 mmol) and 2-(1-tert-butoxycarbonylpiperidin-4-yloxy)-4-tert-butylbenzoic acid (500 mg, 1.47 mmol) yielded, after deprotection of the coupled product using methods substantially equivalent to those described in Example 1-J, 470 mg (30%) of the title compound as a trifluoroacetate salt.
$^1$NMR, IR
IS-MS, m/e=508 (m+1)
Analysis for C$_{27}$H$_{30}$ClN$_5$O$_3$.H$_2$O.CF$_3$CO$_2$H
Calcd: C, 54.42; H, 5.20;
Found: C, 54.23; H, 4.98.

The 4-tert-butyl-2-hydroxybenzoate for step A above may be prepared as follows:

D. 3-tert-Butylphenyl methoxymethyl Ether

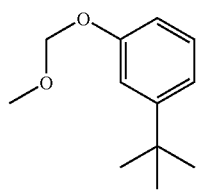

Chloromethyl methyl ether (MOMCl) (76 mL, 998 mmol) was added in one portion to a solution of 3-tert-butylphenol (50.04 g, 333 mmol), diisopropylethylamine (Hünig's base) (203 mL, 1.16 mol) and CH$_2$Cl$_2$ (225 mL) at 0° C. When the addition was complete, the solution was allowed to warm to 23° C., and after 21.5 h additional MOMCl (25 m, 329 mmol) and Hünig's base (60 mL, 344 mmol) were added at room temperature. After an additional 6 h, water (250 mL) was added, and the layers were separated. The organic layer was extracted with water (200 mL), 0.1 N HCl (2×200 mL) and saturated NaHCO$_3$ (200 mL). The organic layer was dried over MgSO$_4$, filtered and concentrated to yield 66.40 g of amber liquid which was purified by flash chromatography (5% EtOAc/hexanes) to provide 50.11 g (77%) of pale yellow liquid:
$^1$H NMR (300 MHz, CDCl$_3$) δ 7.24 (m, 1H, ArH), 7.07 (m, 2H, ArH), 6.90 (m, 1H, ArH), 5.19 (s, 2H, CH$_2$), 3.50 (s, 3H, CH$_3$), 1.33 (s, 9H, C(CH$_3$)$_3$);
$^{13}$C NMR (DMSO-d$_6$, 75 MHz) 156.7, 152.3, 128.9, 124.9, 118.6, 113.5, 112.7, 93.9, 55.5, 34.3, 30.9 ppm;

IR (CHCl$_3$) 1488, 1581, 1608, 1602, 2904, 2966 cm$^{-1}$;
MS (FD+) m/z 194 (100%).

E. 4-tert-Butyl-2-(methoxymethoxy)benzoic Acid

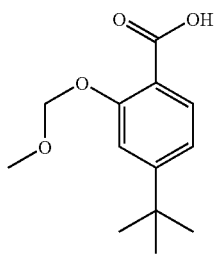

A solution of tert-butyllithium (174 mL, 1.66 M in pentane) was added dropwise to a solution of 3-tert-butyl-phenyl methoxymethyl ether (49.35 g, 254 mmol) and ether (1 liter) at 0° C. over 25 min. The resulting suspension was maintained at 0° C. for 2 h at which point CO$_2$ was sparged through for 20 min. The clear solution was allowed to warm, and water (500 mL) was added. The ether layer was extracted with water (300 mL) and was then discarded. Ether (500 mL) was added to the aqueous layer, and the pH was adjusted from 8-9 to 6 by treatment with 12 N HCl. The aqueous layer was further washed with ether (3×100 mL), and the combined organic layers were dried (Na$_2$SO$_4$), filtered and concen-trated to 26.18 g (43%) of light yellow solid (mp 77.7-79.7° C.).

$^1$H NMR (300 MHz, CDCl$_3$) δ 8.08 (d, J=8.34 Hz, 1H, 6-ArH), 7.26 (d, J=1.62 Hz, 1H, 3-ArH), 7.20 (dd, J=1.60, 8.27 Hz, 1H, 5-ArH), 5.42 (s, 2H, CH$_2$), 3.57 (s, 3H, CH$_3$), 1.33 (s, 9H, C(CH$_3$)$_3$);

$^{13}$C NMR (DMSO-d$_6$, 75 MHz) 167.1, 156.2, 155.8, 130.6, 120.0, 118.6, 113.9, 95.1, 55.9, 34.8, 30.8 ppm; IR (CHCl$_3$) 1402, 1423, 1611, 1735, 2968, 3019 cm$^{-1}$;

MS (FD+) m/z 477 (7%), 283 (6%), 238 (100%), 193 (5%).

Anal. for C$_{13}$H$_{18}$HO$_4$:

Calcd: C, 65.53; H, 7.61;

Found: C, 65.82; H, 7.81.

An alternate procedure is as follows: A solution of 3-tert-butylphenyl methoxymethyl ether (42.53 g, 219 mmol), tetramethylethylenediamine (TMEDA, 36.3 mL, 241 mmol) and ether (425 mL) was cooled to −42° C., and n-butyllithium (95.6 mL, 2.52 M in hexanes) was added over 10 min. During the addition the temperature rose to −33° C., and after the addition it was maintained between −30° C. and −17° C. for 1 h. The solution was slowly warmed to −10° C. resulting in a slurry which was stirred at this temperature for 2 h. Gaseous CO$_2$ was sparged through the slurry for 20 min. (After an initial exotherm to 16° C. the temperature fell to −4° C. for the remainder of the addition). The turbid solution was allowed to warm to 14° C. overnight under a CO$_2$ atmosphere, and water was (200 mL) was added which caused an exotherm, as well as effervescence. The resulting emulsion was placed in a separatory funnel with Et$_2$O (100 mL) and 25% (w/w) NaCl (25 mL). The aqueous layer was extracted with Et$_2$O (50 mL) and the combined organic layers were discarded. The aqueous layer was placed in a beaker with ether (600 mL) and the pH was adjusted from 10-11 to 6 with 12 N HCl. The aqueous layer was washed with ether (75 mL) and the combined organic layers were extracted with 0.25 N HCl (75 mL) to remove any residual TMEDA, and with 5% (w/w) NaHCO$_3$ (75 mL). The organic layer was dried (MgSO$_4$), filtered and evaporated to 28.84 g (55%) of 4-tert-butyl-2-(methoxymethoxy)benzoic acid.

F. Methyl 4-tert-Butyl-2-hydroxybenzoate

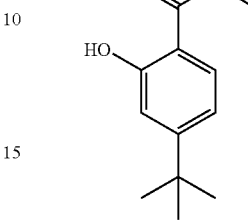

A solution of 4-tert-butyl-2-(methoxymethoxy)benzoic acid (61.80 g, 259 mmol) and MeOH (865 mL) was cooled in an ice bath. Gaseous HCl was sparged through the cold fluid for 30 min to saturate it, and the solution was then heated to reflux. A Soxhlet extractor containing 3 Å molecular sieves was used to absorb the water produced in the reaction. After 16 h the heating mantle was removed, and the solution was allowed to cool to ambient temperature. The filtrate was concentrated to a thick semisolid which was taken up in 1:1 water/CH$_2$Cl$_2$ (800 mL). The aqueous layer was extracted once with CH$_2$Cl$_2$ (100 mL), and the combined organic layers were washed with water (250 mL) and 5% (w/w) NaHCO$_3$ (200 mL). The organic layer was dried (MgSO$_4$), filtered and concentrated to 49.54 g (92%) of yellow oil:

$^1$H NMR (300 MHz, CDCl$_3$) δ 7.74 (d, J=8.42 Hz, 1H, 6-ArH), 7.00 (d, J=1.62 Hz, 1H, 3-ArH), 6.92 (dd, J=1.64, 8.38 Hz, 1H, 5-ArH), 3.93 (s, 3H, CO$_2$Me), 1.30 (s, 9H, C(CH$_3$)$_3$);

$^{13}$C NMR (DMSO-d$_6$, 75 MHz) 169.3, 160.1, 159.4, 129.5, 124.9, 116.8, 113.9, 109.9, 52.2, 34.8, 30.5 ppm;

MS (FD+) m/z 326 (100%), 208 (50%).

EXAMPLE 6

Preparation of N-(5-Chloropyridin-2-yl)-3-[4-isopropyl-2-(piperidin-3-ylmethoxy)benzoylamino]pyridine-2-carboxamide Hydrochloride

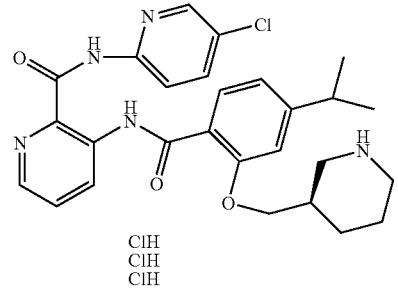

A. 1-Isopropyl-3-methoxymethoxybenzene

Into methylene chloride (300 mL) was dissolved 3-isopropylphenol (27.24 g, 200 mmol). After cooling the solution in an ice bath, diisopropylethyl amine (69.7 mL, 400 mmol) was added in one portion, followed by the dropwise addition of chloromethyl methyl ether (18.9 mL, 236 mmol) in methylene chloride (50 mL). The reaction mixture was gradually allowed to come to room temperature. After 16 h, the reaction mixture was diluted with cold water (500 mL) and methylene chloride. The mixture was shaken in a separatory funnel and the layers were separated. The organic layer was extracted with cold water (2×500 mL), dried (MgSO$_4$), and concentrated under vacuum. The product was dissolved in ether (200 mL) and stirred with 5 N NaOH (200 mL) at room temperature for 5 min. The ether layer was separated and extracted with cold 1N HCl (200 mL), dried (MgSO$_4$), and concentrated under vacuum. The product was chromatographed over silica (0 to 30% EtOAc in hexane gradient), giving 20.0 g (56%) of the title compound.

$^1$NMR

FD-MS, m/e: 180 (m)

B. 4-Isopropyl-2-methoxymethoxybenzoic Acid

Into ether (450 mL) was dissolved 1-isopropyl-3-methoxymethoxybenzene (20.0 g, 111 mmol), and the resulting solution was cooled to −15° C. via an ice-salt-acetone-bath. Under nitrogen, 1.7 M tert-butyl lithium (78.4 mL, 133.2 mmol) was added dropwise over 10 min; and the reaction mixture was stirred for an additional 10 min. Excess carbon dioxide was bubbled in over 5 min; then the reaction mixture was poured into cold water (400 mL) and shaken in a separatory funnel. The aqueous layer was acidified with cold 1 N HCl and shaken with ether (300 mL). The ether layer was washed with water (300 mL), dried (MgSO$_4$), and concentrated under vacuum. The product was dissolved in a minimum amount of hexanes, giving 19.5 g (78%) of the title compound as a solid on standing at room temperature.

$^1$NMR

IS-MS, m/e: 225 (m+1), 223 (m−1)

C. Methyl 4-Isopropyl-2-hydroxybenzoate

The 4-isopropyl-2-methoxymethoxybenzoic acid (5.3 g, 23.6 mmol) was dissolved in methylene chloride (75 mL) and MeOH (75 mL). Acetyl chloride (1 mL) was added to generate HCl. The reaction mixture was stirred for 2 h. The reaction was washed with water (2×150 mL), dried (MgSO$_4$), and concentrated under vacuum. The crude product was dissolved in methylene chloride (100 mL) and MeOH (30 mL) and to this solution a 2 M hexane solution of (trimethylsilyl)diazomethane (11.8 mL, 23.6 mmol) was added dropwise. After 1 h, the solvent was removed under vacuum, giving the title compound as an oil.

$^1$NMR

D. Methyl 2-(1-tert-Butoxycarbonylpiperidin-3-ylmethoxy)-4-isopropylbenzoate The methyl 4-isopropyl-2-hydroxybenzoate (4.4 g, 22.7 mmol) was dissolved in THF (100 mL). Then 3-(hydroxymethyl)-1-tert-butoxycarbonylpiperidine (4.88 g, 22.7 mmol) and triphenylphosphine (7.14 g, 27.24 mmol) were added. The mixture was placed in an ice bath, and then diisopropyl azodicarboxylate (4.59 g, 22.7 mmol) in methylene chloride (15 mL) was added dropwise. The reaction mixture was allowed to warm gradually to room temperature. After 16 h, the solvent was removed under vacuum. The solid residue was subjected directly to flash chromatography on silica (0 to 30% EtOAc in hexane gradient), giving the title compound (3.34 g, 43% yield) as an oil.

$^1$NMR

E. 2-(1-tert-Butoxycarbonylpiperidin-3-ylmethoxy)-4-isopropylbenzoic Acid

The methyl 4-isopropyl-2-(1-tert-butoxycarbonyl-piperidin-3-ylmethoxy)benzoate (1.53 g, 3.90 mmol) was dissolved in THF (15 mL). Then LiOH.H$_2$O (0.36 g, 8.58 mmol) in water (5 mL) was added. The mixture was heated at 65° C. for 24 h. The reaction mixture was concentrated in vacuo and then redissolved in a mixture of EtOAc (100 mL) and cold dilute HCl. The mixture was shaken in a separatory funnel. The layers were separated and the organic layer was washed with cold water (100 mL), dried (MgSO$_4$), and concentrated to give 1.23 g of the title compound as an oil.

$^1$NMR

F. N-(5-Chloropyridin-2-yl)-3-[4-isopropyl-2-(piperidin-3-ylmethoxy)benzoylamino]pyridine-2-carboxamide Hydrochloride Using methods substantially equivalent to those described in Example 1-I and 1-J, N-(5-chloropyridin-2-yl)-3-[4-isopropyl-2-(piperidin-3-ylmethoxy)benzoylamino]-pyridine-2-carboxamide hydrochloride (50 mg, 0.08 mmol, 7%) was prepared from 2-(1-tert-butoxycarbonylpiperidin-3-yl-methoxy)-4-isopropylbenzoic acid and 3-amino-N-(5-chloro-pyridin-2-yl)pyridine-2-carboxamide after reverse phase HPLC purification.

$^1$NMR

EXAMPLE 7

Preparation of 2-[4-(tert-Butyl)-2-(piperidin-4-yloxy)-benzoylamino]-N-(5-chloropyridin-2-yl)pyridine-3-carboxamide Hydrochloride

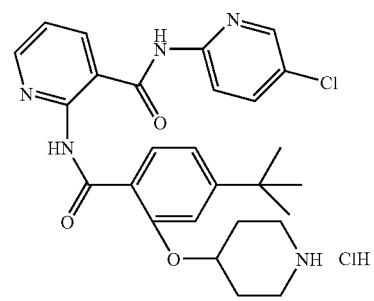

A. 2-Amino-N-(5-chloropyridin-2-yl)pyridine-3-carboxamide Hydrochloride

To a stirring suspension of 2-aminonicotinic acid (26.9 g, 194 mmol) in dichloromethane (120 mL) at 0° C., was added DMF (a few drops), followed by oxalyl chloride (20 mL, 194 mmol). The cold bath was removed, and the solution was allowed to stir for 60 min at room temperature. This solution was then transferred via cannula into a stirring solution of 2-amino-5-chloropyridine (25 g, 194 mmol) and pyridine (78 mL, 970 mmol) in dichloromethane (100 mL). After stirring overnight, the precipitate was filtered and dried to give 32.8 g of solid. The crude product was recrystallized from ethanol with activated charcoal to give the amide (12.4 g, 23%) as a white solid.

¹NMR

IS-MS, m/e 249.0 (m+1)

Analysis for $C_{11}H_9ClN_4O \cdot HCl$:

Calcd: C, 46.33; H, 3.54; N, 19.65; Cl, 24.87;

Found: C, 46.64; H, 3.42; N, 19.63; Cl, 25.23.

B. 2-[4-(tert-Butyl)-2-(piperidin-4-yloxy)benzoylamino]-N-(5-chloropyridin-2-yl)pyridine-3-carboxamide Hydrochloride To a stirring suspension of 2-amino-N-(5-chloropyridin-2-yl)pyridine-3-carboxamide hydrochloride (0.80 g, 3.2 mmol) in dichloromethane (20 mL) was added a solution of 4-tert-butyl-2-(1-Boc-piperidin-4-yloxy)benzoyl chloride (5.3 mmol) in dichloromethane (20 mL), followed by pyridine (2.1 mL, 26.5 mmol). The acid chloride formation of 4-tert-butyl-2-(1-Boc-piperidin-4-yloxy)benzoyl chloride was accomplished by a procedure equivalent to that described for 2-(1-tert-butoxycarbonylpiperidin-4-yloxy)-4-(pyrrolidin-1-yl)benzoyl chloride in Example 1-I but starting from 4-tert-butyl-2-(1-Boc-piperidin-4-yloxy)benzoic acid. After stirring overnight, the solvent was removed in vacuo and the residue was chromatographed over silica gel, eluting with a step gradient of 10% ethyl acetate in hexanes through 75% ethyl acetate in hexanes and, finally, with a solution of 15% methanol in dichloromethane. The product containing fractions were combined and concentrated in vacuo and the residue was then dissolved in a solution of 4 N HCl in dioxane. After 10 min, the precipitate was collected, washed with ether and dried in vacuo to give 0.347 g of a white solid. The solid was then purified by preparative RPHPLC. The product containing fractions were combined, partially concentrated in vacuo and lypholized to give the title compound (0.079 g, 4.5%) as a fluffy white solid.

¹NMR

IS-MS, m/e 508.3 (m+1)

Analysis for $C_{27}H_{30}ClN_5O_3 \cdot 2.5\ HCl \cdot H_2O$:

Calcd: C, 52.54; H, 5.63; N, 11.35;

Found: C, 52.38; H, 5.24; N, 11.38.

EXAMPLE 8

Preparation of N-(5-Chloropyridin-2-yl)-3-[2-[3-(N-formyl-amino)propoxy]-4-(morpholin-4-yl)benzoylamino]pyridine-2-carboxamide

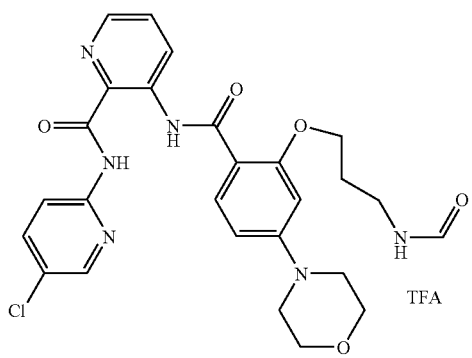

A. Methyl 2-(3-tert-Butoxycarbonylaminopropoxy)-4-fluoro-benzoate

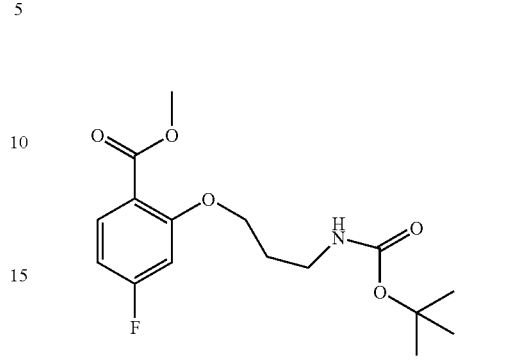

Using a procedure equivalent to Example 1-F, methyl 4-fluoro-2-hydroxybenzoate and 3-(tert-butoxycarbonylamino)-propanol gave the ether product as a white solid (20.6 g, 84%).

¹NMR

IS-MS, m/e: 328(m+1).

B. Methyl 2-(3-tert-Butoxycarbonylaminopropoxy)-4-(morpholin-4-yl)benzoate

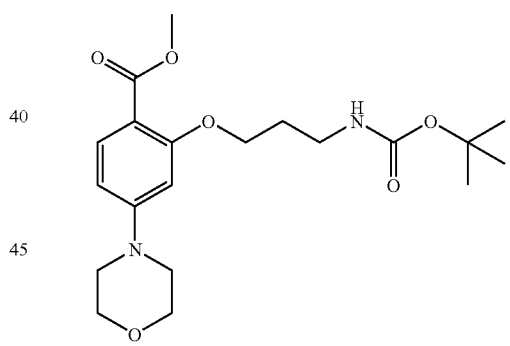

Using methods substantially equivalent to those described in Example 1-G, except that the reaction mixture was heated to 130° C., methyl 2-(3-tert-butoxycarbonylamino-propoxy)-4-(morpholin-4-yl)benzoate (2.39 g, 6.06 mmol, 16%) was prepared from methyl 2-(3-tert-butoxycarbonylamino-propoxy)-4-fluorobenzoate and morpholine.

¹NMR (300 MHz, DMSO-$d_6$): δ 7.60(d, J=9.0 Hz, 1H); 6.84 (m, 1H); 6.50 (d, J=9.0 Hz, 1H); 6.46 (s, 1H); 3.98 (t, J=5.9 Hz, 2H); 3.68 (m, 4H); 3.22 (m, 4H); 3.10 (q, J=6.3 Hz, 2H); 1.79 (t, J=6.3 Hz, 2H); 1.33 (s, 9H).

IS-MS, m/e 395.2 (m+1).

Analysis for $C_{20}H_{30}N_2O_6$:

Calcd: C, 60.90; H, 7.67; N, 7.10;

Found: C, 60.61; H, 7.45; N, 7.08.

C. 2-(3-tert-Butoxycarbonylaminopropoxy)-4-(morpholin-4-yl)benzoic Acid

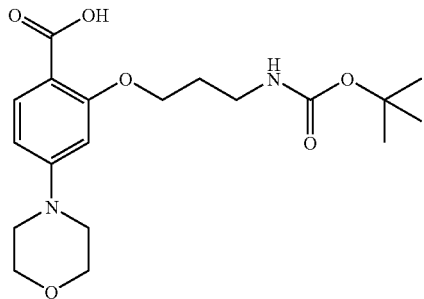

The methyl 2-(3-tert-butoxycarbonylaminopropoxy)-4-(morpholin-4-yl)benzoate (2.34 g, 5.93 mmol) was diluted with ethanol (60 mL) and water (60 mL). Potassium hydroxide pellets (1.64 g, 29.2 mmol) were added, and the resulting mixture was heated to 70° C. After 2 h, the reaction mixture was concentrated in vacuo. The residue was diluted with methylene chloride (200 mL) and extracted with saturated aqueous citric acid (2×50 mL). The organic layer was dried over sodium sulfate, filtered, and concentrated to give the acid (2.24 g, 5.90 mmol, 99%).

$^1$NMR (300 MHz, DMSO-$d_6$): δ 7.59(d, J=8.7 Hz, 1H); 6.85 (m, 1H); 6.49 (m, 2H); 4.00 (t, J=5.9 Hz, 2H); 3.68 (m, 4H); 3.21 (m, 4H); 3.07 (m, 2H); 1.79 (t, J=6.2 Hz, 2H); 1.33 (s, 9H).

IS-MS m/e: 381.4 (m+1).

D. N-(5-Chloropyridin-2-yl)-3-[2-[3-(N-formylamino)-propoxy]-4-(morpholin-4-yl)benzoylamino]pyridine-2-carboxamide Trifluoroacetate Using methods substantially equivalent to those described in Example 1-I, 3-amino-N-(5-chloropyridin-2-yl)-pyridine-2-carboxamide (187 mg, 0.75 mmol), N,N-dimethyl-formamide (0.2 mL) and 2-(3-tert-butoxycarbonylamino-propoxy)-4-(morpholin-4-yl)benzoic acid (300 mg, 0.79 mmol) yielded, after deprotection using methods substantially equivalent to those described in Example 1-J, 25 mg (5%) of the title N-formyl compound (which apparently arose from formylation involving the DMF under the reaction conditions to afford an N-Boc-N-formyl derivative) as a trifluoroacetate salt.

$^1$NMR, IR
FD-MS, m/e=538 (m)
Analysis for $C_{26}H_{27}ClN_6O_5$:
Calcd: C, 57.94; H, 5.05; N, 15.59;
Found: C, 57.73; H, 5.18; N, 15.16.

EXAMPLE 9

Preparation of 3-[2-(2-Aminoethoxy)-4-(morpholin-4-yl)-benzoylamino]-N-(5-chloropyridin-2-yl)pyridine-2-carboxamide Trifluoroacetate

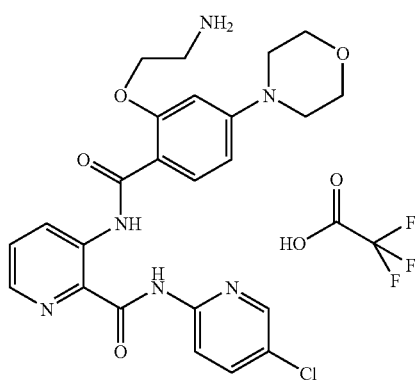

A. Ethyl 2-(2-tert-Butoxycarbonylaminoethoxy)-4-fluoro-benzoate

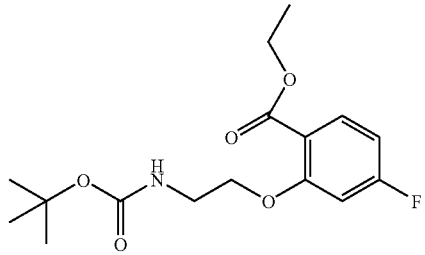

To a solution of 2-(tert-butoxycarbonylamino)ethanol (4.34 g, 26.9 mmol) in THF (16 mL) at 0° C. under $N_2$, was added potassium tert-butoxide ($K^{+-}$OtBu, 26.9 mL, 26.9 mmol, 1.0 M in THF). The reaction mixture was stirred for 20 min at 0° C. during which time a thick slurry formed. The anion solution was then poured into a solution of ethyl 2,4-di-fluorobenzoate (5.00 g, 26.9 mmol) in THF (16 mL) which had been cooled to −65° C. The reaction mixture was allowed to slowly warm to room temperature and was stirred for 18 h. The mixture was diluted with dichloromethane and washed with water. The water layer was extracted with additional dichloromethane and the dichloromethane layers combined and washed with brine, dried, and concentrated in vacuo to give a yellow oil. Purification on silica gel, eluting with a gradient of 4:1 to 3:1 hexane:EtOAc, yielded 3.82 g (43.5%) of the ether as a colorless oil.

B. Ethyl 2-[2-(2-tert-Butoxycarbonylamino)ethoxy]-4-(morpholin-4-yl)benzoate

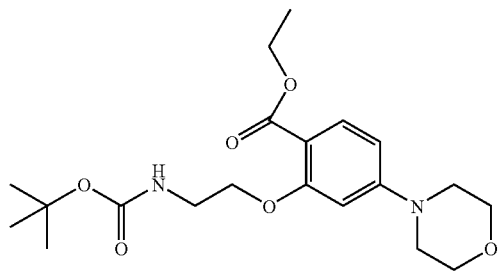

Ethyl 2-(2-tert-butoxycarbonylamino)ethoxy-4-fluorobenzoate (1.75 g, 5.35 mmol) and morpholine (1 mL) were heated at 90° C. in a sealed vial for 7 days. The reaction mixture was diluted with dichloromethane (25 mL), washed with water, dried, and the solvent was removed in vacuo. Purification via silica gel chromatography, eluting with a gradient of hexane and ethyl acetate, yielded 0.791 g (37.5%) of the desired product as a colorless oil.

C. 2-[2-(2-tert-Butoxycarbonylaminoethoxy)-4-(morpholin-4-yl)benzoic Acid

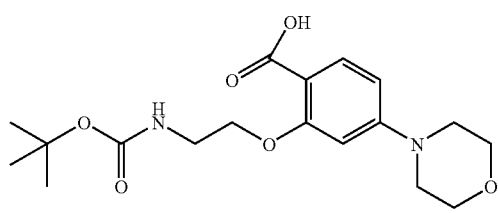

In a manner substantially equivalent to that of Example 1-H, ethyl 2-(2-tert-butoxycarbonylaminoethoxy)-4-(morpholin-4-yl)benzoate (0.790 g, 2.00 mmol) yielded 0.617 g (84.1%) of the acid as a white solid.

IS-MS, m/z 367.1 (m+1), 365.2 (m−)

D. 3-[2-(2-Aminoethoxy)-4-(morpholin-4-yl)benzoylamino]-N-(5-chloropyridin-2-yl)pyridine-2-carboxamide Trifluoroacetate Using methods substantially equivalent to those described in Example 1-I, 3-amino-N-(5-chloropyridin-2-yl)-pyridine-2-carboxamide (321 mg, 1.29 mmol), N,N-dimethyl-formamide (0.2 mL) and 2-(2-tert-butoxycarbonylaminoethoxy)-4-(morpholin-4-yl)benzoic acid (500 mg, 1.36 mmol) yielded, after deprotection of the coupled product using methods substantially equivalent to those described in Example 1-J, 20 mg (2%) of the title compound as a trifluoroacetate salt.

¹NMR

FD-MS, m/e=497 (m+1)

EXAMPLE 10

Preparation of N-(5-Chloropyridin-2-yl)-3-[2-[2-(formyl-amino)ethoxy]-4-(morpholin-4-yl)benzoylamino]pyridine-2-carboxamide Trifluoroacetate

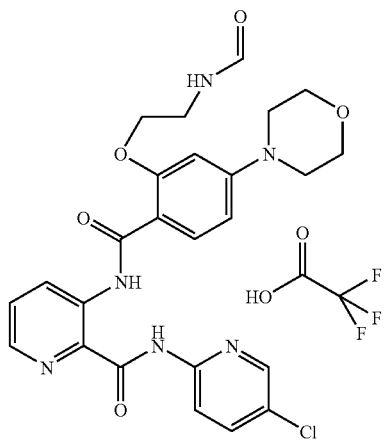

Using methods substantially equivalent to those described in Example 1-I, 3-amino-N-(5-chloropyridin-2-yl)-pyridine-2-carboxamide (321 mg, 1.29 mmol), N,N-dimethyl-formamide (0.2 mL) and 2-(2-tert-butoxycarbonylaminoethoxy)-4-(morpholin-4-yl)benzoic acid (500 mg, 1.36 mmol) yielded, after deprotection of the coupled product using methods substantially equivalent to those described in Example 1-J, 60 mg (7%) of the title N-formyl compound (which apparently arose from formylation involving the DMF under the reaction conditions to afford an N-Boc-N-formyl derivative) as a trifluoroacetate salt.

¹NMR

FD-MS, m/e=525 (m)

EXAMPLE 11

Preparation of N-(5-Chloropyridin-2-yl)-3-[4-(morpholin-4-yl)-2-(piperidin-4-yloxy)benzoylamino]pyridine-2-carboxamide Trifluoroacetate. (Resynthesis of Example 4)

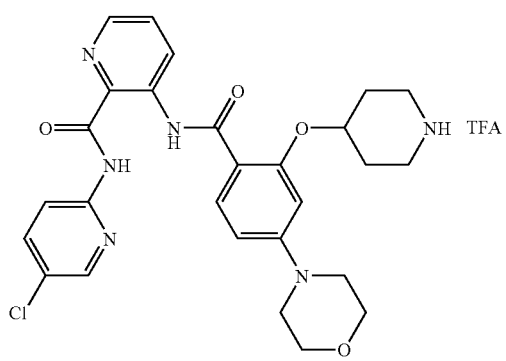

Using methods substantially equivalent to those described in Example 1-G, 3-[2-(1-tert-butoxycarbonyl-piperidin-4-yloxy)-4-fluorobenzoylamino)]-N-(5-chloro-pyridin-2-yl)pyridine-2-carboxamide (300 mg, 0.53 mmol) and morpholine (5 mL) yielded, after deprotection of the coupled product using methods substantially equivalent to those described in Example 1-J, 400 mg (68%) of the title compound as a trifluoroacetate salt.

$^1$NMR, IR
IS-MS, m/e=537 (m)
Analysis for $C_{27}H_{30}ClN_6O_4 \cdot 5\ CF_3CO_2H$:
Calcd: C, 40.14; H, 3.10;
Found: C, 40.41; H, 3.50.

EXAMPLE 12

Preparation of N-(5-Chloropyridin-2-yl)-3-[2-(piperidin-4-yloxy)-4-(pyrrolidin-3-yl)benzoylamino]pyridine-4-carboxamide Trifluoroacetate

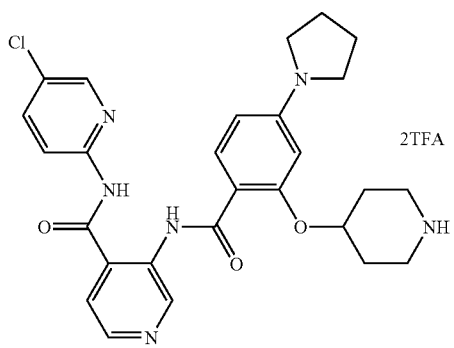

A. 3-Aminopyridine-4-carboxylic Acid

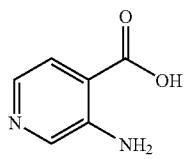

A solution of 10% aqueous NaOH (416 mL) was cooled to 0° C. and treated with bromine (28.2 g 176 mmol) portionwise via pipette while keeping the temperature below 5° C. To this mixture was added 3,4-pyridinedicarboximide (25.78 g, 174 mmol), and the cooling bath was removed. The reaction was heated to 80° C. for 45 min, then allowed to cool in an ice bath. When the temperature fell to 60° C., the dropwise addition of HOAc (50 mL) was started. Cooling was continued until the temperature reached 15° C. A yellow precipitate formed. The solid was filtered, rinsed with water, then dried under vacuum to give 14.9 g of product (108 mmol, 62%).

$^1$NMR
IS-MS, m/e 139 (m+1)

B. Methyl 3-Aminopyridine-4-carboxylate

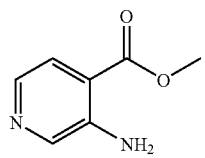

Using methods substantially equivalent to those described in the second part of Example 1-E, methyl 3-amino-pyridine-4-carboxylate was prepared in a 75% yield from 3-aminopyridine-4-carboxylic acid.

$^1$NMR
FD-MS, m/e 153 (m+1)

C. Methyl 3-[2-(1-tert-Butoxycarbonylpiperidin-4-yloxy)-4-(pyrrolidin-1-yl)benzoylamino]pyridine-4-carboxylate

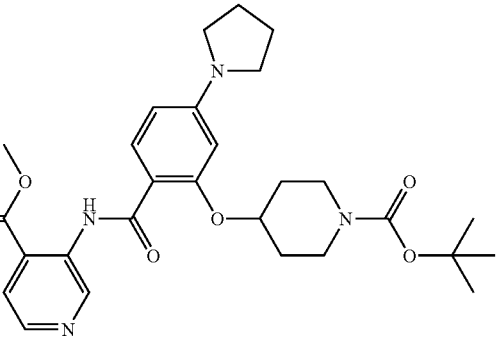

A solution of 2-(1-tert-butoxycarbonylpiperidin-4-yloxy)-4-(pyrrolidin-1-yl)benzoic acid (2 g, 5.1 mmol) in $CH_2Cl_2$ (15 mL) was cooled to 0° C. and treated with a 2 M $CH_2Cl_2$ solution of oxalyl chloride (5.1 mL). The reaction mixture was stirred at 0° C. for 1 h, concentrated to dryness, then redissolved in $CH_2Cl_2$ (5 mL). This solution was added dropwise to a cold solution of methyl 3-amino-pyridine-4-carboxylate, pyridine (2 mL), and $CH_2Cl_2$ (5 mL). The reaction mixture was slowly warmed to room temperature and stirred overnight. The mixture was concentrated to dryness, diluted with saturated aqueous $NaHCO_3$ (50 mL), and extracted with 10% MeOH in EtOAC (3×). The extracts were dried over $MgSO_4$ and concentrated to a dark oil which was purified by flash chromatography, eluting with Hex/THF/$Et_3N$ 65/30/5, to give 1.92 g (71%) of the amide.

$^1$NMR
FD-MS, m/e 525 (m+1)

D. 3-[2-(1-tert-Butoxycarbonylpiperidin-4-yloxy)-4-(pyrrolidin-1-yl)benzoylamino]pyridine-4-carboxylic Acid

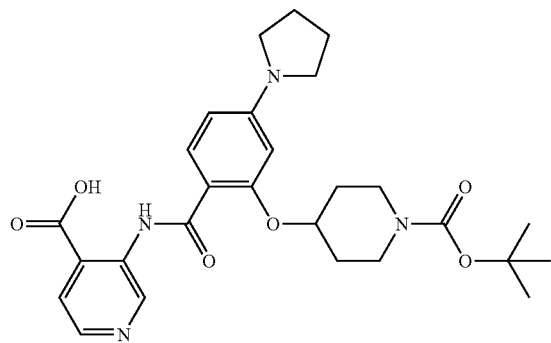

A solution of methyl 3-[2-(1-tert-butoxycarbonyl-piperidin-4-yloxy)-4-(pyrrolidin-1-yl)benzoylamino]pyridine-4-carboxylate (2.78 g, 5.3 mmol) in MeOH (100 mL) and THF (50 mL) was treated with 1 N NaOH (11 mL) and stirred at ambient temperature for 4 h. The reaction was quenched with glacial acetic acid (1 g) and concentrated to dryness. The residue was mixed with brine (50 mL) and extracted with 10% MeOH in CHCl$_3$ (3×). The extracts were dried over MgSO$_4$ and concentrated to 2.2 g (4.3 mmol, 81%) of a yellow solid.
$^1$NMR
FD-MS, m/e 510 (m+)

E. 2-[2-(1-tert-Butoxycarbonylpiperidin-4-yloxy)-4-(pyrrolidin-1-yl)phenyl]-4H-pyrido[3,4-d][1,3]oxazin-4-one

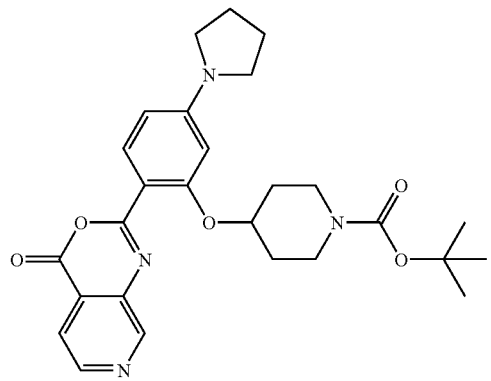

A mixture of 3-[2-(1-tert-butoxycarbonylpiperidin-4-yloxy)-4-(pyrrolidin-1-yl) benzoylamino]pyridine-4-carboxylic acid (2.2 g, 4.1 mmol) and CH$_2$Cl$_2$ (500 mL) was cooled to 0° C. and treated with a 2 M CH$_2$Cl$_2$ solution of oxalyl chloride (5 mL). The reaction mixture was stirred at 0° C. for 1 h, then washed with saturated aqueous NaHCO$_3$ (50 mL). The layers were separated and the organic layer was dried over MgSO$_4$ then concentrated to give 1.8 g (3.7 mmol, 89%) of a yellow solid.
$^1$NMR
IS-MS 523 (m+CH$_3$OH)
Analysis for C$_{27}$H$_{32}$N$_4$O$_5$:
Calcd: C, 65.84; H, 6.55; N, 11.37;
Found: C, 65.75; H, 6.56; N, 11.13.

F. 3-[2-(1-tert-Butoxycarbonylpiperidin-4-yloxy)-4-(pyrrolidin-1-yl)benzoylamino]-N-(5-chloropyridin-2-yl)-pyridine-4-carboxamide

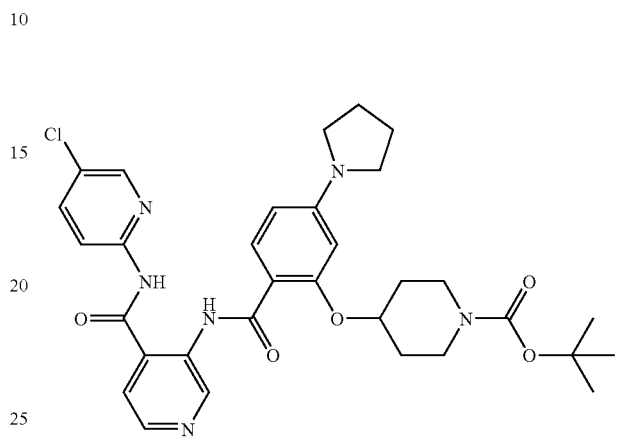

A solution of 2-amino-5-chloropyridine (52 mg, 0.4 mmol) in THF (10 mL) was cooled to 0° C. and treated with a 1 M diethyl ether solution of allylmagnesium bromide (0.4 mL). The mixture was stirred for 5 minutes before adding 2-[2-(1-tert-butoxycarbonylpiperidin-4-yloxy)-4-(pyrrolidin-1-yl) phenyl]-4H-pyrido[3,4-d][1,3]oxazin-4-one (100 mg, 0.2 mmol). The reaction mixture was stirred overnight at ambient temperature then concentrated to dryness under vacuum. The residue was treated with brine (5 mL) and CHCl$_3$ (20 mL). The layers were separated and the organic layer was chromatographed using 1% MeOH in CHCl$_3$ to give 125 mg (0.2 mmol, 99%) of product as a solid.
$^1$NMR
FD-MS, m/e 621 (m+1)

G. N-(5-Chloropyridin-2-yl)-3-[2-(piperidin-4-yloxy)-4-(pyrrolidin-1-yl)benzoylamino]pyridine-4-carboxamide Trifluoroacetate The 3-[2-(1-tert-butoxycarbonylpiperidin-4-yloxy)-4-(pyrrolidin-1-yl)benzoylamino]-N-(5-chloropyridin-2-yl)-pyridine-4-carboxamide (109 mg, 0.18 mmol) was dissolved in CH$_2$Cl$_2$ (2 mL) with anisole (1 mL). The solution was treated with trifluoroacetic acid (1 mL) at room temperature for 2 h. The mixture was concentrated to dryness under vacuum, rinsed with hexanes, and sonicated with diethyl ether (5 mL) for 5 min to give 120 mg (0.16 mmol, 89%) of the title product.
$^1$NMR
FD-MS, m/e 521 (m+1)
Analysis for C$_{27}$H$_{29}$ClN$_6$O$_3$·1.6 CF$_3$COOH·H$_2$O:
Calcd: C, 50.28; H, 4.55; N, 11.65;
Found: C, 50.54; H, 4.31; N, 11.80.

EXAMPLE 13

Preparation of N-(4-Methylthiazol-2-yl)-3-[2-(piperidin-4-yloxy)-4-(pyrrolidin-1-yl)benzoylamino]pyridine-4-carboxamide Trifluoroacetate

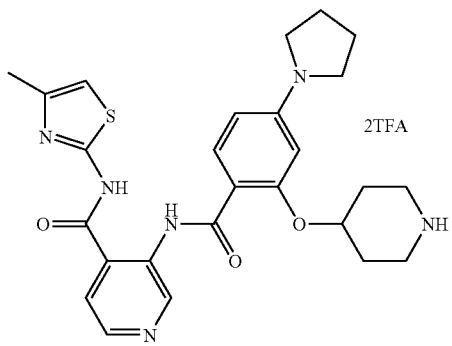

A. 3-[2-(1-tert-Butoxycarbonylpiperidin-4-yloxy)-4-(pyrrolidin-1-yl)benzoylamino]-N-(4-methylthiazol-2-yl)-pyridine-4-carboxamide

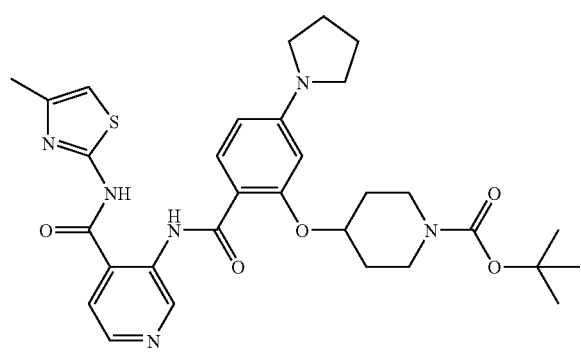

Using methods substantially equivalent to those described in Example 12-F, 3-[2-(1-tert-butoxycarbonyl-piperidin-4-yloxy)-4-(pyrrolidin-1-yl)benzoylamino]-N-(4-methylthiazol-2-yl)pyridine-4-carboxamide was prepared in an 87% yield from 2-[2-(1-tert-butoxycarbonylpiperidin-4-yl-oxy)-4-(pyrrolidin-1-yl)phenyl]-4H-pyrido[3,4-d][1,3]oxazin-4-one and 2-amino-4-methylthiazole.

$^1$NMR
FD-MS, m/e 607 (m+1)

B. N-(4-Methylthiazol-2-yl)-3-[2-(piperidin-4-yloxy)-4-(pyrrolidin-1-yl)benzoylamino]pyridine-4-carboxamide Trifluoroacetate Using methods substantially equivalent to those described in Example 12-G, N-(4-methylthiazol-2-yl)-3-[2-(piperidin-4-yloxy)-4-(pyrrolidin-1-yl)benzoylamino]-pyridine-4-carboxamide trifluoroacetate was prepared in a 74% yield from 3-[4-(pyrrolidin-1-yl)-2-(1-tert-butoxy-carbonylpiperidin-4-yloxy)benzoylamino]-N-(4-methylthiazol-2-yl)pyridine-4-carboxamide.

$^1$NMR
FD-MS, m/e 507 (m+1)

Analysis for $C_{26}H_{30}N_6SO_3 \cdot 2\ CF_3COOH \cdot H_2O$:
Calcd: C, 47.87; H, 4.55; N, 11.17;
Found: C, 47.77; H, 4.22; N, 11.03.

EXAMPLE 14

Preparation of 3-[2-(Piperidin-4-yloxy)-4-(pyrrolidin-1-yl)-benzoylamino]-N-(thiazol-2-yl)pyridine-4-carboxamide Trifluoroacetate

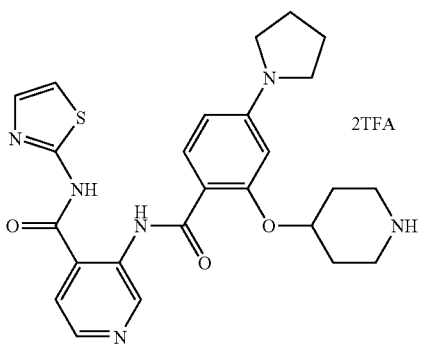

A. 3-[2-(1-tert-Butoxycarbonylpiperidin-4-yloxy)-4-(pyrrolidin-1-yl)benzoylamino]-N-(thiazol-2-yl)pyridine-4-carboxamide

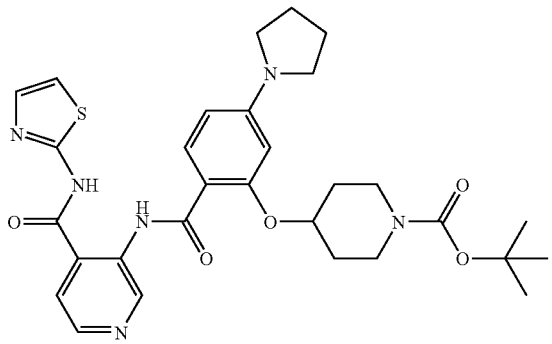

Using methods substantially equivalent to those described in Example 12-F, 3-[2-(1-tert-butoxycarbonyl-piperidin-4-yloxy)-4-(pyrrolidin-1-yl)benzoylamino]-N-(thiazol-2-yl)pyridine-4-carboxamide was prepared in an 87% yield from 2-[2-(1-tert-butoxycarbonylpiperidin-4-yloxy)-4-(pyrrolidin-1-yl)phenyl]-4H-pyrido[3,4-d][1,3]oxazin-4-one and 2-aminothiazole.

$^1$NMR
IS-MS, m/e 593 (m+1)

B. 3-[2-(Piperidin-4-yloxy)-4-(pyrrolidin-1-yl)benzoyl-amino]-N-(thiazol-2-yl)pyridine-4-carboxamide Trifluoroacetate Using methods substantially equivalent to those described in Example 12-G, 3-[2-(piperidin-4-yloxy)-4-(pyrrolidin-1-yl)benzoylamino]-N-(thiazol-2-yl)pyridine-4-carboxamide trifluoroacetate was prepared in a 75% yield from 3-[4-(pyrrolidin-1-yl)-2-(1-tert-butoxycarbonyl-piperidin-4-yloxy)benzoylamino]-N-(thiazol-2-yl)pyridine-4-carboxamide.

¹NMR
FD-MS, m/e 493 (m+1)
Analysis for $C_{25}H_{28}N_6SO_3 \cdot 2\,CF_3COOH$:
Calcd: C, 48.33; H, 4.20; N, 11.66;
Found: C, 48.09; H, 4.17; N, 11.60.

EXAMPLE 15

Preparation of N-(5-Bromothiazol-2-yl)-3-[2-(piperidin-4-yl-oxy)-4-(pyrrolidin-1-yl)benzoylamino]pyridine-4-carboxamide Trifluoroacetate

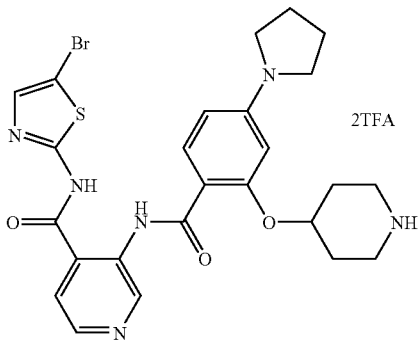

A. N-(5-Bromothiazol-2-yl)-3-[2-(1-tert-butoxycarbonyl-piperidin-4-yloxy)-4-(pyrrolidin-1-yl)benzoylamino]pyridine-4-carboxamide

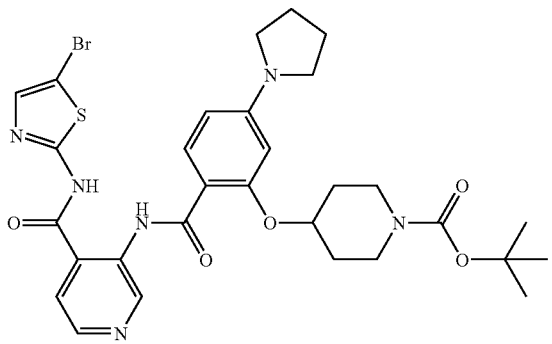

Using methods substantially equivalent to those described in Example 12-F, N-(5-bromothiazol-2-yl)-3-[2-(1-tert-butoxycarbonylpiperidin-4-yloxy)-4-(pyrrolidin-1-yl)-benzoylamino]pyridine-4-carboxamide was prepared in a 47% yield from 2-[2-(1-tert-butoxycarbonylpiperidin-4-yloxy)-4-(pyrrolidin-1-yl)phenyl]-4H-pyrido[3,4-d][1,3]oxazin-4-one and 2-amino-5-bromothiazole.
¹NMR
FD-MS, m/e 671 (m+1)

B. N-(5-Bromothiazol-2-yl)-3-[2-(piperidin-4-yloxy)-4-(pyrrolidin-1-yl)benzoylamino]pyridine-4-carboxamide Trifluoroacetate Using methods substantially equivalent to those described in Example 12-G, N-(5-bromothiazol-2-yl)-3-[2-(piperidin-4-yloxy)-4-(pyrrolidin-1-yl)benzoylamino]-pyridine-4-carboxamide trifluoroacetate was prepared in a 75% yield from N-(5-bromothiazol-2-yl)-3-[2-(1-tert-butoxy-carbonylpiperidin-4-yloxy)-4-(pyrrolidin-1-yl)benzoyl-amino]pyridine-4-carboxamide.
¹NMR
FD-MS, m/e 571,573 (m+1)
Analysis for $C_{25}H_{27}BrN_6SO_3 \cdot 1.5\,CF_3COOH \cdot 0.5\,H_2O$:
Calcd: C, 44.75; H, 3.96; N, 11.18;
Found: C, 45.05; H, 4.03; N, 11.39.

EXAMPLE 16

Preparation of 3-[4-(tert-Butyl)-2-(piperidin-4-yloxy)-benzoylamino]-N-(5-chloropyridin-2-yl)pyridine-4-carboxamide

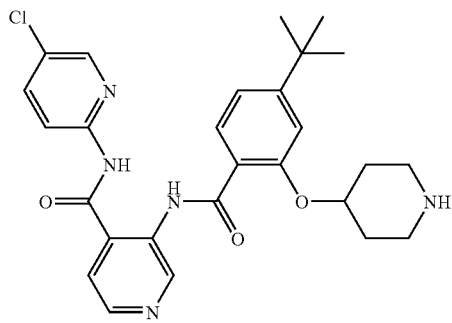

A. Methyl 3-[2-(1-tert-Butoxycarbonylpiperidin-4-yloxy)-4-(tert-butyl)benzoylamino]pyridine-4-carboxylate

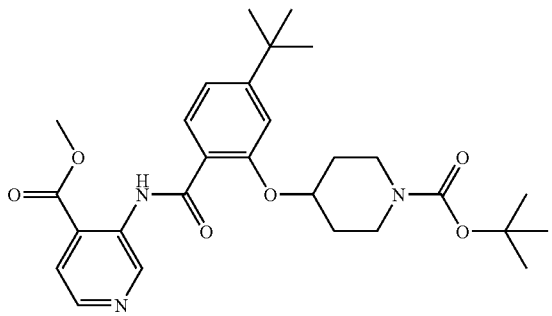

Using methods substantially equivalent to those described in Example 12-C, methyl 3-[2-(1-tert-butoxy-carbonylpiperidin-4-yloxy)-4-(tert-butyl)benzoylamino]-pyridine-4-carboxylate was prepared in a 32% yield from methyl 3-aminopyridine-4-carboxylate and 2-(1-tert-butoxycarbonylpiperidin-4-yloxy)-4-(tert-butyl)benzoic acid.
¹NMR
FD-MS, m/e 512 (m+1)

B. 2-[2-(1-tert-Butoxycarbonylpiperidin-4-yloxy)-4-tert-butylphenyl]-4H-pyrido[3,4-d][1,3]oxazin-4-one

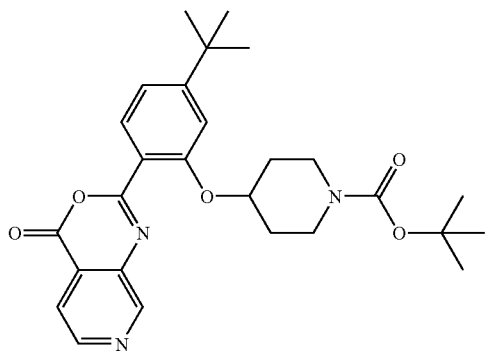

A solution of methyl 3-[2-(1-tert-butoxycarbonyl-piperidin-4-yloxy)-4-(tert-butyl)benzoylamino]pyridine-4-carboxylate (1.2 g, 2.3 mmol) in THF (100 mL) was treated with a 1 M aqueous solution of LiOH followed by MeOH (30 mL). The reaction mixture was stirred at ambient temperature for 2 h, then neutralized with formic acid (200 µL). The resulting solution was, concentrated to dryness under vacuum, mixed with toluene and reconcentrated to dryness.

The residue was mixed with $CH_2Cl_2$ (800 mL), cooled to 0° C., and treated with a 2 M $CH_2Cl_2$ solution of oxalyl chloride (6 mL) and 2 drops of DMF. The reaction mixture was stirred overnight at ambient temperature. The mixture was concentrated under vacuum to dryness and chromatographed on silica using 30% EtOAc in hexanes to give 620 mg (56%) of the title compound as an oil.

$^1$NMR

C. 3-[2-(1-tert-Butoxycarbonylpiperidin-4-yloxy)-4-(tert-butyl)benzoylamino]-N-(5-chloropyridin-2-yl)pyridine-4-carboxamide

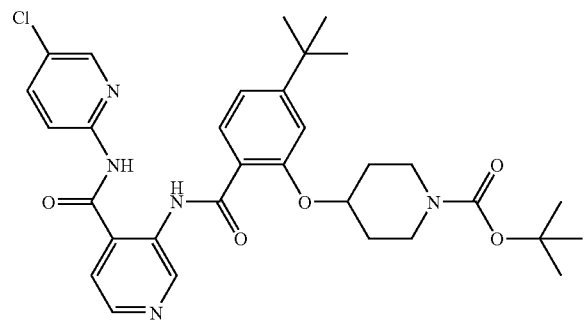

A mixture of 2-[2-(1-tert-butoxycarbonylpiperidin-4-yloxy)-4-tert-butylphenyl]-4H-pyrido[3,4-d][1,3]oxazin-4-one (100 mg, 0.21 mmol), KCN (100 mg), 5-chloro-2-aminopyridine (53 mg, 0.42 mmol), and dry DMF (2 mL) was heated at 70° C. for 4 h, then quenched with brine (25 mL). The mixture was extracted with 10% MQOH in EtOAc (2×20 mL), and the combined extracts were washed with brine (3×100 mL) then dried over $MgSO_4$. After filtering, the filtrate was concentrated to an oil which was purified by chromatography using 60% EtOAc in hexanes to give 30 mg of an oil which crystallized.

$^1$NMR
FD-MS, m/e 608 (m+1)

D. 3-[4-(tert-Butyl)-2-(piperidin-4-yloxy)benzoylamino]-N-(5-chloropyridin-2-yl)pyridine-4-carboxamide The 3-[2-(1-tert-butoxycarbonylpiperidin-4-yloxy)-4-(tert-butyl)benzoylamino]-N-(5-chloropyridin-2-yl)pyridine-4-carboxamide (60 mg, 0.1 mmol) was mixed with anisole (1 mL) and $CH_2Cl_2$ (2 mL) then treated with trifluoroacetic acid (1 mL). The reaction was stirred at ambient temperature for 4 h, concentrated under vacuum to dryness and mixed with $CH_2Cl_2$. This was filtered through a 1 g SCX ion exchange column using 2 M $NH_3$ in MeOH. Concentration to dryness gave 32 mg of the title compound as a solid.

$^1$NMR
FD-MS, m/e 508 (m+)

EXAMPLE 17

Preparation of 3-[2-(Piperidin-4-yloxy)-4-(pyrrolidin-1-yl)-benzoylamino]-N-(pyridin-2-yl) thiophene-2-carboxamide Trifluoroacetate

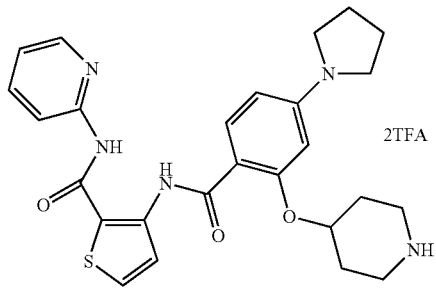

A. Methyl 3-[2-(1-tert-Butoxycarbonylpiperidin-4-yloxy)-4-(pyrrolidin-1-yl)benzoylamino]thiophene-2-carboxylate

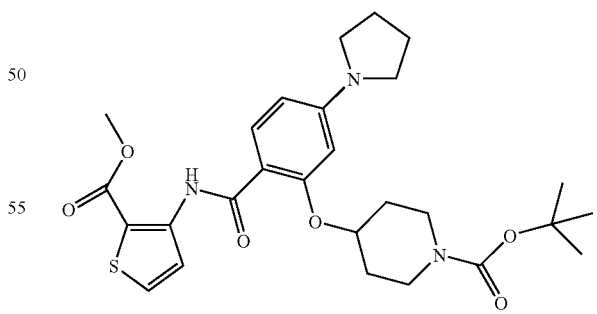

Using methods substantially equivalent to those described in Example 12-C, methyl 3-[2-(1-tert-butoxy-carbonylpiperidin-4-yloxy)-4-(pyrrolidin-1-yl)benzoylamino]-thiophene-2-carboxylate was prepared in a 58% yield from 2-(1-tert-butoxycarbonylpiperidin-4-yloxy)-4-(pyrrolidin-1-yl)benzoic acid and methyl 3-aminothiophene-2-carboxylate.

¹NMR
FD-MS, m/e 530 (m+1)

B. 3-[2-(1-tert-Butoxycarbonylpiperidin-4-yloxy)-4-(pyrrolidin-1-yl)benzoylamino]thiophene-2-carboxylic Acid

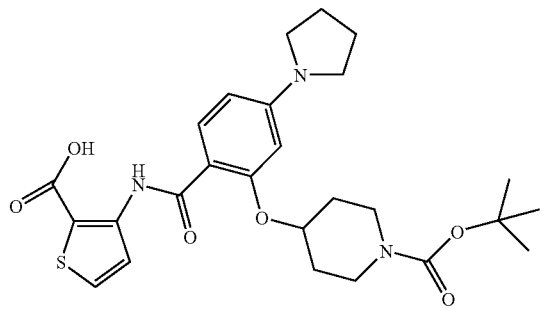

A solution of the methyl 3-[2-(1-tert-butoxycarbonyl-piperidin-4-yloxy)-4-(pyrrolidin-1-yl)benzoylamino]-thiophene-2-carboxylate (3.8 g, 7.2 mmol) and EtOH (100 mL) was treated with a solution of KOH (0.88 g) in water (80 mL). The reaction mixture was refluxed overnight, quenched with glacial acetic acid (1.5 mL) and concentrated under vacuum. The resulting aqueous mixture was extracted with EtOAc (2×100 mL). The combined extracts were dried over MgSO₄ and concentrated to give 3.5 g (6.8 mmol, 94%) of the acid as a foam.
¹NMR
FD-MS, m/e 516 (m+1)

C. 2-[2-(1-tert-Butoxycarbonylpiperidin-4-yloxy)-4-(1-pyrroldinyl)phenyl]-4H-thieno[3,2-d][1,3]oxazin-4-one

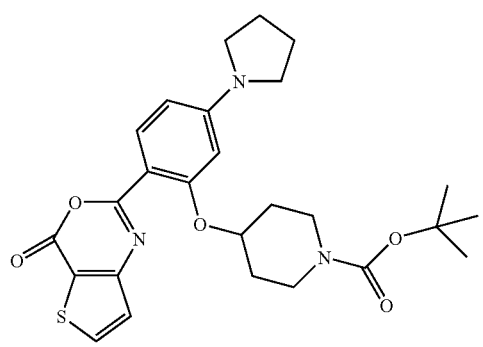

A solution of 3-[2-(piperidin-4-yloxy)-4-(pyrrolidin-1-yl)benzoylamino]thiophene-2-carboxylic acid (3.4 g, 6.6 mmol) in dry DMF (35 mL) was treated with 1-(3-dimethyl-aminopropyl)-3-ethylcarbodiimide hydrochloride (25 g, 13.2 mmol). The reaction was stirred at ambient temperature for 1 h. The mixture was poured into brine (300 mL) and extracted with EtOAc (3×100 mL). The combined extracts were washed with water (300 mL) then with brine (3×300 mL). The organic layer was dried over MgSO₄ and concentrated to a solid which was purified by chromatography on silica using 30% EtOAc in hexanes to give 3.4 g of a yellow solid.
¹NMR
FD-MS, m/e 498 (m+1)

D. 3-[2-(Piperidin-4-yloxy)-4-(pyrrolidin-1-yl)benzoyl-amino]-N-(pyridin-2-yl)thiophene-2-carboxamide Trifluoroacetate A solution of 2-aminopyridine (56.7 mg, 0.6 mmol) in dry THF (5 mL) was treated with a 1 M diethyl ether solution of allylmagnesium bromide (0.6 mL). After 5 min, a solution of 2-[2-(1-tert-butoxycarbonylpiperidin-4-yloxy)-4-(1-pyrroldinyl)phenyl]-4H-thieno[3,2-d][1,3]oxazin-4-one (100 mg, 0.2 mmol) in dry THF (5 mL) was added. The reaction was stirred overnight, concentrated to dryness, and partitioned between saturated aqueous NaHCO₃ (2 mL) and CH₂Cl₂ (5 mL). The organic layer was purified by 2 chromatographic procedures using 55/40/5 hexanes/THF/Et₃N.

The recovered solid was dissolved in CH₂Cl₂ (10 mL) with anisole (1 mL) and treated with trifluoroacetic acid (2 mL) overnight at ambient temperature. The reaction mixture was concentrated under vacuum, mixed with diethyl ether (10 mL), and sonicated for 15 min to give 87 mg of the title compound as a solid (61%).
FD-MS, m/e 492 (m+1)

EXAMPLE 18

Preparation of N-(5-Chloropyridin-2-yl)-3-[2-(piperidin-4-yloxy)-4-(pyrrolidin-1-yl)benzoylamino]thiophene-2-carboxamide Trifluoroacetate

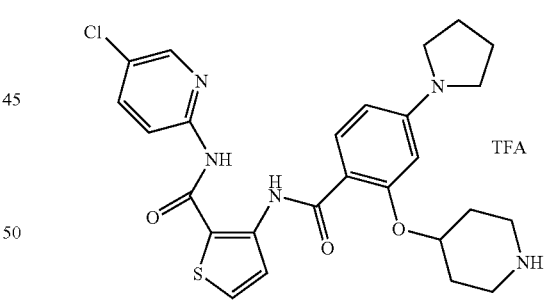

Using methods substantially equivalent to those described in Example 17-D, N-(5-chloropyridin-2-yl)-3-[2-(piperidin-4-yloxy)-4-(pyrrolidin-1-yl)benzoylamino]-thiophene-2-carboxamide trifluoroacetate was prepared in a 42% yield from 2-[2-(1-tert-butoxycarbonylpiperidin-4-yl-oxy)-4-(1-pyrroldinyl)phenyl]-4H-thieno[3,2-d][1,3]oxazin-4-one (100 mg, 0.2 mmol) and 2-amino-5-chloropyridine.
FD-MS, m/e 526 (m+1)
Analysis for C₂₅H₂₈ClN₅SO₃.CF₃COOH.0.5H₂O:
Calcd: C, 51.81; H, 4.66; N, 10.79;
Found: C, 52.15; H, 4.44; N, 10.56.

EXAMPLE 19

Preparation of N-(5-Chloropyridin-2-yl)-4-[4-(dimethyl-amino)-2-(piperidin-4-yloxy)benzoylamino]thiophene-3-carboxamide Trifluoroacetate

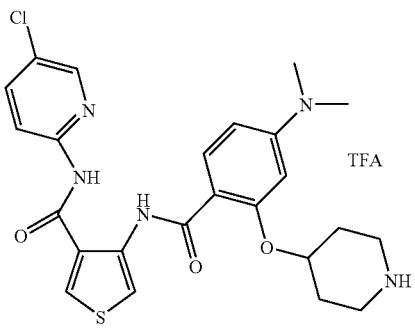

A. Methyl 2-(1-tert-Butoxycarbonylpiperidin-4-yloxy)-4-(dimethylamino)benzoate

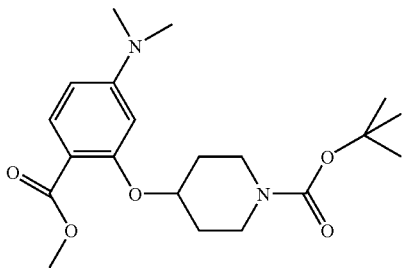

The 4-dimethylamino compound was obtained in the following preparation in which the dimethylamino group was derived from in situ decomposition of the solvent DMF: A mixture of methyl 2-(1-tert-butoxycarbonylpiperidin-4-yloxy)-4-fluorobenzoate (6.45 g, 18.25 mmol), morpholine (8 g, 91.26 mmol), $Cs_2CO_3$ (11.8 g, 36.5 mmol), and DMF (10 mL) was heated 3 days at 110° C. The reaction mixture was poured into brine (100 mL) and extracted with EtOAc (3×100 mL). The combined extracts were washed with brine (3×200 mL), dried over $MgSO_4$, and concentrated to an oil which was purified by chromatography on silica using 25% EtOAc in hexanes to give 4.1 g (59%) of product as a white solid.

$^1$NMR

FD-MS, m/e 379 (m+1)

B. 2-(1-tert-Butoxycarbonylpiperidin-4-yloxy)-4-(dimethylamino)benzoic acid

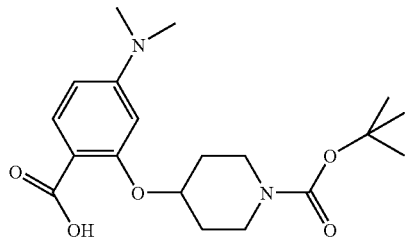

Using methods substantially equivalent to those described in Example 12-D, 2-(1-tert-butoxycarbonyl-piperidin-4-yloxy)-4-(dimethylamino)benzoic acid was prepared in a 88% yield from methyl 2-(1-tert-butoxy-carbonylpiperidin-4-yloxy)-4-(dimethylamino)benzoate.

$^1$NMR

FD-MS, m/e 364 (m+)

Analysis for $C_{19}H_{28}N_2O_5$:

Calcd: C, 62.62; H, 7.74; N, 7.69;

Found: C, 62.70; H, 7.79; N, 7.63.

C. Methyl 4-[2-(1-tert-Butoxycarbonylpiperidin-4-yloxy)-4-(dimethylamino)benzoylamino]thiophene-3-carboxylate

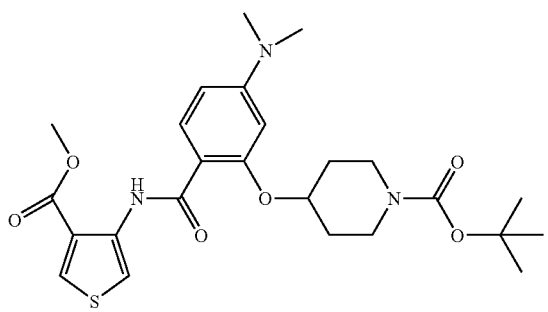

Using methods substantially equivalent to those described in Example 12-C, methyl 4-[2-(1-tert-butoxy-carbonylpiperidin-4-yloxy)-4-(dimethylamino)benzoylamino]-thiophene-3-carboxylate was prepared in a 51% yield from 2-(1-tert-butoxycarbonylpiperidin-4-yloxy)-4-(dimethylamino)benzoic acid and methyl 4-aminothiophene-3-carboxylate.

$^1$NMR

IS-MS 504 (m+1)

Analysis for $C_{25}H_{33}N_3SO_6$:

Calcd: C, 59.62; H, 6.60; N, 8.34;

Found: C, 59.67; H, 6.65; N, 8.37.

D. 2-[2-(1-tert-Butoxycarbonylpiperidin-4-yloxy)-4-(dimethylamino)phenyl]-4H-thieno[3,4-d][1,3]oxazin-4-one

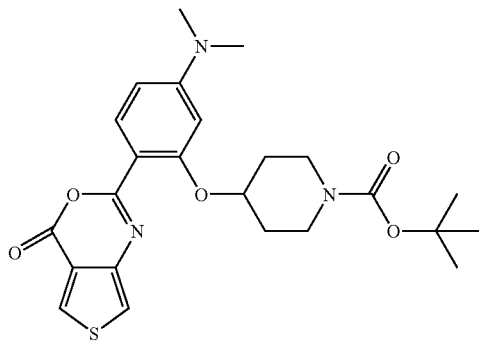

A solution of methyl 4-[2-(1-tert-butoxycarbonyl-piperidin-4-yloxy)-4-(dimethylamino)benzoylamino]thiophene-3-carboxylate (2.3 g, 4.6 mmol) in MeOH (100 mL) and THF (50 mL) was treated with a solution of 1 N aqueous NaOH (10 mL) at 60° C. for 24 h. The mixture was concentrated to dryness, mixed with brine (25 mL) and glacial acetic acid (0.65 mL), then extracted with $CHCl_3$ (2×100 mL). The extracts were dried over $MgSO_4$, cooled to 0° C. and treated with $Et_3N$ (1 g) followed by a 2 M $CH_2Cl_2$ solution of oxalyl chloride (3.5 mL). The mixture was stirred overnight, concentrated to dryness, and treated sequentially with potassium carbonate (11 g), THF (20 mL), water (20 mL), and di-tert-butyl dicarbonate (8 g). The mixture was stirred overnight, diluted with more THF (50 mL) and treated with NaCl (20 g). The organic layer was separated, dried over $MgSO_4$, and concentrated to an oil which was purified by silica chromatography using 15% EtOAc in hexanes to give 2 g of product as an oil.

IS-MS, m/e 472 (m+1)

E. N-(5-Chloropyridin-2-yl)-4-[4-(dimethylamino)-2-(piperidin-4-yloxy)benzoylamino]thiophene-3-carboxamide Trifluoroacetate Using methods substantially equivalent to those described in Example 17-D and 12-G, N-(5-chloropyridin-2-yl)-4-[4-(dimethylamino)-2-(piperidin-4-yloxy)benzoylamino]-thiophene-3-carboxamide trifluoroacetate was prepared in a 20% yield from 2-[2-(1-tert-butoxycarbonylpiperidin-4-yl-oxy)-4-(dimethylamino)phenyl]-4H-thieno[3,4-d][1,3]oxazin-4-one and 2-amino-5-chloropyridine.

[1]NMR
IS-MS 500 (m+1)
Analysis for $C_{24}H_{26}ClN_5SO_3 \cdot CF_3COOH \cdot 0.1H_2O$:
Calcd: C, 50.71; H, 4.45; N, 11.37;
Found: C, 50.62; H, 4.41; N, 11.05,

EXAMPLE 20

Preparation of N-(4-Chlorophenyl)-4-[4-(dimethylamino)-2-(piperidin-4-yloxy)benzoylamino]thiophene-3-carboxamide Trifluoroacetate

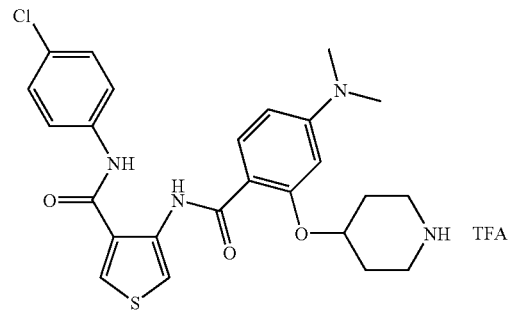

Using methods substantially equivalent to those described in Example 17-D, N-(4-chlorophenyl)-4-[4-(dimethylamino)-2-(piperidin-4-yloxy)benzoylamino]-thiophene-3-carboxamide trifluoroacetate was prepared in a 14% yield from 2-[2-(1-tert-butoxycarbonylpiperidin-4-yl-oxy)-4-(dimethylamino)phenyl]-4H-thieno[3,4-d][1,3]oxazin-4-one and 4-chloroaniline.

[1]NMR
IS-MS, m/e 499 (m+1)
Analysis for $C_{25}H_{27}ClN_4SO_3 \cdot CF_3COOH \cdot 0.1H_2O$:
Calcd: C, 52.74; H, 4.62; N, 9.11;
Found: C, 52.40; H, 4.55; N, 8.74.

EXAMPLE 21

Preparation of N-(5-Chloropyridin-2-yl)-4-[2-(piperidin-4-yloxy)-4-(pyrrolidin-1-yl)benzoylamino]thiophene-3-carboxamide Trifluoroacetate

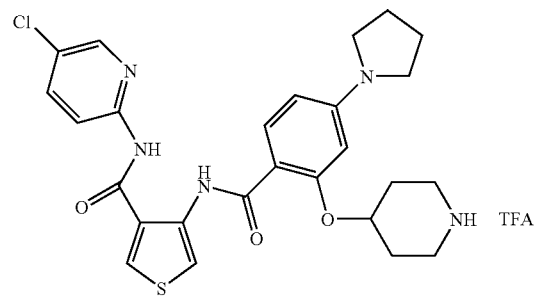

A. Methyl 4-[2-(Piperidin-4-yloxy)-4-(pyrrolidin-1-yl)-benzoylamino]thiophene-3-carboxylate

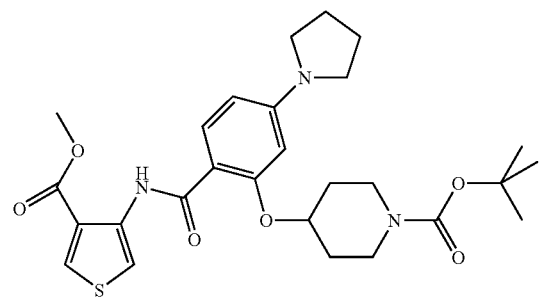

Using methods substantially equivalent to those described in Example 12-C, methyl 4-[2-(piperidin-4-yloxy)-4-(pyrrolidin-1-yl)benzoylamino]thiophene-3-carboxylate was prepared in a 67% yield from 2-(1-tert-butoxycarbonyl-piperidin-4-yloxy)-4-(pyrrolidin-1-yl)benzoic acid and methyl 4-aminothiophene-3-carboxylate.

¹NMR

FD-MS, m/e 530 (m+1)

Analysis for $C_{27}H_{35}N_3O_6S$:

Calcd: C, 61.23; H, 6.66; N, 7.93;

Found: C, 61.13; H, 6.60; N, 7.89.

B. 4-[2-(1-tert-Butoxycarbonylpiperidin-4-yloxy)-4-(pyrrolidin-1-yl)benzoylamino]thiophene-3-carboxylic Acid

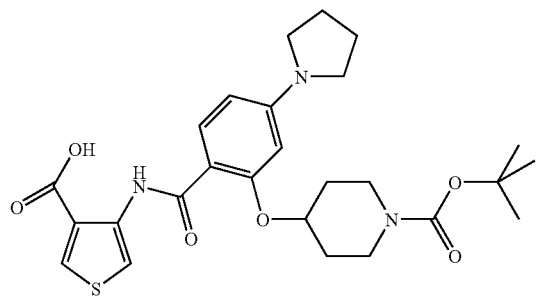

A solution of methyl 4-[2-(piperidin-4-yloxy)-4-(pyrrolidin-1-yl)benzoylamino]thiophene-3-carboxylate (4.4 g, 8.3 mmol) in EtOH (100 mL) was treated with water (100 mL) and KOH (1.92 g, 34.2 mmol). The reaction mixture was refluxed for 20 h. It was then quenched with glacial acetic acid (3 g), concentrated under vacuum, and extracted with EtOAc (3×100 mL). The extracts were dried over MgSO₄ and concentrated to give 4.1 g (7.9 mmol, 96%) of a foam.

¹NMR

FD-MS, m/e 516 (m+1)

C. 2-[2-(1-tert-Butoxycarbonylpiperidin-4-yloxy)-4-(1-pyrroldinyl)phenyl]-4H-thieno[3,4-d][1,3]oxazin-4-one

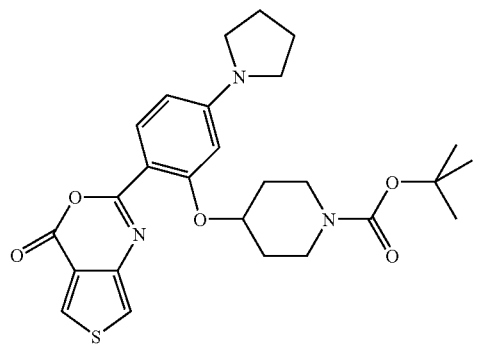

Using methods substantially equivalent to those described in Example 17-C, 2-[2-(1-tert-butoxycarbonyl-piperidin-4-yloxy)-4-(1-pyrroldinyl)phenyl]-4H-thieno[3,4-d][1,3]oxazin-4-one was prepared in a 56% yield from 4-[2-(1-tert-butoxycarbonylpiperidin-4-yloxy)-4-(pyrrolidin-1-yl)benzoylamino]thiophene-3-carboxylic acid.

¹NMR

IS-MS 498 (m+1)

Analysis for $C_{26}H_{31}N_3SO_5$:

Calcd: C, 61.64; H, 6.37; N, 8.29;

Found: C, 61.72; H, 6.23; N, 8.33.

D. 4-[2-(1-tert-Butoxycarbonylpiperidin-4-yloxy)-4-(pyrrolidin-1-yl)benzoylamino]-N-(5-chloropyridin-2-yl)-thiophene-3-carboxamide

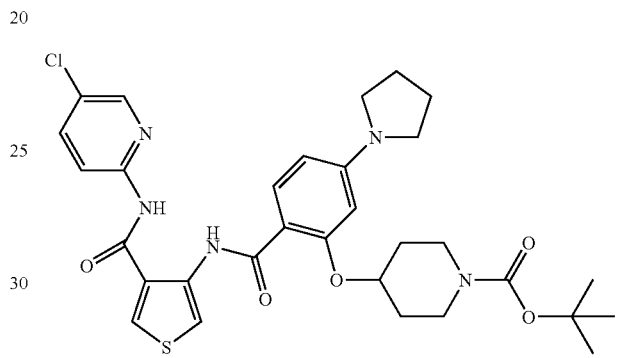

Using methods substantially equivalent to those described in Example 12-F, 4-[2-(1-tert-butoxycarbonyl-piperidin-4-yloxy)-4-(pyrrolidin-1-yl)benzoylamino]-N-(5-chloropyridin-2-yl)thiophene-3-carboxamide was prepared in a 66% yield from 2-[2-(1-tert-butoxycarbonylpiperidin-4-yloxy)-4-(1-pyrroldinyl)phenyl]-4H-thieno[3,4-d][1,3]oxazin-4-one.

¹NMR

IS-MS 626 (m+1)

Analysis for $C_{31}H_{36}ClN_5SO_5$:

Calcd: C, 59.46; H, 5.79; N, 11.18;

Found: C, 59.20; H, 5.76; N, 10.92.

E. N-(5-Chloropyridin-2-yl)-4-[2-(piperidin-4-yloxy)-4-(pyrrolidin-1-yl)benzoylamino]thiophene-3-carboxamide Trifluoroacetate Using methods substantially equivalent to those described in Example 12-G, N-(5-chloropyridin-2-yl)-4-[2-(piperidin-4-yloxy)-4-(pyrrolidin-1-yl)benzoylamino]-thiophene-3-carboxamide trifluoroacetate was prepared in a 66% yield from 4-[2-(1-tert-butoxycarbonylpiperidin-4-yl-oxy)-4-(pyrrolidin-1-yl)benzoylamino]-N-(5-chloropyridin-2-yl)thiophene-3-carboxamide.

¹NMR

IS-MS 526 (m+1)

Analysis for $C_{26}H_{28}ClN_5SO_3 \cdot CF_3CO_2H \cdot H_2O$

Calcd: C, 51.10; H, 4.75; N, 10.64;

Found: C, 51.34; H, 4.38; N, 10.49.

EXAMPLE 22

Preparation of 2-[4-tert-Butyl-2-(piperidin-4-yloxy)-benzylamino]-N-(4-chlorophenyl)pyridine-3-carboxamide

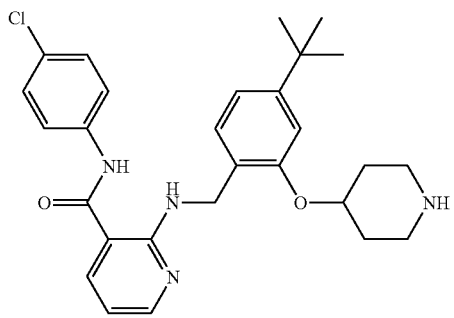

A. 4-tert-Butyl-2-(1-Boc-piperidin-4-yloxy)benzyl Alcohol

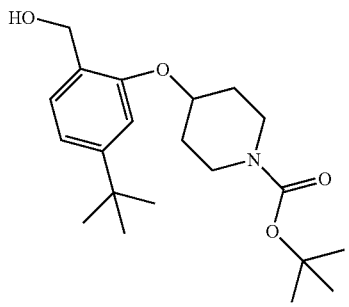

The alcohol may be prepared as follows: To a solution of borane-trimethylamine complex (1.35 mL of a 1 M solution in tetrahydrofuran) in tetrahydrofuran (3 mL) stirring at 0° C., a solution of 4-tert-butyl-2-(1-Boc-piperidine-4-yl-oxy)benzoic acid (0.51 g, 1.35 mmol) in tetrahydrofuran (7 mL) was added slowly via cannula. After the addition was complete the reaction mixture was stirred at room temperature for 4 h, then an additional amount of borane-trimethylamine complex was added (1.35 mL of a 1 M solution in tetrahydrofuran). The reaction mixture was stirred at room temperature for another 2 h. After quenching with ice, the mixture was partitioned between brine and dichloromethane. The organic layer was separated and the aqueous layer was extracted with dichloromethane (3x). The combined organic layers were dried with magnesium sulfate, filtered, and concentrated in vacuo to a residue (0.42 g, 86%) which was identified as the title compound and used directly in the next step without further purification.

$^1$NMR

FD-MS, m/e 364.1 (m+1).

B. N-[4-tert-Butyl-2-(1-Boc-piperidin-4-yloxy)benzyl]-phthalimide

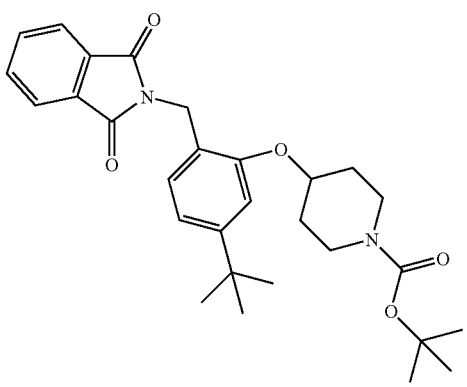

To a solution of 4-tert-butyl-2-(1-Boc-piperidin-4-yl-oxy) benzyl alcohol (0.310 g, 0.85 mmol), phthalimide (0.125 g, 0.85 mmol), and triphenylphosphine (0.224 g, 0.85 mmol) in 5 mL dry tetrahydrofuran at −10° C. was added a 0.5 M solution of diethyl azodicarboxylate in tetrahydro-furan (0.135 mL, 0.85 mmol). The reaction mixture was allowed to slowly warm to room temperature for 16 h. The solvent was removed in vacuo; and the crude material purified by chromatography over silica, using an eluent of 10-20% ethyl acetate in hexanes, to afford the substituted phthalimide (0.258 g, 61%).

$^1$NMR

FD-MS, m/e 493 (m+1)

C. 4-tert-Butyl-2-(1-Boc-piperidin-4-yloxy)benzylamine

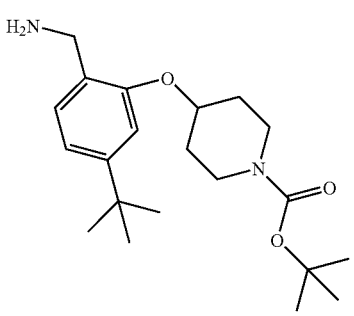

To a solution of N-[4-tert-butyl-2-(1-Boc-piperidin-4-yloxy)benzyl]phthalimide (0.243 g, 0.49 mmol) in 3 mL absolute ethanol was added hydrazine (0.062 mL, 1.98 mmol) at room temperature. The reaction mixture was stirred at room temperature for 2 h, diluted with methylene chloride; and the resulting white solid filtered off. The solvent of the filtrate was evaporated in vacuo. The remaining material was re-dissolved in a minimum amount of chloroform, sonicated, and any additional white solid filtered off. The filtrate was concentrated in vacuo to afford the amine (0.170 g, 95%).

D. N-(4-Chlorophenyl)-2-chloronicotinamide

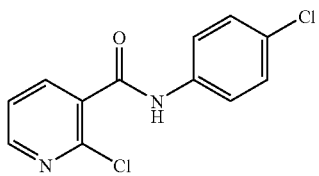

To a solution of nicotinoyl chloride (0.500 g, 2.84 mmol) in 15 mL of 1,2-dichloroethane was added 4-chloroaniline (0.432 g, 3.41 mmol) and triethylamine (0.400 mL, 2.84 mmol), respectively. The reaction mixture was stirred at room temperature for 1 h before it was washed with water (2×), brine (1×), dried over $Na_2SO_4$, and the solvent removed in vacuo. The crude material was purified by chromatography over silica, using an eluent of 2% (2 M $NH_3$ in methanol) in chloroform, to afford the amide (0.758 g, 100%).

[1]NMR

E. 2-[4-tert-Butyl-2-(1-Boc-piperidin-4-yloxy)benzyl-amino)]N-(4-chlorophenyl)pyridine-3-carboxamide

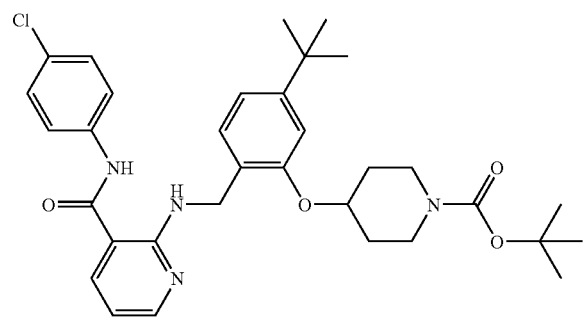

N-(4-Chlorophenyl)-2-chloronicotinamide (0.190 g, 0.70 mmol), 4-tert-butyl-2-(1-Boc-piperidin-4-yloxy)benzyl-amine (0.170 g, 0.47 mmol), and triethylamine (0.065 mL, 0.47 mmol) were placed in a pressure tube and diluted with 1 mL of absolute ethanol. The reaction vessel was heated at 100° C. for 3 days. The solvent was removed, and the remaining triethylamine was removed by azeotroping with toluene. The crude material was purified by chromatography over silica, using an eluent gradient of 20-40% ethyl acetate in hexanes to afford the named product (0.190 g, 68%).

[1]NMR

FD-MS m/e 593 (m+1)

F. 2-[4-tert-Butyl-2-(piperidin-4-yloxy)benzy-lamino)]-N-(4-chlorophenyl)pyridine-3-carboxamide To a solution of 2-[4-tert-butyl-2-(1-Boc-piperidin-4-yloxy)benzylamino)]-N-(4-chlorophenyl)pyridine-3-carboxamide (0.110 g, 0.19 mmol) in 2 mL of methylene chloride was added trifluoroacetic acid (0.14 mL, 1.86 mmol). The reaction mixture was stirred at room temperature for 3 h. The solvent was removed in vacuo, and the remaining oil was partitioned between ethyl acetate and saturated $NaHCO_3$. The aqueous layer was extracted with ethyl acetate (2×). The ethyl acetate extracts were combined and washed with brine (1×), dried over $Na_2SO_4$, and the solvent removed in vacuo. The crude material was purified by chromatography over silica, using an eluent of 5-6% (2 M $NH_3$ in methanol) in chloroform, to afford the title compound (0.920 g, 100%).

[1]NMR

FD-MS m/e 493 (m+1)

EXAMPLE 23

Preparation of 2-[2-(2-Aminoethoxy)-4-isopropyl-benzylamino]-N-(4-chlorophenyl)pyridine-3-carboxamide

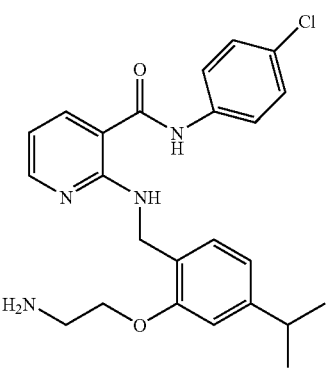

A. 4-Isopropyl-2-(methoxymethoxy)benzyl Alcohol

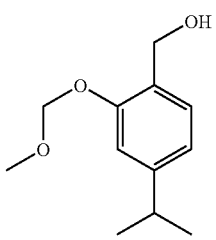

To a solution of 4-isopropyl-2-(methoxymethoxy)benzoic acid, which may be prepared as described in Exmple 6-B, (2.40 g, 11.0 mmol) and 4-methylmorpholine (1.18 mL, 11.0 mmol) in 50 mL dry tetrahydrofuran at −10° C. was added dropwise ethyl chloroformate (1.02 mL, 11.0 mmol). After stirring at −10° C. for 20 min, sodium borohydride (1.21 g, 33.0 mmol) was added all at once. Methanol (150 mL) was cautiously added dropwise. Once the vigorous evolution of carbon dioxide had significantly decreased, the remaining methanol was added. Stirring was continued for 30 min, and the reaction was quenched with 10% acetic acid in water. The volatile solvents were removed, and the remaining material was diluted with ether. The ether was extracted with saturated $NaHCO_3$ (2×), water (2×), brine (1×), and dried over $MgSO_4$.

The crude material was purified by chromatography over silica, using an eluent gradient of 10-30% ethyl acetate in hexanes, to afford the alcohol (1.16 g, 50%).

¹NMR

FD-MS m/e 193 ([m-H$_2$O]+1)

Analysis for C$_{12}$H$_{18}$O$_3$:

Calcd: C, 68.55; H, 8.63;

Found: C, 68.20; H, 9.01.

B. N-[4-Isopropyl-2-(methoxymethoxy)benzyl]phthalimide

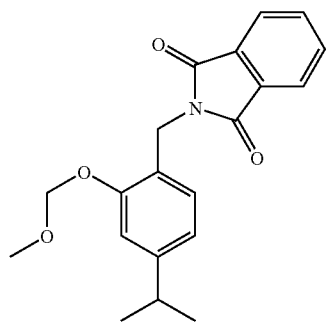

Using a procedure similar to that described in Example 22-B, the substituted phthalimide was obtained (1.50 g, 81%) from 4-isopropyl-2-(methoxymethoxy)benzyl alcohol.

¹NMR

FD-MS m/e 340 (m+1)

Analysis for C$_{20}$H$_{21}$NO$_4$:

Calcd: C, 70.78; H, 6.24; N, 4.13;

Found: C, 70.92; H, 6.10; N, 4.21.

C. 4-Isopropyl-2-(methoxymethoxy)benzylamine hydrochloride

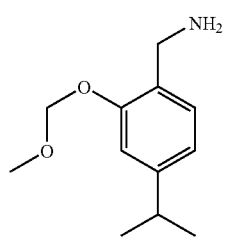

Using a procedure substantially similar to that described in Example 22-C, 4-isopropyl-2-(methoxymethoxy)-benzylamine was prepared. The hydrochloride salt was prepared by dissolving the free base in ethyl acetate and treating with an excess of 1 N HCl in ether. The solvent was removed to afford the salt (0.750 g, 81%).

¹NMR

FD-MS m/e 210 (m+1)

D. N-(4-Chlorophenyl)-2-[4-isopropyl-2-(methoxymethoxy)-benzylamino]pyridine-3-carboxamide

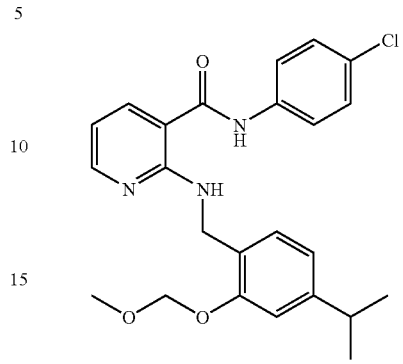

Using a procedure substantially similar to that described in Example 22-E, N-(4-chlorophenyl)-2-[4-isopropyl-2-(methoxymethoxy)benzylamino]pyridine-3-carboxamide was prepared (0.820 g, 52%) from 4-isopropyl-2-(methoxymethoxy) benzylamine and N-(4-chlorophenyl)-2-chloronicotinamide.

¹NMR

FD-MS m/e 440 (m+1)

Analysis for C$_{24}$H$_{26}$ClN$_3$O$_3$:

Calcd: C, 65.52; H, 5.96; N, 9.55;

Found: C, 65.69; H, 6.17; N, 9.35.

E. N-(4-Chlorophenyl)-2-[2-hydroxy-4-isopropyl-benzyl-amino]pyridine-3-carboxamide

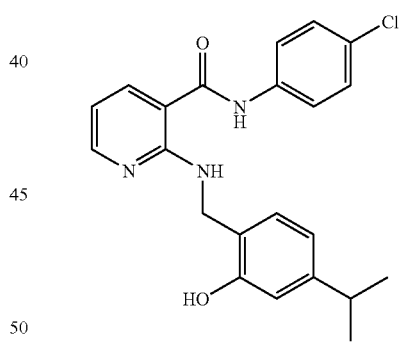

To a solution of N-(4-chlorophenyl)-2-[4-isopropyl-2-(methoxymethoxy)benzylamino]pyridine-3-carboxamide (0.670 g, 1.52 mmol) in trifluoroacetic acid was added 4 mL of water. The reaction mixture was stirred at room temperature for 5 h. The volatile solvent was removed in vacuo, and the remaining aqueous solution was neutralized with 1 N NaOH. The aqueous layer was extracted with ethyl acetate (2×). The ethyl acetate was then washed with brine (1×), dried over Na$_2$SO$_4$ and the solvent removed in vacuo. The crude material was purified by chromatography over silica, using an eluent gradient of 10-30% tetrahydrofuran in hexanes, to afford the product alcohol (0.420 g, 70%).

¹NMR

FD-MS m/e 396 (m+1)

F. 2-[2-(N-Boc-Aminoethoxy)-4-isopropylbenzy-lamino]-N-(4-chlorophenyl) pyridine-3-carboxamide

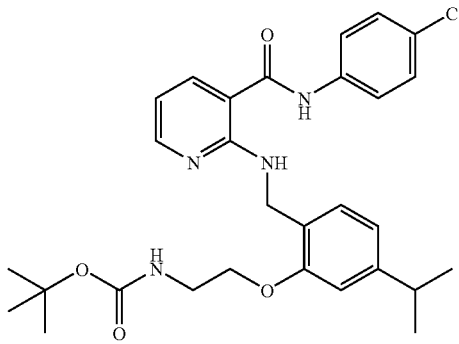

To a solution of N-(4-chlorophenyl)-2-[2-hydroxy-4-isopropylbenzylamino]pyridine-3-carboxamide (0.050 g, 0.13 mmol), triphenylphosphine (0.033 g, 0.13 mmol) and N-Boc-ethanolamine (0.018 mg, 0.11 mmol) in 0.3 mL tetrahydrofuran at −10° C. was added a solution of diethyl azodicarboxylate (0.02 mL, 0.13 mmol) in 0.3 mL tetrahydrofuran. The reaction was stirred at room temperature for 3 days. The solvent was removed in vacuo; and the crude material was purified by chromatography over silica, using an eluent gradient of 20-30% ethyl acetate in hexanes, to afford the named product (0.02 g, 30%).

[1]NMR
FD-MS m/e 539 (m+1)

G. 2-[2-(2-Aminoethoxy)-4-isopropylbenzylamino]-N-(4-chlorophenyl)pyridine-3-carboxamide 2-[2-(N-Boc-Aminoethoxy)-4-isopropylbenzylamino]-N-(4-chlorophenyl)pyridine-3-carboxamide (0.02 g, 0.04 mmol) was dissolved in 2 mL of a 1:3 mixture of trifluoroacetic aicd:methylene chloride. The reaction mixture was stirred at room temperature for 30 min. The solvent was removed, and the material was purified by ion exchange chromatography to afford the title compound (0.014 g, 88%) as the free base.

[1]NMR
FD-MS m/e 439 (m+1)

EXAMPLE 24

Preparation of 2-[2-(3-Aminopropoxy)-4-isopropyl-benzyl-amino)]-N-(4-chlorophenyl)pyridine-3-carboxamide

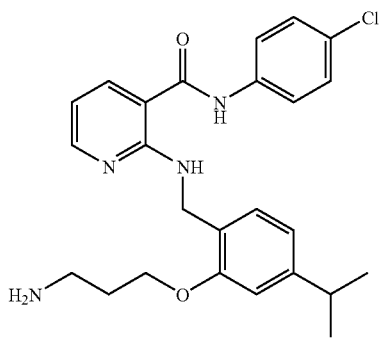

A. 2-[2-(N-Boc-3-Aminopropoxy)-4-isopropylbenzylamino)]-N-(4-chlorophenyl)pyridine-3-carboxamide

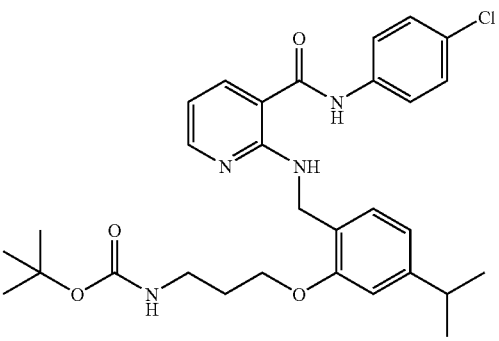

Using a procedure substantially similar to that described in Example 23-F, 2-[2-(N-Boc-3-aminopropoxy)-4-isopropyl-benzylamino)]-N-(4-chlorophenyl)pyridine-3-carboxamide was prepared (0.02 g, 25%) from 2-[2-hydroxy-4-isopropyl-benzylamino]-N-(4-chlorophenyl)pyridine-3-carboxamide and N-Boc-3-aminopropanol.

[1]NMR
FD-MS m/e 553 (m+1)

B. 2-[2-(3-Aminopropoxy)-4-isopropylbenzy-lamino)]-N-(4-chlorophenyl)pyridine-3-carboxamide Using a procedure substantially similar to that described in Example 23-G, 2-[2-(3-aminopropoxy)-4-isopropylbenzy-lamino)]-N-(4-chlorophenyl)pyridine-3-carboxamide was prepared (0.015 g, 94%) from 2-[2-(N-Boc-3-aminopropoxy)-4-isopropylbenzylamino)]-N-(4-chlorophenyl)-pyridine-3-carboxamide.

[1]NMR
FD-MS, m/e 453 (m+1)

EXAMPLE 25

Preparation of 4-[4-tert-Butyl-2-(piperidin-4-yloxy)benzoyl-amino]-N-(5-chloropyridin-2-yl)pyridine-3-carboxamide Trifluoroacetate

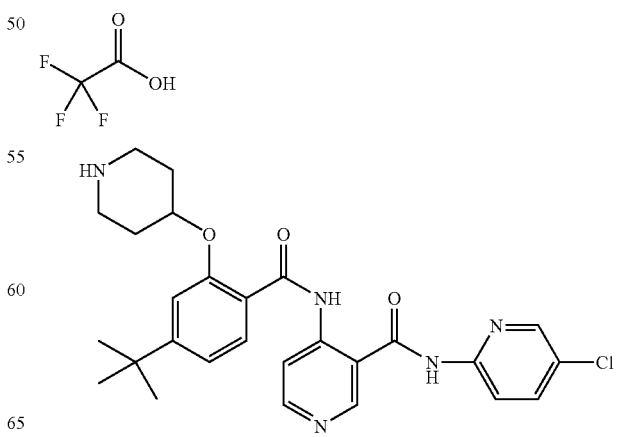

A. 4-(Boc-amino)pyridine

To a stirring solution of 4-aminopyridine (15 g, 159 mmol) and triethylamine (24 mL, 175 mmol) in DMF (300 mL) was added di-t-butyl dicarbonate (38 g, 175 mmol). After stirring overnight, the solvent was removed in vacuo. The residue was dissolved in ethyl acetate (500 mL); and the solution was washed with satd aq sodium bicarbonate, water and then brine. The organic phase was then dried with $MgSO_4$, filtered and concentrated in vacuo to a volume of about 100 mL. The mixture was then sonicated and the precipitate was filtered and dried in vacuo to give 9.52 g (31%) of the title compound. To the mother liquor was added about 50 g of silica gel and the mixture was concentrated in vacuo. The resulting dry pack was loaded onto a silica gel column prepared with a solution of 50% ethyl acetate in 5 hexanes and eluted with 20% ethyl acetate in dichloromethane, followed by a step gradient of 50% ethyl acetate in hexanes through ethyl acetate. The product containing fractions were combined and concentrated in vacuo to give another 16.16 g (52%) of the title compound.

$^1$NMR

IS-MS, m/e 195.3 (m+1)

B. 4-(Boc-amino)pyridine-3-carboxylic Acid

To a stirring solution of 4-(Boc-amino)pyridine (1.027 g, 5.30 mmol) in THF at −36° C. (internal temperature) was added a 1.7 M solution of t-butyl lithium in pentane (6.5 mL, 11 mmol), and the rate of addition was controlled so as to keep the internal temperature below −28° C. After an additional hour (temperature kept between −30° C. and −50° C.) carbon dioxide (g) was bubbled through the solution and the cold bath was removed. After about 15 min, the mixture was poured into ice water and the aqueous phase was washed with dichloromethane. The pH was adjusted to 4-5 with citric acid, and the resulting precipitate was washed with dichloromethane and methanol and dried in vacuo to give the title compound (0.811 g, 64%) as an off-white solid.

$^1$NMR

IS-MS, m/e 239.0 (m+1)

Analysis for $C_{11}H_{14}N_2O_4$:

Calcd: C, 55.46; H, 5.92; N, 11.76;

Found: C, 55.73; H, 6.07; N, 11.75.

C. Methyl 4-(Boc-amino)pyridine-3-carboxylate

To a stirring suspension of 4-(Boc-amino)pyridine-3-carboxylic acid (1.04 g, 4.37 mmol) in methanol (3.5 mL) was added a 2 M solution of (trimethylsilyl)diazomethane in hexanes (3.5 mL, 7 mmol). After 15 min, acetic acid was added and the solvents were removed in vacuo. The residue was chromatographed over silica gel, eluting with a step gradient of 20% ethyl acetate in hexanes through 70% ethyl acetate in hexanes. The product containing fractions were combined and concentrated in vacuo to give the title compound (0.894 g, 81%) as a white solid.

$^1$NMR

D. Methyl 4-aminopyridine-3-carboxylate

Methyl 4-(Boc-amino)pyridine-3-carboxylate (2.38 g, 9.4 mmol) was dissolved in TFA (20 mL) and the solution was allowed to stir for 45 min. The solvent was removed in vacuo and the residue was partitioned between 25% isopropanol in chloroform and satd aq sodium bicarbonate. The layers were separated and the aqueous phase was extracted again with 25% isopropanol in chloroform. The combined organic extracts were dried ($MgSO_4$), filtered and concentrated in vacuo to give a solid which was washed with diisopropyl ether and dried in vacuo to give the title compound (1.327 g, 92%) as an off-white solid.

$^1$NMR

IS-MS, m/e 153.1 (m+1)

Analysis for $C_7H_8N_2O_2$:

Calcd: C, 55.26; H, 5.30; N, 18.41;

Found: C, 55.31; H, 5.36; N, 18.42.

E. Methyl 4-tert-Butyl-4-[2-(1-Boc-piperidin-4-yloxy)-benzoylamino]pyridine-3-carboxylate To a stirring suspension of methyl 4-aminopyridine-3-carboxylate (0.10 g, 0.659 mmol) in dichloromethane (1 mL) was added a solution of 4-tert-butyl-2-(1-Boc-piperidin-4-yloxy)benzoyl chloride (1.3 mmol) in dichloromethane (6 mL), followed by N,N-diisopropylethylamine (0.15 mL, 0.8 mmol) and 4-N,N-dimethylaminopyridine (0.0084 g, 0.068 mmol). After stirring overnight, the solution was diluted with ethyl acetate and washed three times with satd aq $NaHCO_3$. The combined aq phase was back extracted with ethyl acetate and the combined organic phase was dried with $MgSO_4$, filtered and concentrated in vacuo. The residue was chromatographed over silica gel, eluting with a gradient of 30% ethyl acetate in hexanes through 100% ethyl acetate. The product containing fractions were combined and concentrated in vacuo to give the title compound (0.223 g, 66%) as a thick yellow syrup.

$^1$NMR

IS-MS, m/e 512.3 (m+1)

F. 4-[4-tert-Butyl-2-(1-Boc-piperidin-4-yloxy)benzoyl-amino]pyridine-3-carboxylic acid To a stirring solution of methyl 4-[4-tert-butyl-2-(1-Boc-piperidin-4-yloxy)benzoylamino]pyridine-3-carboxylate (0.192 g, 0.376 mmol) in tetrahydrofuran (4 mL) was added water (1 mL), followed by a 1 M solution of LiOH in water (0.4 mL, 0.4 mmol). After stirring overnight, the solution was partially concentrated in vacuo and then diluted with water and washed with diethyl ether. The pH of the aq phase was then adjusted to 4-5 by the addition of citric acid. The resulting precipitate was dried in vacuo to give the title compound (0.15 g, 80%) as a white solid.

$^1$NMR

IS-MS, m/e 508.1 (m+1)

G. 2-[4-tert-Butyl-2-(1-Boc-piperidin-4-yloxy)phenyl]-4H-pyrido[4,3-d][1,3]oxazin-4-one To a stirring solution of 4-[4-tert-butyl-2-(1-Boc-piperidin-4-yloxy)benzoylamino]pyridine-3-carboxylic acid (0.15 g, 0.30 mmol) in DMF (5 mL) was added 1-[3-(dimethylamino)propyl]-3-ethylcarbodiimide hydrochloride (0.077 g, 0.39 mmol). After stirring overnight, the solvent was removed in vacuo and the residue was dissolved in ethyl acetate and washed twice with ice water/brine. The combined aq phase was back extracted with ethyl acetate and the combined organic phase was dried with $MgSO_4$, filtered and concentrated in vacuo to give the title compound (0.121 g, 84%) as a light yellow foam.

$^1$NMR

H. 4-[4-tert-Butyl-2-(1-Boc-piperidin-4-yloxy)benzoyl-amino]-N-(5-chloropyridin-2-yl)pyridine-3-carboxamide To a stirring solution of 2-amino-5-chloropyridine (0.055 g, 0.42 mmol) in THF (5 mL) at 0° C., was added a 1.0 M solution of allylmagnesium chloride in diethyl ether (0.4 mL, 0.4 mmol). To this solution was then added a solution of 2-[4-tert-butyl-2-(1-Boc-piperidin-4-yloxy)-phenyl]-4H-pyrido[4,3-d][1,3]oxazin-4-one (0.12 g, 0.25 mmol) in THF (3 mL). After several hours, the solution was diluted with ethyl acetate and washed twice with brine. The organic phase was then dried with $MgSO_4$, filtered and concentrated in vacuo to give a white solid which was washed with diethyl ether and dried in vacuo to give the title compound (0.11 g, 70%).

$^1$NMR
IS-MS, m/e 608.2 (m+1)
Analysis for $C_{32}H_{38}ClN_5O_5$:
Calcd: C, 63.20; H, 6.30; N, 11.52;
Found: C, 63.10; H, 6.39; N, 11.25.

I. 4-[4-tert-Butyl-2-(piperidin-4-yloxy)benzoylamino]-N-(5-chloropyridin-2-yl)pyridine-3-carboxamide trifluoroacetate To a stirring solution of 4-[4-tert-butyl-2-(1-Boc-piperidin-4-yloxy)benzoylamino]-N-(5-chloropyridin-2-yl)pyridine-3-carboxamide (0.099 g, 0.163 mmol) and anisole (0.1 mL) in dichloromethane (5 mL) was added TFA (0.5 mL). After 2 h, the solvent was removed in vacuo and the residue was suspended in toluene and concentrated in vacuo. The residue was then diluted with diethyl ether and concentrated in vacuo. Finally, the residue was again diluted with diethyl ether with vigorous stirring to yield a solid precipitate, which was filtered and washed with diethyl ether and dried in vacuum to give the title compound (0.089 g, 88%) as a white solid.

$^1$NMR
IS-MS, m/e 508.3 (m+1)
Analysis for $C_{27}H_{30}ClN_5O_3 \cdot 1.9$ TFA:
Calcd: C, 51.05; H, 4.44; N, 9.66; F, 14.94;
Found: C, 50.93; H, 4.48; N, 9.44; F, 14.77.

EXAMPLE 26

Preparation of N-(5-Chloropyridin-2-yl)-3-[4-(2-fluoro-ethoxy)-2-(piperidin-4-yloxy)benzoylamino]pyridine-2-carboxamide

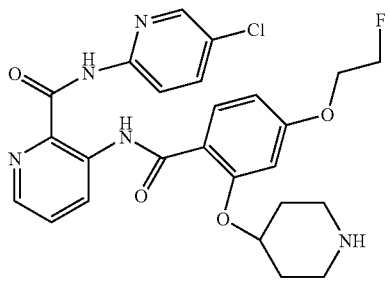

A. Methyl 4-(2-Fluoroethoxy)-2-hydroxybenzoate

A mixture of methyl 2,4-dihydroxybenzoate (5.04 g, 30 mmol), 1-bromo-2-fluoroethane (4.18 g, 2.46 mL, 33 mmol), potassium carbonate (4.55 g, 33 mmol) and potassium iodide (1 g) in DMF (20 mL) was heated overnight at 55-60° C. before it was poured into water (150 mL). The resulting white precipitate was filtered, redissolved in dichloromethane, dried ($MgSO_4$), concentrated and diluted with hexane to afford the ether in two crops (1.30 g and 2.19 g). The first crop was characterized:

EI-MS, 214.03 (m)
Analysis for $C_{10}H_{11}OF_4$:
Calcd: C, 56.08; H, 5.18;
Found: C, 56.07; H, 5.27.

B. Methyl 2-(1-tert-Butoxycarbonylpiperidin-4-yloxy)-4-(2-fluoroethoxy)benzoate Using a procedure similar to that of Example 6-D, methyl 4-(2-fluoroethoxy)-2-hydroxybenzoate (3.6 g, 17.8 mmol), 1-tert-butoxycarbonyl-4-hydroxypiperidine (3.58 g, 17.8 mmol), and triphenylphosphine (5.60 g, 21.4 mmol) in THF (75 mL) is treated with diethyl azodicarboxylate (3.60 g, 17.8 mmol) in THF (15 mL) to afford the crude product (7.28 g) which is used without further purification.

C. 2-(1-tert-Butoxycarbonylpiperidin-4-yloxy)-4-(2-fluoroethoxy)benzoic Acid Using a procedure similar to that of Example 6-E, methyl 2-(1-tert-butoxycarbonylpiperidin-4-yloxy)-4-(2-fluoroethoxy)benzoate (7.28 g) is hydrolyzed using $LiOH \cdot H_2O$ (1.78 g, 2.2 equivalents), water (20 mL) and THF (60 mL) at 60-65° C. to afford the acid (2.76 g, 40%).

D. N-(5-Chloropyridin-2-yl)-3-[4-(2-fluoroethoxy)-2-(piperidin-4-yloxy)benzoylamino]pyridine-2-carboxamide Using a procedure similar to that of Example 1-I, 2-(1-tert-butoxycarbonylpiperidin-4-yloxy)-4-(2-fluoro-ethoxy)benzoic acid (0.767 g, 2 mmol) is treated with oxalyl chloride (0.193 mL, 2.2 mmol) and pyridine (1.78 mL, 22 mmol) in dichloromethane (50 mL) to afford the acid chloride.

The acid chloride in dichloromethane (25 mL) is cooled in an ice bath and treated with 3-amino-N-(5-chloropyridin-2-yl)pyridine-2-carboxamide (0.465 g, 2 mmol) in dichloromethane (25 mL) and allowed to warm to room temperature overnight to afford 3-[2-(1-tert-butoxycarbonylpiperidin-4-yloxy)-4-(2-fluoroethoxy)benzoylamino]-N-(5-chloropyridin-2-yl)pyridine-2-carboxamide.

The concentrated crude amide is taken up in ethyl acetate and partitioned into water by the addition of 5 N HCl and hexane. The acidic aqueous phase is separated and basified with aqueous potassium carbonate to afford a precipitate. The precipitate is collected, washed with water and dried under vacuum to provide the title compound (0.286 g).

EXAMPLE 27

Preparation of N-(5-Chloropyridin-2-yl)-3-[4-(2-fluoro-ethoxy)-2-(piperidin-3-ylmethoxyoxy)benzoylamino]pyridine-2-carboxamide

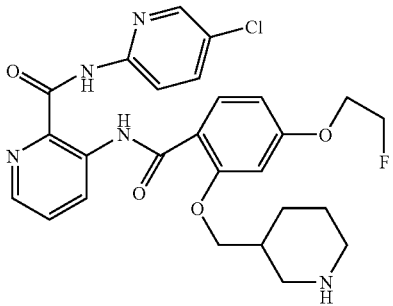

A. 2-(1-tert-Butoxycarbonylpiperidin-3-ylmethoxy)-4-(2-fluoroethoxy)benzoic Acid Using a procedure similar to that of Example 26-B, 4-(2-fluoroethoxy)-2-hydroxybenzoate (2.6 g, 12.8 mmol), 1-tert-butoxycarbonylpiperidin-3-ylmethanol (2.76 g, 12.8 mmol), and triphenylphosphine (4.02 g, 15.4 mmol) in THF (50 mL) is treated with diethyl azodicarboxylate (2.59 g, 12.8 mmol) in THF to afford methyl 2-(1-tert-butoxycarbonyl-piperidin-3-ylmethoxy)-4-(2-fluoroethoxy)benzoate (6.35 g) which is used without further purification.

Using a procedure similar to that of Example 26-C, the ester is hydrolyzed using LiOH.H$_2$O (1.50 g, 2.2 equivalents), water (20 mL) and THF (60 mL) to afford the acid (2.93 g, 59% for the two steps).

B. N-(5-Chloropyridin-2-yl)-3-[4-(2-fluoroethoxy)-2-(piperidin-3-ylmethoxy)benzoylamino]pyridine-2-carboxamide Using a procedure similar to that of Example 26-D, 2-(1-tert-butoxycarbonylpiperidin-3-ylmethoxy)-4-(2-fluoroethoxy)benzoic acid (0.767 g, 2 mmol) is converted into the acid chloride.

Using a procedure similar to that of Example 26-D, the acid chloride is treated with 3-amino-N-(5-chloropyridin-2-yl)pyridine-2-carboxamide (0.465 g, 2 mmol). The crude reaction mixture is shaken with cold 2 N HCl; and the resulting organic phase was washed with aqueous potassium carbonate, dried (MgSO$_4$) and evaporated to afford 3-[2-(1-tert-butoxycarbonylpiperidin-3-ymethoxy)-4-(2-fluoroethoxy)benzoylamino]-N-(5-chloropyridin-2-yl)-pyridine-2-carboxamide which is used without further purification.

The above amide in dichloromethane (5 mL) is treated with TFA (5 mL) for 5 h at room temperature. After evaporation, the resulting solid is triturated with hexane, and precipitated with ethyl ether-hexane. The resulting solid is redissolved in ethyl acetate and partitioned into 5 N HCl, with addition of hexane to the organic phase. The The acidic aqueous phase is separated, basified with aqueous potassium carbonate, and extracted with ethyl acetate. The organic phase is dried (MgSO$_4$) and evaporated to a solid which is crystallized from dichloromethane-hexane to provide the title compound (0.169 g, 16% overall).

$^1$NMR

MS

EXAMPLE 28

Preparation of 3-[2-(3-Amino-2,2-dimethylpropoxy)-4-(2-fluoroethoxy)benzoylamino]-N-(5-chloropyridin-2-yl)-pyridine-2-carboxamide Bis(trifluoroacetate)

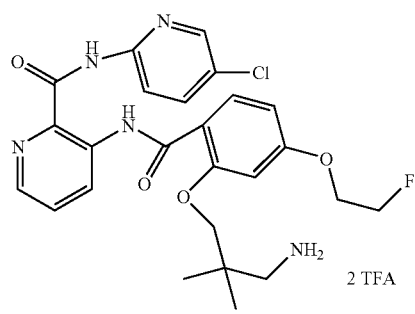

A. 2-(3-tert-Butoxycarbonylamino-2,2-dimethylpropoxy)-4-(2-fluoroethoxy)benzoic Acid Using a procedure similar to that of Example 26-B, methyl 4-(2-fluoroethoxy)-2-hydroxybenzoate (3.6 g, 17.8 mmol) is alkylated with 3-tert-butoxycarbonylamino-2,2-dimethylpropanol (3.62 g, 17.8 mmol) to afford methyl 2-(3-tert-butoxycarbonylamino-2,2-dimethylpropoxy)-4-(2-fluoroethoxy)benzoate (5.12 g).

Using a procedure similar to that of Example 26-C, the ester (5.12 g) is hydrolyzed to afford the acid (2.44 g, 34% for the two steps).

B. 3-[2-(3-Amino-2,2-dimethylpropoxy)-4-(2-fluoroethoxy)-benzoylamino]-N-(5-chloropyridin-2-yl) pyridine-2-carboxamide Trifluoroacetate Using a procedure similar to that of Example 26-D, 2-(3-tert-butoxycarbonylamino-2,2-dimethylpropoxy)-4-(2-fluoroethoxy)benzoic acid (0.798 g, 2 mmol) is converted into the acid chloride.

Using a procedure similar to those of Examples 1-1 and 26-D, the acid chloride is treated with 3-amino-N-(5-chloropyridin-2-yl)pyridine-2-carboxamide (0.465 g, 2 mmol) to afford 3-[2-(3-tert-butoxycarbonylamino-2,2-dimethyl-propoxy)-4-(2-fluoroethoxy)benzoylamino]-N-(5-chloropyridin-2-yl)pyridine-2-carboxamide (0.320 g, 27%) after purification by elution from silica gel.

Using a procedure similar to that of Example 1-J, the above compound was treated with 1:1 TFA:dichloromethane, to afford, after evaporation, the title compound as the bis(trifluoroacetate) salt (0.260 g, 67%).

$^1$NMR

MS

EXAMPLE 29

Preparation of 3-[2-(cis-4-Aminocyclohexyloxy)-4-(2-fluoro-ethoxy)benzoylamino]-N-(5-chloropyridin-2-yl)pyridine-2-carboxamide Tris(trifluoroacetate)

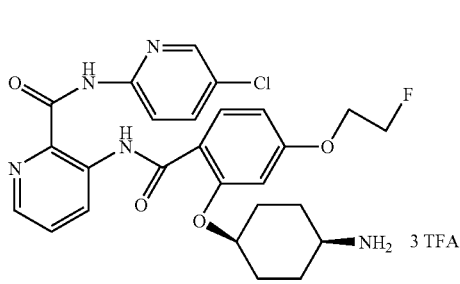

A. 2-(cis-4-tert-Butoxycarbonylaminocyclohexyloxy)-4-(2-fluoroethoxy)benzoic Acid Using a procedure similar to that of Example 6-D, methyl 4-(2-fluoroethoxy)-2-hydroxybenzoate (5.0 g, 24.75 mmol), trans-4-tert-butoxycarbonylaminocyclohexanol (5.02 g, 24.75 mmol), and triphenylphosphine (1.2 equivalents) in THF (125 mL) is treated with diethyl azodicarboxylate (1.3 equivalents) in THF (25 mL). After having stirred overnight at room temperature, the reaction mixture was heated 8 h at 40-50° C., then stirred overnight at room temperature. The crude product was isolated by elution from silica gel with a gradient of 0 to 40% ethyl acetate in hexane to afford crude methyl 2-(cis-4-tert-butoxycarbonylaminocyclohexyloxy)-4-(2-fluoroethoxy)benzoate (7.30 g), which is used without further purification.

Using a procedure similar to that of Example 26-C, the above crude ester (7.30 g) is hydrolyzed to afford the acid (0.87 g, 8.8%), which is used without further purification.

B. 3-[2-(cis-4-Aminocyclohexyloxy)-4-(2-fluoroethoxy)-benzoylamino]-N-(5-chloropyridin-2-yl)pyridine-2-carboxamide Trifluoroacetate Using a procedure similar to that of Example 26-D, 3-[2-(cis-4-tert-butoxycarbonylaminocyclohexyloxy)-4-(2-fluoroethoxy)benzoic acid (0.87 g, 2.19 mmol) is converted into the acid chloride.

Using a procedure similar to that of Example 26-D, the acid chloride is treated with 3-amino-N-(5-chloropyridin-2-yl)pyridine-2-carboxamide (0.510 g, 2.19 mmol) to afford 3-[2-(cis-4-tert-butoxycarbonylaminocyclohexyloxy)-4-(2-fluoroethoxy)benzoylamino]-N-(5-chloropyridin-2-yl)-pyridine-2-carboxamide (0.415 g, 30%).

Using a procedure similar to that of Example 1-J, the above compound was treated with 1:1 TFA:dichloromethane (3 mL each), to afford, after filtration of some insoluble material and evaporation, the title compound as the tris(trifluoroacetate) salt (0.374 g, 73%).

EXAMPLE 30

Preparation of 3-[2-(3-Aminopropoxy)-4-(2-fluoroethoxy)-benzoylamino]-N-(5-chloropyridin-2-yl)pyridine-2-carboxamide

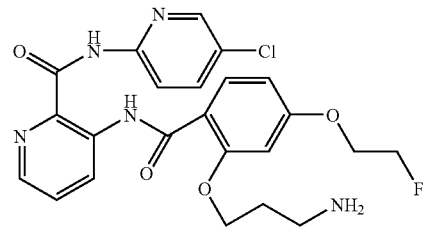

A. 2-(3-tert-Butoxycarbonylaminopropoxy)-4-(2-fluoro-ethoxy)benzoic Acid

Using a procedure similar to that of Example 6-D, methyl 4-(2-fluoroethoxy)-2-hydroxybenzoate (5.0 g, 24.75 mmol)-, 3-tert-butoxycarbonylaminopropanol (4.13 mL, 24.75 mmol), and triphenylphosphine (1.2 equivalents) in THF (125 mL) is treated with diethyl azodicarboxylate (1.3 equivalents) in THF (25 mL). The crude product is isolated by elution from silica gel with a gradient of 0 to 40% ethyl acetate in hexane to afford methyl 2-(3-tert-butoxycarbonylaminopropoxy)-4-(2-fluoroethoxy)benzoic acid (6.18 g), which is used without further purification.

The above ester is hydrolyzed using LiOH.H$_2$O (6.99 g, 10 equivalents), water (10 mL) and THF (30 mL) by heating the reaction mixture 18 h at 65° C. After evaporation of the organic solvent, the residue is diluted with water (200 mL) and partitioned with a mixture of ethyl acetate (150 mL) and hexane (100 mL). The aqueous phase is acidified and then made basic with aqueous potassium carbonate during the partitioning. The resulting basic aqueous phase is washed with 1:1 ethyl acetate:hexane (250 mL), acidified with 5 N HCl, and extracted with ethyl acetate. The ethyl acetate solution is dried (MgSO$_4$) and evaporated to afford the acid (3.89 g, 44%) as a solid.

B. 3-[2-(3-Aminopropoxy)-4-(2-fluoroethoxy)benzoylamino]-N-(5-chloropyridin-2-yl)pyridine-2-carboxamide Trifluoroacetate Using a procedure similar to that of Example 26-D, 2-(3-tert-butoxycarbonylaminopropoxy)-4-(2-fluoroethoxy)-benzoic acid (1.43 g, 4 mmol) is converted into the acid chloride.

Using a procedure similar to that of Example 26-D, the acid chloride is treated with 3-amino-N-(5-chloropyridin-2-yl)pyridine-2-carboxamide (0.931 g, 4 mmol). The reaction mixture is diluted with dichloromethane and washed with cold water. Evaporation, followed by isolation of the crude product from silica gel, eluting with a gradient of 0-40% ethyl acetate in hexane, and crystallization from dichloromethane-hexane affords a first crop of 3-[2-(3-tert-butoxycarbonylaminopropoxy)-4-(2-fluoroethoxy)benzoyl-amino]-N-(5-chloropyridin-2-yl)pyridine-2-carboxamide (0.325 g). Chromatography of the mother liquor provides a further 0.110 g of amide (0.435 g, 15.5% for two steps).

Using a procedure similar to that of Example 1-J, the above compound (0.4 g) was treated with 1:1 TFA:dichloromethane (2 mL each), to afford the bis(trifluoroacetate) salt (0.378 g).

C. 3-[2-(3-Aminopropoxy)-4-(2-fluoroethoxy)benzoylamino]-N-(5-chloropyridin-2-yl)pyridine-2-carboxamide The above salt was converted into the free base using potassium carbonate solution and ether. The title compound (0.07 g, 19.4%) was obtained by evaporation and crystallization from dichloromethane-hexane.

EXAMPLE 31

Preparation of N-(5-Chloropyridin-2-yl)-3-[2-(piperidin-4-yloxy)-4-(2,2,2-trifluoroethoxy)-benzoylamino]pyridine-2-carboxamide Bis(Trifluoroacetate)

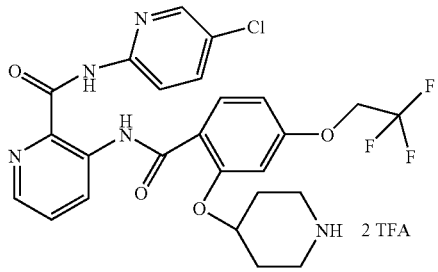

A. Methyl 2-Hydroxy-4-(2,2,2-trifluoroethoxy)benzoate

A solution of methyl 2,4-dihydroxybenzoate (5.04 g, 30 mmol) in hexamethylphosphorous triamide (HMPT, 30 mL) under nitrogen was treated with sodium hydride (50% suspension, 1.44 g, 30 mmol) to form the phenolate salt before the addition of 2,2,2-trifluoroethyl methanesulfonate (4.24 mL, 36 mmol). The reaction mixture was heated overnight at 140° C. before it was poured into brine (300 mL). The resulting mixture was extracted with ethyl acetate (200 mL); and the organic phase was washed with water (300 mL), dried (MgSO$_4$) and evaporated. The residue was purified by HPLC over silica gel, eluting with a gradient of 0-30% ethyl acetate in hexane. The product containing fractions were variously combined and concentrated before crystallization from dichloromethane-hexane (or, for the mother liquors, from hexane) to provide the ether in several crops as a solid (2.12 g, 28%).

B. 2-(1-tert-Butoxycarbonylpiperidin-4-yloxy)-4-(2,2,2-trifluoroethoxy)benzoic Acid Using a procedure similar to that of Example 26-B, methyl 2-hydroxy-4-(2,2,2-trifluoroethoxy)benzoate (2.0 g, 7.99 mmol) is alkylated with 1-tert-butoxycarbonyl-4-hydroxypiperidine (1.61 g, 7.99 mmol) to afford methyl 2-(1-tert-butoxycarbonylpiperidin-4-yloxy)-4-(2,2,2-trifluoroethoxy)benzoate (2.86 g).

Using a procedure similar to that of Example 26-C, the ester (2.86 g) is hydrolyzed to afford the acid (1.43 g, 43% for the two steps).

C. N-(5-Chloropyridin-2-yl)-3-[2-(piperidin-4-yloxy)-4-(2,2,2-trifluoroethoxy)-benzoylamino]pyridine-2-carboxamide Trifluoroacetate Using a procedure similar to that of Example 26-D, 2-(1-tert-butoxycarbonylpiperidin-4-yloxy)-4-(2,2,2-trifluoroethoxy)benzoic acid (0.75 g, 1.79 mmol) is converted into the acid chloride.

Using a procedure similar to that of Example 26-D, the acid chloride is treated with 3-amino-N-(5-chloropyridin-2-yl)pyridine-2-carboxamide (0.416 g, 1.79 mmol) to afford 3-[2-(1-tert-butoxycarbonylpiperidin-4-yloxy)-4-(2,2,2-trifluoroethoxy)benzoylamino]-N-(5-chloropyridin-2-yl)pyridine-2-carboxamide (0.407 g, 35% for two steps) after crystallization from dichloromethane-hexane.

Using a procedure similar to that of Example 1-J, the above compound was treated with 1:1 TFA:dichloromethane (4 mL each), to afford, after filtration of some insoluble material and evaporation, the title compound as the bis(trifluoroacetate) salt (0.386 g, 28%).
$^1$NMR
MS

EXAMPLE 32

Preparation of N-(5-Chloropyridin-2-yl)-3-[4-(2-methoxy-ethoxy)-2-(piperidin-4-yloxy)benzoylamino]pyridine-2-carboxamide Bis(trifluoroacetate)

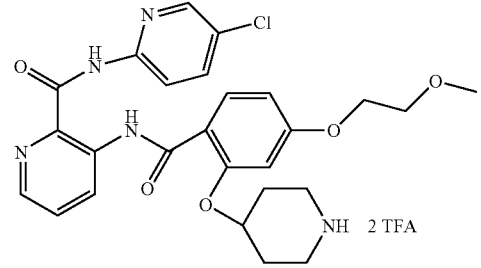

A. Methyl 2-Hydroxy-4-(2-methoxyethoxy)benzoate

A mixture of methyl 2,4-dihydroxybenzoate (5.04 g, 30 mmol), 1-bromo-2-methoxyethane (3.1 mL, 33 mmol), potassium carbonate (4.55 g, 33 mmol) and sodium iodide (1 g) in DMF (20 mL) was heated overnight at 55-60° C. before it was poured into brine (300 mL). The resulting mixture was extracted with ethyl acetate; and the ethyl acetate solution was washed with brine, dried (MgSO$_4$) and evaporated to a residue (6.17 g), which was subjected to preparative HPLC over silica gel, eluting with a gradient of 0-30% ethyl acetate in hexane over 30 min (at 100 mL/min), to afford the ether (2.72 g).

B. 2-(1-tert-Butoxycarbonylpiperidin-4-yloxy)-4-(2-methoxyethoxy)benzoic Acid

Using a procedure similar to that of Example 26-B, methyl 2-hydroxy-4-(2-methoxyethoxy)benzoate (2.72 g, 12.02 mmol) is alkylated with 1-tert-butoxycarbonyl-4-hydroxypiperidine (2.44 g, 12.02 mmol) to afford methyl 2-(1-tert-butoxycarbonylpiperidin-4-yloxy)-4-(2-methoxyethoxy)benzoate (4.41 g).

Using a procedure similar to that of Example 26-C, the ester (4.41 g) is hydrolyzed to afford the acid (2.03 g).

C. N-(5-Chloropyridin-2-yl)-3-[4-(2-methoxy-ethoxy)-2-(piperidin-4-yloxy)benzoylamino]pyridine-2-carboxamide Trifluoroacetate Using a procedure similar to that of Example 26-D, 2-(1-tert-butoxycarbonylpiperidin-4-yloxy)-4-(2-methoxyethoxy)benzoic acid (0.818 g, 2.0 mmol) is, converted into the acid chloride.

Using a procedure similar to that of Example 26-D, the acid chloride is treated with 3-amino-N-(5-chloropyridin-2 -yl)pyridine-2-carboxamide (0.465 g, 2.0 mmol) to afford 3-[2-(1-tert-butoxycarbonylpiperidin-4-yloxy)-4-(2-methoxyethoxy)benzoylamino]-N-(5-chloropyridin-2-yl)pyridine-2-carboxamide (0.435 g) as the first crop after crystallization.

Using a procedure similar to that of Example 1-J, the above compound was treated with 1:1 TFA:dichloromethane (4 mL each), to afford, after filtration of some insoluble material and evaporation, the title compound as the bis(trifluoroacetate) salt (0.361 g).
$^{1}$NMR

EXAMPLE 33

Preparation of 3-[2-(cis-4-Aminocyclohexyloxy)-4-(2-methoxy-ethoxy)benzoylamino]-N-(5-chloropyridin-2-yl)pyridine-2-carboxamide Tris(trifluoroacetate)

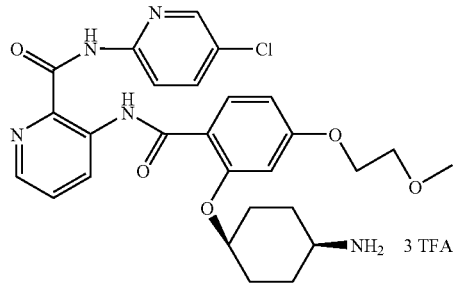

A. 2-(cis-4-tert-Butoxycarbonylaminocyclohexyloxy)-4-(2-methoxyethoxy)benzoic Acid Using a procedure similar to that of Example 29-A, methyl 2-hydroxy-4-(2-methoxyethoxy)benzoate (6.0 g, 26.52 mmol) is alkylated with trans-4-tert-butoxycarbonylamino-cyclohexanol (5.38 g, 26.52 mmol) to afford the ether (2.70 g), which is used without further purification.

Using a procedure similar to that of Example 29-A, the above crude ester (2.7 g) is hydrolyzed to afford the acid (0.96 g), which is used without further purification.

B. 3-[2-(cis-4-Aminocyclohexyloxy)-4-(2-methoxy-ethoxy)-benzoylamino]-N-(5-chloropyridin-2-yl)pyridine-2-carboxamide Trifluoroacetate Using a procedure similar to that of Example 26-D, 2-(cis-4-tert-butoxycarbonylaminocyclohexyloxy)-4-(2-methoxyethoxy)benzoic acid (6.96 g, 2.35 mmol) is converted into the acid chloride.

Using a procedure similar to that of Example 26-D, the acid chloride is treated with 3-amino-N-(5-chloropyridin-2-yl)pyridine-2-carboxamide (0.547 g, 2.35 mmol) to afford 3-[2-(cis-4-tert-butoxycarbonylaminocyclohexyloxy)-4-(2-methoxyethoxy)benzoylamino]-N-(5-chloropyridin-2-yl)-pyridine-2-carboxamide (0.210 g) after chromatography over silica gel, eluting with a gradient of 0-50% ethyl acetate in hexane.

Using a procedure similar to that of Example 1-J, the above compound was treated with 1:1 TFA:dichloromethane (3 mL each), to afford, after filtration of some insoluble material and evaporation, the title compound as the tris(trifluoroacetate) salt (0.153 g).

EXAMPLE 34

Preparation of 3-[2-(3-Amino-2,2-dimethylpropoxy)-4-(2-methoxyethoxy)benzoylamino]-N-(5-chloropyridin-2-yl)-pyridine-2-carboxamide Bis(trifluoroacetate)

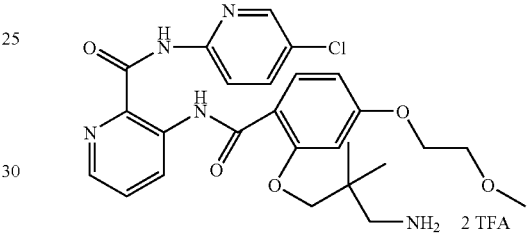

A. 2-(3-tert-Butoxycarbonylamino-2,2-dimethylpropoxy)-4-(2-methoxyethoxy)benzoic Acid Using a procedure similar to that of Example 26-B, methyl 2-hydroxy-4-(2-methoxyethoxy)benzoate (3.2 g, 14.14 mmol) is alkylated with 3-tert-butoxycarbonylamino-2,2-dimethylpropanol (2.88 g, 14.14 mmol) to afford methyl 2-(3-tert-butoxycarbonylamino-2,2-dimethylpropoxy)-4-(2-methoxyethoxy)benzoate (4.982 g) after purification over silica gel, eluting with a gradient of 0-40% ethyl acetate in hexane.

Using a procedure similar to that of Example 26-C, the ester (4.98 g) is hydrolyzed to afford the acid (1.28 g).

B. 3-[2-(3-Amino-2,2-dimethylpropoxy)-4-(2-methoxy-ethoxy)benzoylamino]-N-(5-chloropyridin-2-yl)pyridine-2-carboxamide Trifluoroacetate Using a procedure similar to that of Example 26-D, 2-(3-tert-butoxycarbonylamino-2,2-dimethylpropoxy)-4-(2-methoxyethoxy)benzoic acid (1.2 g, 3.02 mmol) is converted into the acid chloride.

Using a procedure similar to that of Example 26-D, the acid chloride is treated with 3-amino-N-(5-chloropyridin-2-yl)pyridine-2-carboxamide (0.703 g, 3.02 mmol). The reaction mixture is diluted with dichloromethane and partitioned between cold water and a mixture of ethyl acetate and hexane with the aqueous layer being acidified with a mixture of 5 N HCl and ice. The separated aqueous layer is basified with aqueous potassium carbonate and washed with ethyl acetate before it is acidified with ice cold 5 N HCl and extracted with ethyl acetate. The organic phase is washed with water, dried (MgSO₄), and evaporated. The product is isolated by elution from silica gel, using a gradient of 0 to 50% ethyl acetate, to provide 3-[2-(3-tert-butoxycarbonylamino-2,2-dimethylpropoxy)-4-(2-methoxy-ethoxy)benzoylamino]-N-(5-chloropyridin-2-yl)pyridine-2-carboxamide (0.11 g).

Using a procedure similar to that of Example 1-J, the above compound is treated with 1:1 TFA:dichloromethane (2 mL each) for 5 h, to afford the title compound as the bis(trifluoroacetate) salt (0.070 g).

EXAMPLE 35

Preparation of 3-[2-(3-Aminopropoxy)-4-(2-methoxyethoxy)-benzoylamino]-N-(5-chloropyridin-2-yl)pyridine-2-carboxamide Bis(trifluoroacetate)

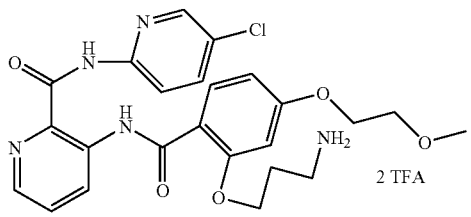

A. 2-(3-tert-Butoxycarbonylaminopropoxy)-4-(2-methoxy-ethoxy)benzoic Acid

Using a procedure similar to that of Example 26-B, methyl 2-hydroxy-4-(2-methoxyethoxy)benzoate (7.47 g, 33.1 mmol) is alkylated with 3-tert-butoxycarbonylaminopropanol (5.51 mL, 33.1 mmol) to afford methyl 2-(3-tert-butoxy-carbonylaminopropoxy)-4-(2-methoxyethoxy)benzoate in two crude portions (4.35 g and 10.56 g) after purification over silica gel, eluting with a gradient of 0-60% ethyl acetate in hexane.

Using a procedure similar to that of Example 30-A, the ester in two crude portions (4.35 g and 10.56 g) is hydrolyzed to afford the acid, obtained in several portions (0.28 g and 3.89 g; 0.73 g).

B. 3-[2-(3-Aminopropoxy)-4-(2-methoxyethoxy) benzoylamino]-N-(5-chloropyridin-2-yl)pyridine-2-carboxamide Trifluoroacetate Using a procedure similar to that of Example 26-D, 2-(3-tert-butoxycarbonylaminopropoxy)-4-(2-methoxy-ethoxy) benzoic acid (1.48 g, 4.0 mmol) is converted into the acid chloride.

Using a procedure similar to that of Example 34-B, the acid chloride is treated with 3-amino-N-(5-chloropyridin-2-yl)pyridine-2-carboxamide (0.931 g, 4.0 mmol). Isolation of the product from silica gel, eluting with a gradient of 0-40% ethyl acetate in hexane, affords 3-[2-(3-tert-butoxycarbonylaminopropoxy)-4-(2-methoxyethoxy)benzoyl-amino]-N-(5-chloropyridin-2-yl)pyridine-2-carboxamide (0.30 g).

Using a procedure similar to that of Example 1-J, the above compound is treated with 1:1 TFA:dichloromethane (2 mL each) for 5 h, to afford the title compound as the bis(trifluoroacetate) salt (0.278 g).

EXAMPLE 36

Preparation of 3-[4-Acetyl-2-(3-aminopropoxy)benzoylamino]-N-(5-chloropyridin-2-yl)pyridine-2-carboxamide Trifluoroacetate

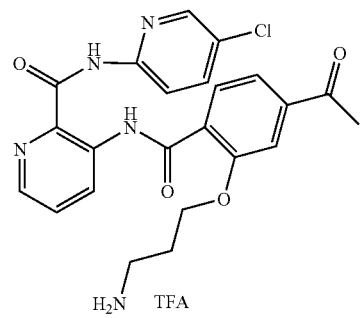

A. 4-(2-Methyl-1,3-dioxolan-2-yl)-2-(methoxymethoxy)-benzoic Acid

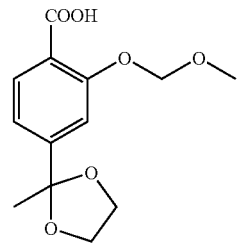

To a solution of methoxymethyl 3-(2-methyl-1,3-dioxolan-2-yl)phenyl ether (8.16 g, 36.4 mmol) in ether (200 mL) was added dropwise tert-butyl lithium (1.7 M solution, 26.8 mL, 1.25 equivalents) at −5 to −10° C. The reaction mixture was stirred 15 min before carbon dioxide gas was bubbled in for 5 min. The reaction mixture was allowed to warm slowly in the cold bath to about 10° C., then it was extracted with water. The aqueous layer was acidified with 5 N HCl and extracted with EtOAc. The organic phase was dried (MgSO₄) and evaporated to afford a crude product which was triturated with hexane to afford the benzoic acid (4.54 g).

B. N-(5-Chloropyridin-2-yl)-3-[4-(2-methyl-1,3-dioxolan-2-yl)-2-(methoxymethoxy)benzoylamino] pyridine-2-carboxamide

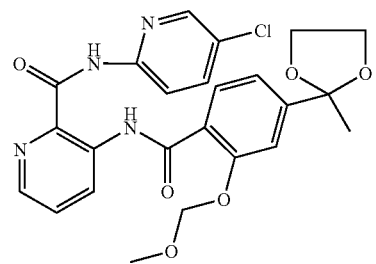

Using a procedure similar to that of Example 26-D, 4-(2-methyl-1,3-dioxolan-2-yl)-2-(methoxymethoxy)benzoic acid (4.54 g, 16.9 mmol) is treated with oxalyl chloride (1.48 mL, 16.9 mmol) and pyridine (1.37 mL, 16.9 mmol) in dichloromethane (150 mL) to afford the acid chloride.

The acid chloride in dichloromethane (50 mL) is treated with 3-amino-N-(5-chloropyridin-2-yl)pyridine-2-carboxamide (4.20 g, 16.9 mmol) And pyridine (2.73 mL, 2×16.9 mL) in dichloromethane (50 mL). After filtration of some insoluble material from the reaction mixture (with washing with dichloromethane), the organic solution is washed with 1 N HCl, cold 2 N NaOH, cold dilute HCl, and satd NaHCO₃ before it is dried and evaporated to a crude product (3.10 g), which is used directly without further purification.

C. 3-[4-Acetyl-2-hydroxybenzoylamino]-N-(5-chloropyridin-2-yl)pyridine-2-carboxamide

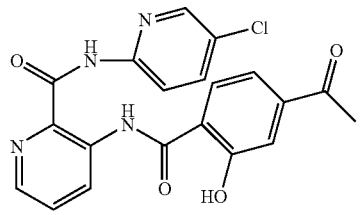

N-(5-Chloropyridin-2-yl)-3-[4-(2-methyl-1,3-dioxolan-2-yl)-2-(methoxymethoxy)benzoylamino]pyridine-2-carboxamide (3.10 g) is treated with a solution of TFA (20 mL) and water (20 mL) for 2 h before the solution is evaporated. The residue is slurried with ethyl acetate to provide a solid which is collected and washed. The solid is dispersed in ethyl acetate and extracted with a mixture of aqueous potassium carbonate and 1 N NaOH. The resulting organic phase is washed with very dilute HCl, dried and evaporated to afford the product as a solid (0.476 g), which is used directly without further purification.

D. 3-[4-Acetyl-2-(3-tert-butoxycarbonylaminopropoxy)-benzoylamino]-N-(5-chloropyridin-2-yl)pyridine-2-carboxamide A solution of 3-[4-acetyl-2-hydroxybenzoylamino]-N-(5-chloropyridin-2-yl)pyridine-2-carboxamide (0.410 g, 1 mmol), 3-(tert-butoxycarbonylamino)propyl bromide (0.286 g, 1.2 mmol) and a dash of potassium iodide in DMF (30 mL) is treated with sodium hydride (60%, 44.0 mg, 1.1 mmol) and heated overnight at 70° C. The reaction mixture is cooled and portioned between 0.1 N HCl (150 mL) and ethyl acetate (150 mL). The organic phase is washed with satd NaHCO₃, dried (MgSO₄) and evaporated to a crude product (0.518 g) which is purified by flash chromatography (silica gel: gradient, 35:1 to 19:1 dichloromethane:methanol) to provide the protected amine (0.295 g, 0.050 g).

E. 3-[4-Acetyl-2-(3-aminopropoxy)benzoylamino]-N-(5-chloropyridin-2-yl)pyridine-2-carboxamide Trifluoroacetate 3-[4-Acetyl-2-(3-tert-butoxycarbonylaminopropoxy)-benzoylamino]-N-(5-chloropyridin-2-yl)pyridine-2-carboxamide (0.345 g) in dichloromethane (4 mL) is treated with TFA (4 mL) for 4 h. The reaction mixture is evaporated, and the residue is triturated twice with hexane. The solid residue is transferred to a small flask by dissolving it in methanol and evaporation to a solid which is triturated with ethyl acetate and hexane to provide the salt as a solid (139 mg).

The methoxymethyl 3-(2-methyl-1,3-dioxolan-2-yl)phenyl ether used as a starting material in Part A, above, may be prepared as follows:

F. 3-(Acetyl)phenyl Methoxymethyl Ether

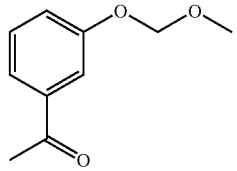

To a stirred solution of 3-hydroxyacetophenone (20.40 g, 150 mmol) in CH₂Cl₂ (450 mL) at 0° C. under N₂ was added N,N-diisopropylethylamine (52.25 mL, 300 mmol) followed by methyl chloromethyl ether (MOM chloride) (13.67 mL, 180 mmol) over a period of 30 min. The reaction was stirred at 0° C. for 30 min and then at room temperature for 2 h. The reaction was quenched with H₂O (500 mL). The organic solution was separated, washed with H₂O (2×500 mL), 0.5 N NaOH (2×100 mL), and again with H₂O (200 mL). The organic solution was dried (Na₂SO₄) and concentrated. The resulting residue was purified by filtration through a pad of silica gel using n-hexanes through 2-5% EtOAc/n-hexanes to give the desired product (17.30 g, 64%); TLC Rf: 0.45 (20% EtOAc/n-hexanes).

¹H NMR (400 MHz, CDCl₃): δ 7.62(dd, 1H, J=1.6 and 8.4 Hz); 7.59(d, 1H, J=1.6 Hz); 7.38(t, 1H, J=6 Hz); 5.23(s, 2H); 3.49(s, 3H); 2.60(s, 3H).

IS-MS (m/e): 180 (m)

Analysis for C₁₀H₁₂O₃:

Calcd: C, 66.65; H, 6.71;

Found: C, 67.73; H, 6.87.

G. Methoxymethyl 3-(2-methyl-1,3-dioxolan-2-yl)phenyl Ether

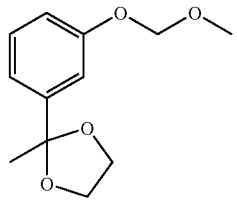

A mixture of 3-(acetyl)phenyl methoxymethyl ether (3.6 g, 20 mmol), ethylene glycol (3.72 g, 60 mmol) and pyridinium tosylate (0.075 g, 0.3 mmol, 3 mol %) in benzene (200 mL) was azeotropically refluxed for 8 h. The reaction was concentrated and the resulting residue was diluted with ethyl ether (150 mL) and washed with saturated aqueous bicarbonate (2×50 mL) and brine (100 mL). The ethyl ether solution was dried (K₂CO₃) and concentrated. The residue was suspended in n-hexanes and the by-product was precipitated. The n-hexane solution was then separated and concentrated to obtain the desired product (2.69 g, 61%); TLC Rf: 0.5 (30% EtOAc/n-hexanes).

$^1$H NMR (400 MHz, CDCl$_3$): δ 7.33(t, 1H, J=7.6 Hz); 7.22(ddd, 1H, J=1.6, 2.4 and 7.6 Hz); 7.19(bs, 1H); 7.06(dd, 1H, J=1.2 and 8.0 Hz); 5.26(s, 2H); 4.10(m, 2H); 3.86(m, 2H); 3.56(s, 3H); 1.73(s, 3H).

IS-MS (m/e): 225 (m+1)

Analysis for C$_{12}$H$_{16}$O$_4$:

Calcd: C, 64.27; H, 7.19;

Found: C, 64.46; H, 7.09.

What is claimed is:

1. A compound of formula I,

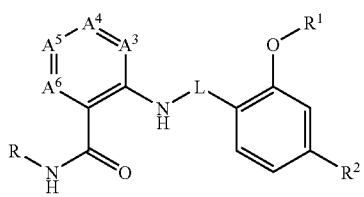

or a pharmaceutically acceptable salt thereof, wherein:

A$^3$, A$^4$, A$^5$ and A$^6$, together with the two carbons to which they are attached, complete a substituted pyridine ring in which one of A$^3$, A$^4$, A$^5$ and A$^6$ is N, and each of the others is CR$^3$, CR$^4$, CR$^5$ or CR$^6$, respectively; wherein each of R$^3$, R$^4$, R$^5$ and R$^6$ is hydrogen; or one or more of R$^3$, R$^4$, R$^5$ and R$^6$ is methyl each of the others is hydrogen; or one of R$^3$, R$^4$, R$^5$ and R$^6$ attached to a carbon which is not bonded to an N-atom is chloro and each of the others are hydrogen; or A$^3$, A$^4$, A$^5$ and A$^6$, together with the two carbons to which they are attached, complete a substituted thiophene ring in which two adjacent residues of A$^3$, A$^4$, A$^5$ and A$^6$ together form S, and each of the others is CH;

L is carbonyl or methylene;

R is 2-pyridinyl (which may bear a methyl, cyano, carbamoyl, hydroxymethyl, formyl, vinyl, amino, hydroxy, methoxy, difluoromethoxy, methylthio, fluoro or chloro substituent at the 5-position), or R is 3-pyridinyl (which may bear a methyl, fluoro or chloro substituent at the 6-position), or R is 2-thiazolyl (which may bear a methyl substituent at the 4-position or a bromo substituent at the 5-position), or R is phenyl (which may bear one, two or three substituents at the 3-, 4- or 5-position(s) independently selected from fluoro, chloro, bromo, cyano, carbamoyl, methyl, methoxy, difluoromethoxy, hydroxymethyl, formyl, vinyl, amino, hydroxy and 3,4-methylenedioxy; and in addition the phenyl may bear a 2-chloro or 2-fluoro substituent), or R is 6-indolyl (which may bear a chloro or methyl substituent at the 3-position);

R$^1$ is —(CH$_2$)$_i$-Q-(CH$_2$)$_j$—NR$^a$R$^b$ in which a) Q is a single bond; the sum of i and j is 2 or 3; and each of R$^a$ and R$^b$ is hydrogen, or each of R$^a$ and R$^b$ is independently (1-3C) normal alkyl, or R$^a$ is hydrogen and R$^b$ is (1-3C)alkyl or formyl, or NR$^a$R$^b$ is 1-pyrrolidinyl or 4-morpholinyl;

b) Q is —CH(CH$_3$)—, —C(CH$_3$)$_2$— or —CH(OH)—; each of i and j is 1; and each of R$^a$ and R$^b$ is hydrogen, or each of R$^a$ and R$^b$ is independently (1-3C) normal alkyl, or R$^a$ is hydrogen and R$^b$ is (1-3C)alkyl or formyl, or —NR$^a$R$^b$ is 1-pyrrolidinyl or 4-morpholinyl;

c) Q is cyclohexane-1,4-diyl; each of i and j is 0; R$^a$ is hydrogen; and R$^b$ is hydrogen or methyl;

d) Q is —CHR$^c$—; i is 0; j is 1; R$^a$ is hydrogen or methyl; and R$^b$ and R$^c$ together are —(CH$_2$)$_k$— wherein k is 2 or 3;

e) Q is —CHR$^c$—; i is 1; j is 1; R$^a$ is hydrogen or methyl; and R$^b$ and R$^c$ together are —(CH$_2$)$_k$— wherein k is 1, 2 or 3; or f) Q is —CHR$^c$—; i is 0 or 1; j is 2; R$^a$ is hydrogen or methyl; and R$^b$ and R$^c$ together are —(CH$_2$)$_k$— wherein k is 2; and R$^2$ is fluoro, chloro, (1-4C)alkyl, —NR$^d$R$^e$, —OR$^f$, acetyl, —CONR$^g$R$^h$ or NHCOR$^i$ in which each of R$^d$ and R$^e$ is independently hydrogen or (1-3C)alkyl; or —NR$^d$R$^e$ is 1-pyrrolidinyl, 1-piperidinyl, 1-piperazinyl, hexahydro-1,4-diazepin-1-yl or 4-morpholinyl (in which the 1-piperazinyl or hexahydro-1,4-diazepin-1-yl may bear a 4-methyl substituent and the 1-piperidinyl may bear one or two 4-methyl substituents); R$^f$ is (1-3C)alkyl, 2-fluoroethyl, 2,2,2-trifluoroethyl or 2-methoxyethyl; each of R$^g$ and R$^h$ is hydrogen, or R$^g$ is hydrogen and R$^h$ is (1-6C)alkyl or (3-6C)cycloalkyl, or each of R$^g$ and R$^h$ is independently (1-3C)alkyl, or —NR$^g$R$^h$ is 1-pyrrolidinyl, 1-piperidinyl, 1-piperazinyl or 4-morpholinyl (in which the 1-piperazinyl may bear a 4-methyl substituent and the 1-piperidinyl may bear one or two 4-methyl substituents); and R$^i$ is hydrogen, (1-6C)alkyl or (3-6C)cycloalkyl.

2. The compound or salt of claim 1 wherein

R is 2-pyridinyl, which bears a methyl, fluoro or chloro substituent at the 5-position; or R is 2-thiazolyl, which may bear a methyl substituent at the 4-position or a bromo substituent at the 5-position, or R is phenyl, which may bear a fluoro, chloro or methoxy substituent at the 4-position; or R is 6-indolyl;

R$^1$ is 2-aminoethyl, 2-(dimethylamino)ethyl, 2-(formylamino)ethyl, 3-aminopropyl, 3-(formylamino)propyl, 3-(1-pyrrolidinyl)propyl, 3-(4-morpholinyl)propyl, 3-amino-2-methylpropyl, 3-amino-2,2-dimethylpropyl, 3-amino-2-hydroxypropyl, cis-4-aminocyclohexyl, cis-4-(methylamino)-cyclohexyl, 3-pyrrolidinyl, 3-piperidinyl, 3-azetidinyl-methyl, 3-pyrrolidinylmethyl, 3-piperidinylmethyl, 4-piperidinyl, 4-piperidinylmethyl or 1-methyl-piperidin-4-yl; and R$^2$ is fluoro, isopropyl, tert-butyl, dimethylamino, 1-pyrrolidinyl, 1-piperidinyl, 1-piperazinyl, hexahydro-1,4-diazepin-1-yl, 4-morpholinyl, methoxy, ethoxy, 2-fluoroethoxy, 2,2,2-trifluoroethoxy, 2-methoxyethoxy or acetyl.

3. The compound or salt of claim 2 wherein

R is 5-chloropyridin-2-yl, 2-thiazolyl, 4-methylthiazol-2-yl, 5-bromothiazol-2-yl or 4-chlorophenyl;

R$^1$ is 2-aminoethyl, 2-(formylamino)ethyl, 3-amino-propyl, 3-(formylamino)propyl, 3-amino-2,2-dimethylpropyl, cis-4-aminocyclohexyl, 3-piperidinylmethyl or 4-piperidinyl; and R$^2$ is fluoro, isopropyl, tert-butyl, dimethylamino, 1-pyrrolidinyl, 4-morpholinyl, 2-fluoroethoxy, 2,2,2-trifluoroethoxy, 2-methoxyethoxy or acetyl.

4. The compound or salt of claim 3 wherein

R is 5-chloropyridin-2-yl;

R$^1$ is 3-amino-2,2-dimethylpropyl, cis-4-amino-cyclohexyl, or 4-piperidinyl; and R$^2$ is 1-pyrrolidinyl, 4-morpholinyl, 2-fluoroethoxy or 2-methoxyethoxy.

5. The compound or salt of any one of claims 1-4 wherein one of $A^3$, $A^4$, $A^5$ and $A^6$ is N, and each of the others is $CR^3$, $CR^4$, $CR^5$ or $CR^6$, respectively; in which
each of $R^3$, $R^4$ and $R^6$ is hydrogen and $R^5$ is hydrogen or methyl.

6. The compound or salt of claim 5 wherein each of $R^3$, $R^4$, $R^5$ and $R^6$ is hydrogen.

7. The compound or salt of claim 6 wherein $A^3$ is N.

8. The compound or salt of claim 6 wherein $A^4$ is N.

9. The compound or salt of claim 6 wherein $A^5$ is N.

10. The compound or salt of claim 6 wherein $A^6$ is N.

11. The compound or salt of any one of claims 1-4 wherein $A^3$, $A^4$, $A^5$ and $A^6$, together with the two carbons to which they are attached, complete a substituted thiophene ring in which
    (a) $A^3$ and $A^6$ are each CH; or
    (b) $A^3$ and $A^4$ are each CH.

12. The compound or salt of any one of claims 1-4 wherein L is carbonyl.

13. The compound or salt of any one of claims 1-4 wherein L is methylene.

14. The compound of claim 1 which is:
    (a) N-(5-chloropyridin-2-yl)-3-[2-(piperidin-4-yloxy)-4-(pyrrolidin-1-yl)benzoylamino]pyridine-4-carboxamide;
    (b) 4-[4-tert-butyl-2-(piperidin-4-yloxy)benzoylamino]-N-(5-chloropyridin-2-yl)pyridine-3-carboxamide; or
    (c) 3-[2-(cis-4-Aminocyclohexyloxy)-4-(2-fluoroethoxy)-benzoylamino]-N-(5-chloropyridin-2-yl)pyridine-2-carboxamide,
    or a pharmaceutically acceptable salt thereof.

15. A pharmaceutical composition comprising in association with a pharmaceutically acceptable carrier, diluent or excipient, a compound of formula I, or a pharmaceutically acceptable salt thereof, as provided in claim 1.

16. A method of treating a thromboembolic disorder in a mammal in need of treatment comprising administering to the mammal an effective amount of a compound of formula I, or pharmaceutically acceptable salt thereof, as described in claim 1.

* * * * *